US007635685B2

(12) United States Patent
Baasov et al.

(10) Patent No.: US 7,635,685 B2
(45) Date of Patent: Dec. 22, 2009

(54) BIFUNCTIONAL ANTIBIOTICS FOR TARGETING RRNA AND RESISTANCE-CAUSING ENZYMES AND FOR INHIBITION OF ANTHRAX LETHAL FACTOR

(75) Inventors: Timor Baasov, Haifa (IL); Micha Fridman, Kiryat Bialik (IL); **Val Key: (a) PPh₃, diisopropylazodicarboxylate (DIAD), thioacetic acid, THF; (b) Hydrazinium acetate, DMF.

Key: (a) Cyclohexanone dimethyl ketal, CSA, DMF; (b) Ac₂O, pyridine, DMAP; (c) AcOH/H₂O; (d) 1,1'-thiocarbodiimidazole,THF; (e) Bu₃SnH, toluene. (f) HF/Pyridine.

designed donors structures

The Synthesis of Glycosyl Donors 5c, 5e and 8b

Reagents and conditions: (a) TBDPSCl, pyridine, 4-DMAP, 50°C. (b) BzCl, pyridine, 4-DMAP (c) HF/pyridine. (d) p.toluenesulfonylchloride, pyridine, 50°C.(e) NaN$_3$, DMF, HMPA, 50°C. (f) Tf$_2$O, pyridine. (g) Ac$_2$O, pyridine. (h) 4-methylbenzenethiol, BF$_3$OEt$_2$, CH$_2$Cl$_2$. (i) NaOMe (cat.), MeOH. (j) p. toluenesulfonylchloride, CH$_2$Cl$_2$, Et$_3$N, r.t.

Fig. 12

The synthesis of acceptor 1 and of compounds II-XIII.

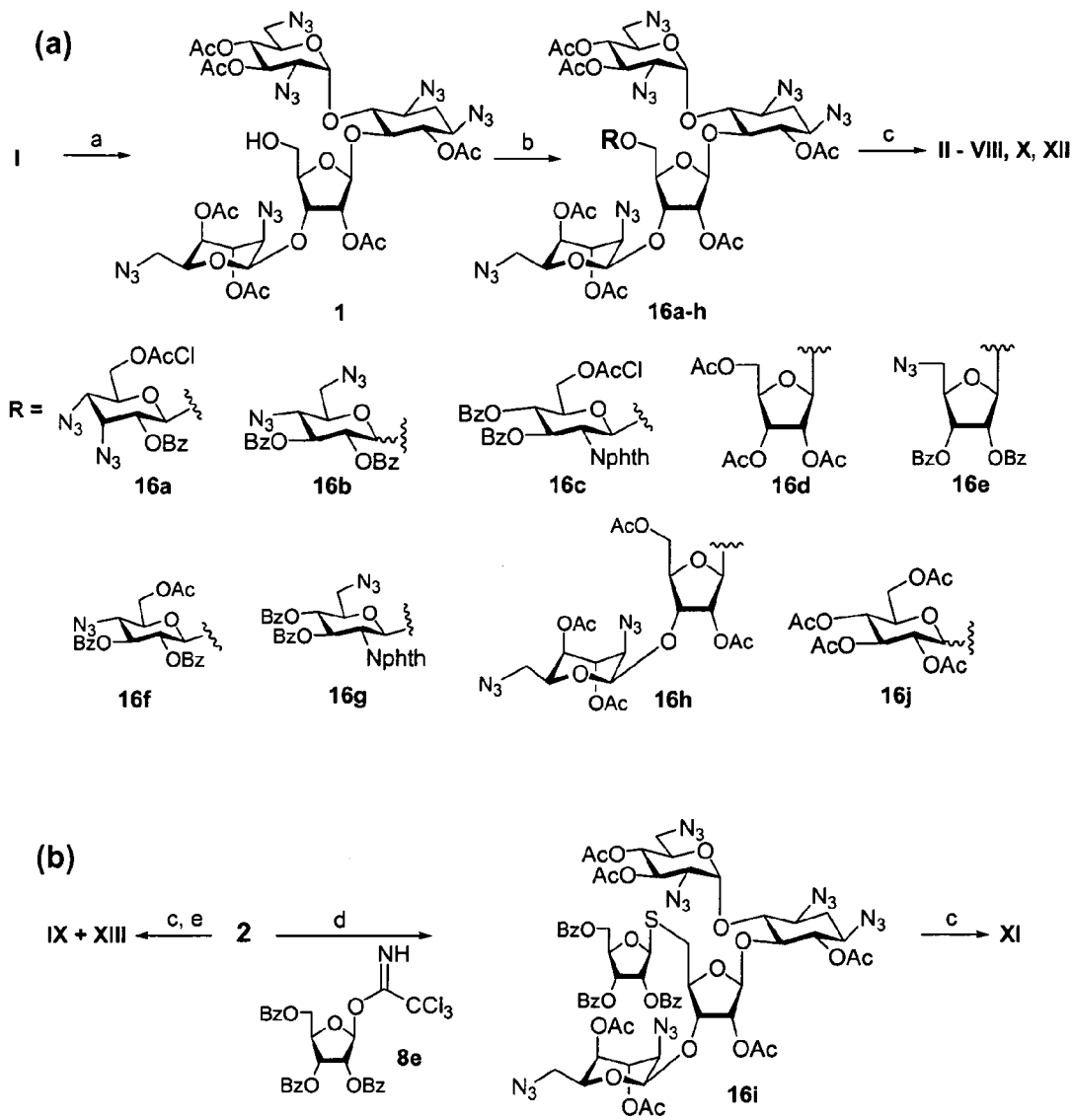

[a] Reagents and conditions: (a) (i) TfN$_3$, Et$_3$N, CuSO$_4$, in CH$_2$Cl$_2$/MeOH/H$_2$0 3:10:3; (ii) TBDMSCl, pyridine, DMAP; (iii) Ac$_2$O, pyridine, DMAP; (iv) HF/pyridine, 57% for the four steps. (b) 9, 5f, 10, 11, 8b, 5e, 5c, 19a, each separately in the presence of NIS, TfOH; (c) For II-III, and V-XIII: (i) MeNH$_2$ (33% in EtOH); (ii) PMe$_3$, NaOH 0.1M, THF/ H$_2$O 3:1; For IV: (i) NaOMe/MeOH; (ii) PMe$_3$, NaOH 0.1M, THF/H$_2$O 3:1. (d) BF$_3$ Et$_2$O, CH$_2$Cl$_2$, -10 °C; (e) Biogel P-2 size-exclusion chromatography.

BIFUNCTIONAL ANTIBIOTICS FOR TARGETING RRNA AND RESISTANCE-CAUSING ENZYMES AND FOR INHIBITION OF ANTHRAX LETHAL FACTOR

This application is a continuation-in-part of PCT Patent Application No. PCT/IL2004/000490, filed Jun. 9, 2004, which claims priority from U.S. patent application Ser. No. 10/829,976, filed Apr. 23, 2004, and U.S. Provisional Patent Applications Nos. 60/540,359, filed Feb. 2, 2004, and 60/484,293, filed Jul. 3, 2003. This application also claims the benefit of priority from U.S. Provisional Patent Application No. 60/608,372, filed Sep. 10, 2004. The teachings of the above applications are hereby incorporated by reference as if fully set forth herein.

FIELD OF THE INVENTION

The present invention relates to bi-functional antibiotics, and in particular to aminoglycosides which are capable of reducing the efficacy of and/or blocking antibiotic resistance. The aminoglycosides of the present invention are suitable for inhibition of anthrax lethal factor, hence are suitable for use as a cure for anthrax.

BACKGROUND OF THE INVENTION

The rapid spread of antibiotic resistance in pathogenic bacteria has prompted a continuing search for new agents capable of antibacterial activity. Indeed, microbiologists today warn of a "medical disaster" which could lead back to the era before penicillin, when even seemingly small infections were potentially lethal. Thus, research into the design of new antibiotics is of high priority (1-3). One way to delay the emergence of antibiotic-resistance is to develop new synthetic materials that can selectively inhibit bacterial enzymes, via novel mechanisms of action. However, this approach is both time-consuming and financially prohibitive, yet remains indispensable if an acceptable level of care is to be provided in the immediate future. On the other hand, it may be less costly in time and money to employ strategies to circumvent existing bacterial resistance mechanisms and thereby to restore usefulness to antibacterials that have become compromised by resistance (4). The remarkable advances in recent years in elucidating the mechanisms of resistance to various clinical antibiotics on the molecular level provide complementary tools to this approach via structure-based and mechanism-based design.

One example of an important group of antibiotics which could benefit from such a redesign is the aminoglycoside class of antibiotics. Aminoglycosides (as shown in prior art FIG. 1) are highly potent, broad-spectrum antibiotics with many desirable properties for the treatment of life-threatening infections (5). Their history begins in 1944 with streptomycin and was thereafter marked by the successive introduction of a series of milestone compounds (neomycin, kanamycin, gentamycin, tobramycin, and others), which definitively established the usefulness of this class of antibiotics for the treatment of gram-negative bacillary infections (6). It is believed that aminoglycosides exert their therapeutic effect by interfering with translational fidelity during protein synthesis via interaction with the A-site rRNA on the 16S domain of the ribosome (7,8). Recent achievements in ribosome structure determination have provided fascinating new insights into the decoding site of the ribosome at high resolution and how aminoglycosides might induce misreading of the genetic code.

Unfortunately, prolonged clinical use of currently available aminoglycosides has resulted in effective selection of resistance to this family of antibacterial agents (9). Presently, resistance to these agents is widespread among pathogens worldwide which severely limits their usefulness. The primary mechanism for resistance to aminoglycosides is the bacterial acquisition of enzymes which modify this family of antibiotics by acetyltransferase (AAC), adenyltransferase (ANT), and phosphotransferase (APH) activities (as shown in prior art FIG. 2). Among these enzyme families, aminoglycoside 3'-phosphotransferases [APH(3')s], of which seven isozymes are known, are widely represented. These enzymes catalyze transfer of γ-phosphoryl group of ATP to the 3'-hydroxyl of many aminoglycosides, rendering them inactive because the resulted phosphorylated antibiotics no longer bind to the bacterial ribosome with high affinity. Due to the unusually broad spectrum of aminoglycosides that can be detoxified by APH(3') enzymes, much effort has been put into understanding the structural basis for their promiscuity in substrate recognition and catalysis (10).

To tackle the problem of antibiotic resistance, many structural analogs of natural aminoglycosides have been synthesized over the past decade (11). In the majority of these studies a minimal structural motif, which is common for a series of structurally related aminoglycosides, has been identified and used as a scaffold for the construction of diverse analogs as potential new antibiotics (12). Some of the designed structures showed considerable antibacterial activities. Since the structural and mechanistic information on the target(s) of aminoglycosides and their respective resistance enzymes has only began to emerge in the past few years, this information stimulated novel developments in the de novo design of molecules that bind to the ribosomal target site and simultaneously are poor substrates for resistance-causing enzymes (13, 14). These results and design principles hold the promise of the generation of a large series of designer antibiotics uncompromised by the existing mechanisms of resistance.

In view of recent events, one particular disease for which effective therapeutic strategies are urgently required is anthrax.

Anthrax is an infectious disease caused by toxigenic strains of the Gram-positive *Bacillus anthracis* (15). If inhaled, *B. anthracis* spores rapidly reach the regional lymphonodes of the lungs where they germinate and release anthrax toxins (16). These toxins inhibit the adaptive immune response, thereby enabling the bacteria to reach the blood system where they cause bacteraemia and toxaemia, which rapidly kills the host. Non-toxigenic strains of *B. anthracis* are poorly pathogenic indicating that the anthrax toxins play a major role from the very beginning of infection to death. Since anthrax is asymptomatic until the bacterium reach the blood (15, 16), the development of anti-toxin therapeutics for preventive use or in combination with antibiotics, is of high urgency (17). Alternatively, and even preferably, the development of bifunctional substances that would inactivate the released toxins and in addition would function as an antibiotic would be highly beneficial.

The anthrax toxins consist of three proteins: protective antigen (PA), edema factor (EF), and lethal factor (LF) (18). Being individually nontoxic, their toxic effects during anthrax infection require cooperation: PA binds to a cell surface receptor and forms an oligomeric pore that translocates both EF and LF into the cytosol of target cells. Once inside the cell, EF causes edema via $Ca^{2+}$/calmodulin-dependent adenylate cyclase activity. LF is a zinc-dependent endopeptidase that specifically cleaves most isoforms of mitogen-activated protein kinase kinases, thereby inhibiting one or more signaling pathways of the host macrophage (19). Through a mechanism that is not yet well understood, this results in the death of the host. Strains of *B. anthracis* deficient in EF remain pathogenic, while those lacking LF become attenuated. LF is therefore considered the dominant virulence factor of anthrax (20).

Consequently, an intensive search for specific inhibitors of LF has been performed during the last years (17, 21-22).

The prior art does not teach or suggest a highly effective group of aminoglycosides which both share certain structural features of currently available aminoglycosides while also being able to reduce or eliminate antibiotic resistance. The prior art also does not teach or suggest such aminoglycosides which have reduced side effects. The prior art also does not teach or suggest such aminoglycosides which are capable of functioning both by inhibition of anthrax lethal factor, and as an antibiotic and are therefore highly effective for treatment of anthrax.

There is thus a widely recognized need for, and it would be highly advantageous to have, bifunctional antibiotics which both inactivate toxins and function as an antibiotic, while reducing or eliminating antibiotic resistance, and further resulting in reduced side effects. Such antibiotics would be highly beneficial in the treatment of bacterial infections such as anthrax.

SUMMARY OF THE INVENTION

The present invention overcomes the deficiencies of the prior art by providing a novel group of aminoglycosides which share some structural features of currently available aminoglycosides with regard to the backbone, while also having significant structural differences. The similarity enables these aminoglycosides to be highly potent and effective antibiotics, while the significant differences enable these aminoglycosides to reduce or even block antibiotic resistance. These aminoglycosides are highly effective for treatment of anthrax.

The present invention represents a new class of bifunctional antibiotics that circumvent antibiotic resistance and that also have a high potential for immediate therapeutic applications. Without wishing to be limited by a single hypothesis, it is believed that the aminoglycosides of the present invention target both bacterial rRNA and inhibit resistance-causing enzymes. These aminoglycosides are therefore a new class of semi-synthetic analogs of currently available aminoglycosides, which are useful for many different functions, including determining important complementary information on their antibacterial activity, interaction with resistance-causing enzymes in the means of kinetics of binding and high-resolution three-dimensional structures of binary and ternary complexes, and binding to the A-site rRNA. The new design strategies, methodologies and principles developed and discussed in the present invention are also expected to be valuable for unraveling similar problems posed to other families of antibiotics and other drugs.

According to preferred embodiments of the present invention, compounds belonging to the novel group of aminoglycosides described above have the general formula I:

Formula I 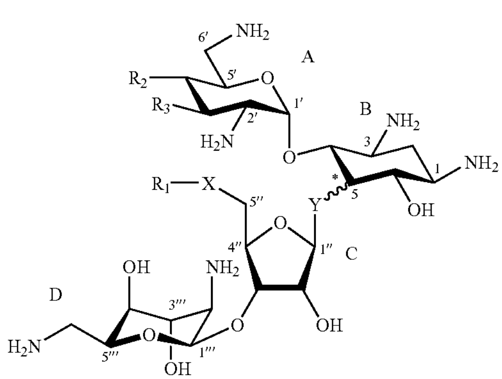 wherein:

$R_1$ is a monosaccharide residue or an oligosaccharide residue;

X and Y are independently oxygen or sulfur;

$R_2$ and $R_3$ are each independently selected from the group consisting of hydrogen, hydroxy, thiol, amine, alkyl, cycloalkyl, aryl, alkoxy, aryloxy, thioalkoxy and thioaryloxy; and wherein the carbon at the fifth position of ring B has an R configuration or an S configuration;

and pharmaceutically acceptable salts thereof.

As used herein, the term "hydroxy" refers to a —OH group.

The term "thiol" refers to a —SH group.

The term "alkyl", as used herein, refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. When substituted, the substituent group can be, for example, halo, hydroxy, cyano, nitro, azo and amine, as these terms are defined herein.

A "cycloalkyl" group refers to an all-carbon monocyclic or fused ring (i.e., rings which share an adjacent pair of carbon atoms) group wherein one of more of the rings does not have a completely conjugated pi-electron system. Illustrative examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, halo, hydroxy, cyano, nitro, azo and amine, as these terms are defined herein.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, halo, hydroxy, cyano, nitro, azo and amine, as these terms are defined herein.

An "alkoxy" group refers to both an —O-alkyl and an —O-cycloalkyl group, as defined herein.

An "aryloxy" group refers to both an —O-aryl group, as defined herein.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

An "azo" group refers to a —N=NR' group, wherein R' is hydrogen, alkyl, cycloalkyl or aryl.

A "halo" group refers to fluorine, chlorine, bromine or iodine.

An "amine" group refers to an —NR'R" group where R' is as defined hereinabove and R" is as defined herein for R'.

A "nitro" group refers to a $—NO_2$ group.

A "cyano" group refers to a —C≡N group.

Preferably X is oxygen. Also preferably, Y is oxygen. Optionally and preferably, $R_1$ is a monosaccharide residue. More preferably, the monosaccharide residue is a five-membered (furanose) or a six-membered (pyranose) monosaccharide residue. Also more preferably, the monosaccharide residue comprises at least one amine group and/or at least one aminoalkyl group. Optionally and more preferably, the at least one amine group and/or the at least one aminoalkyl group is at one or more of positions 2, 3, 4 or 5. As used herein, the term "aminoalkyl" refers to an alkyl group, as defined hereinabove, which is substituted by an amine group, as defined hereinabove. Optionally, at least one aminoalkyl group is an aminomethyl group (—$CH_2$—$NH_2$).

Optionally and preferably, if the monosaccharide residue is a pyranose monosaccharide residue, the aminomethyl group is at position 5.

Also optionally and preferably, if the monosaccharide residue is a pyranose monosaccharide residue, the amine group is at one or more of positions 2, 3 or 4.

Also optionally and preferably, if the monosaccharide residue is a furanose monosaccharide residue, the aminoalkyl group is at position 4.

Optionally, the monosaccharide residue is a L-monosaccharide or a D-monosaccharide.

According to preferred embodiments of the present invention, $R_1$ is an oligosaccharide residue. Preferably, the oligosaccharide residue comprises at least two monosaccharide residues, wherein each is independently a five-membered (furanose) or a six-membered (pyranose) monosaccharide residue. More preferably, at least one of the at least two monosaccharide residues comprises at least one amine group and/or at least one aminoalkyl group. Most preferably, the at least one amine group is at position 2 of a pyranose monosaccharide residue. Also most preferably, the at least one aminoalkyl group is at position 5 of a pyranose monosaccharide residue.

Optionally and preferably, the oligosaccharide comprises a furanose monosaccharide linked to a pyranose monosaccharide.

Optionally, each of the at least two monosaccharide residues is independently a D-monosaccharide or an L-monosaccharide.

Alternatively, the oligosaccharide residue comprises at least four monosaccharide residues, each being independently a five-membered (furanose) or a six-membered (pyranose) monosaccharide residue. Preferably, the oligosaccharide residue is a neomycin B residue. Other oligosaccharide residues include, for example, a Paromomycin residue, a Ribostamycin residue, a Gentamycin residue, a Amikacin residue, a Neamine residue, a Nebramine residue and a Tobramine residue.

According to other preferred embodiments of the present invention, X is sulfur and $R_1$ is a monosaccharide residue. Preferably, the monosaccharide is a furanose monosaccharide residue.

According to still other preferred embodiments of the present invention, there are provided novel compounds each having the general formula II:

Formula II

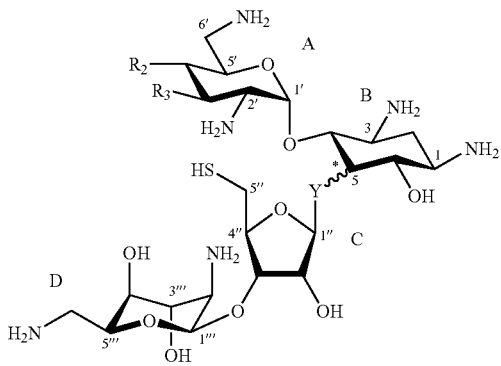

wherein:

Y is oxygen or sulfur;

$R_2$ and $R_3$ are each independently hydrogen, hydroxy, thiol, amine, alkyl, cycloalkyl, aryl, alkoxy, aryloxy, thioalkoxy and thioaryloxy; and wherein the carbon at the fifth position of ring B has an R configuration or an S configuration;

and pharmaceutically acceptable salts thereof.

Preferably, Y is oxygen, and $R_2$ and $R_3$ are both hydroxy.

According to still other preferred embodiments of the present invention, there are provided novel compounds each having the general formula III:

Formula III

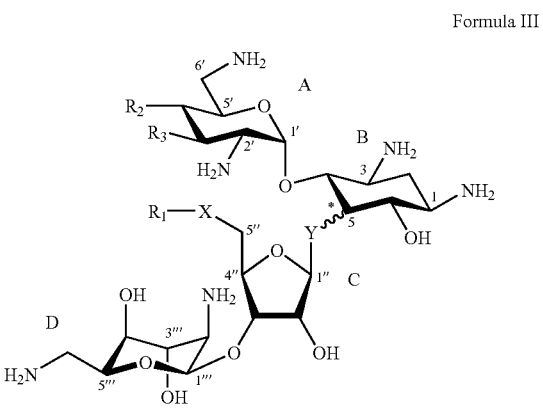

wherein:

$R_1$ is a monosaccharide residue or an oligosaccharide residue;

X is disulfide;

$R_2$ and $R_3$ are each independently selected from the group consisting of hydrogen, hydroxy, thiol, amine, alkyl, cycloalkyl, aryl, alkoxy, aryloxy, thioalkoxy and thioaryloxy; and wherein the carbon at the fifth position of ring B has an R configuration or an S configuration;

and pharmaceutically acceptable salts thereof.

As used herein, the term "disulfide" refers to a compound having two sulfur atoms mutually bonded by a single bond.

Preferably, $R_1$ is an oligosaccharide residue and more preferably an oligosaccharide residue having at least four monosaccharide residues, as described hereinabove.

Optionally and preferably, the oligosaccharide residue is a Neomycin B residue.

It should be noted that wherever reference is made to a general formula or a specific compound according to the present invention, pharmaceutically acceptable salts are also optionally included.

All of the different structures of the preferred compounds according to the present invention are shown in FIG. 16.

Without wishing to be limited by a single hypothesis, the present invention is believed to have better stability and greater resistance to bacterial enzymes for a number of reasons, including the optional presence of a thiol moiety at X, which is more resistant to hydrolysis. The presence of a monosaccharide or oligosaccharide at $R_1$ also increases resistance to hydrolysis. Again without wishing to be limited by a single hypothesis, resistance to hydrolysis is also believed to decrease toxicity, as the compounds of the present invention are expected to hydrolyze within the body (outside of bacterial cells) at a lower rate, and hence to potentially produce fewer toxic degradation products.

Some background for the rational design of antibiotics is now provided. The first rationally designed semisynthetic aminoglycoside which was selected for chemotherapeutic use is dibekacin (3',4'-dideoxykanamycin B), developed in 1975 by Umezawa and co-workers (23a). The rationale behind the development of this aminoglycoside variant was to overcome the resistance to kanamycins due to bacterial enzymes that modify them by 3'-O-phosphorylation [APH (3')]. Indeed dibekacin showed strong activity not only against resistant *staphylococci* and Gram-negative bacteria, but also against *Pseudomonas*. This successful result boosted the synthesis of numerous 3'-deoxy and 3',4'-dideoxy derivatives of other aminoglycosides, some of which were active against resistant bacteria producing APH(3'). Another approach to rationally designed semi-synthetic aminoglycosides active against resistant bacteria is the acylation or alkylation of one or several amino groups of aminoglycoside. This approach lead to the development of amikacin by 1-N-acylation of kanamycin B with (S)-4-amino-2-hydroxybutiric acid (AHB), developed by Kawaguchi and co-workers and has been used in market since 1977 (23b). Similar approaches lead to the development of netilimicin (1985), isepamicin (1988), and arbekacin (1990), which are marketed as chemotherapeutic agents, and were produced by 1-N-acylation with different acylating groups (24). However, novel resistant bacteria emerged to these antibiotics and again were shown to be dependent on new types of aminoglycoside-modifying enzymes.

To overcome the emerged resistance to amikacin, recently, Mobashery and co-workers (13) took advantage of the known 3D NMR structure for paromomycin bound to the A-site rRNA (25), and, by using docking experiments, a total of seven structures have been selected and synthesized. AHB substitution at position N1 of designed molecules was used, with the rationale that this group in amikacin is responsible for the protection against a number of aminoglycoside-modifying enzymes that cause N-acylation. Although two of these structures showed considerably enhanced activity against different pathogenic and resistant strains as compared to those of several conventional antibiotics, still their activities were mostly comparable to that of amikacin.

Most recently, Hanessian and co-workers (12g) used a similar approach and tried to mimic rings III and IV of paromomycin by attaching various aminoalkyl substituents at C5 of tobramycin. For their design, they also employed the available NMR and X-ray structural data of the complexes of paromomycin and tobramycin with RNA sequences, as well as molecular modeling. The 5-O-(2-guanidylethyl) ether of tobramycin was found to be the most active analogue of this series, having similar antibacterial potency to that of paromomycin.

During the last decade, more examples of synthetic variants of naturally occurring aminoglycosides have been reported (11). The strategies used in the design of the majority of these mimetics were to start from a pseudo-disaccharide (mostly neamine) as a minimum basic structure and incorporate therein various basic appendages at different positions. The choices of basic appendages, in the cases of rational design, relied on the diversity of pKa, chain length, branching, and flexible topologies. In most cases however, the new analogs were either inactive or had significantly lower activity than that of the parent structure, and only a few new structures reported to date maintained an activity level similar to that of the naturally occurring parent aminoglycosides. Thus, the construction of synthetic molecules providing better antibiotic performances than those of the naturally occurring drugs remains a challenging task.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

The term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

An advantage of the compounds and/or the methods of the present invention is that bifunctional antibiotics are provided, which both inactivate toxins and function as antibiotics.

Another object of the invention is to provide bifunctional antibiotics which reduce or eliminate antibiotic resistance and which further result in reduction of cytoxicity and other side-effects.

Other objects and advantages of the present invention will become apparent from the following description, taken in connection with the accompanying figures and examples, wherein, by way of illustration and example, an embodiment of the present invention is disclosed.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 12 shows the synthesis of some compounds and intermediates according to the present invention;

DETAILED DESCRIPTION OF THE PRESENT INVENTION

Figure 1:
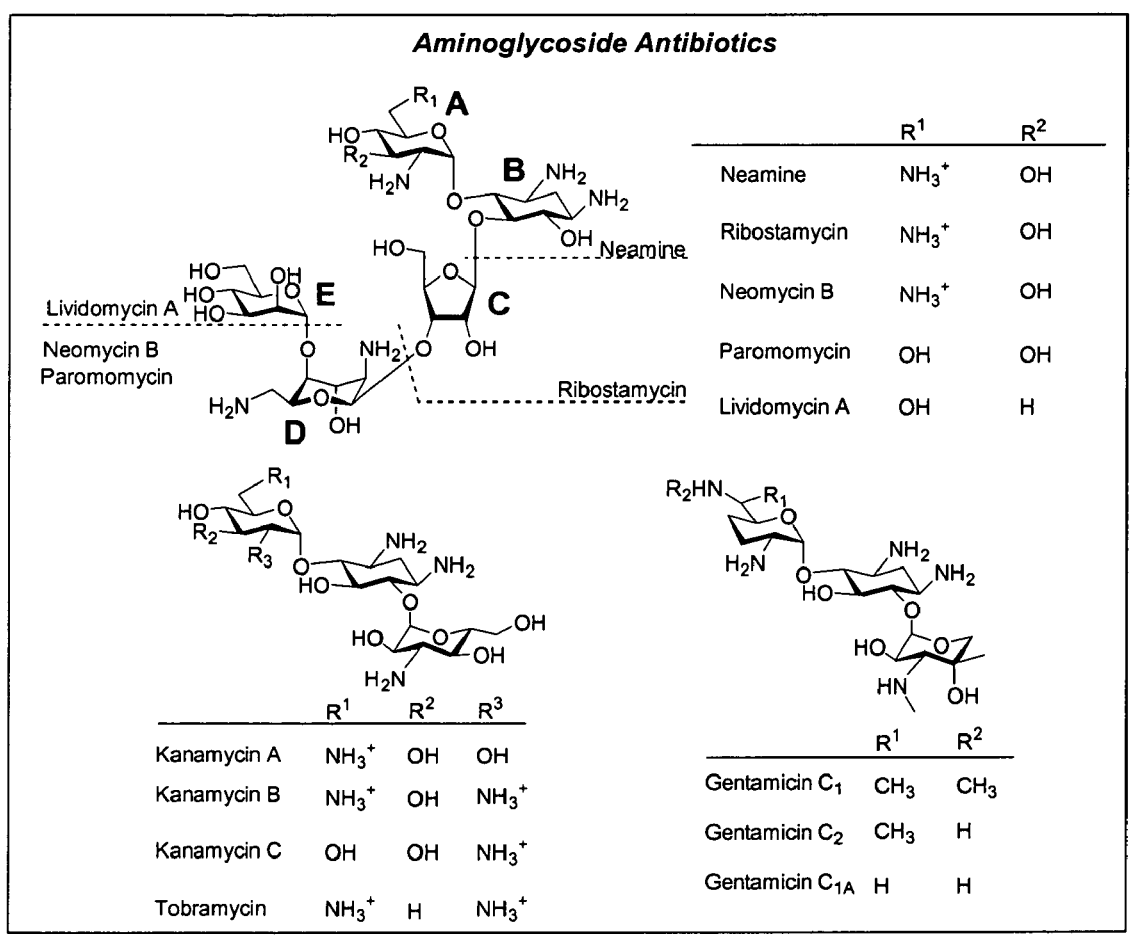
FIG. 1 shows prior art aminoglycosides.
Figure 2:
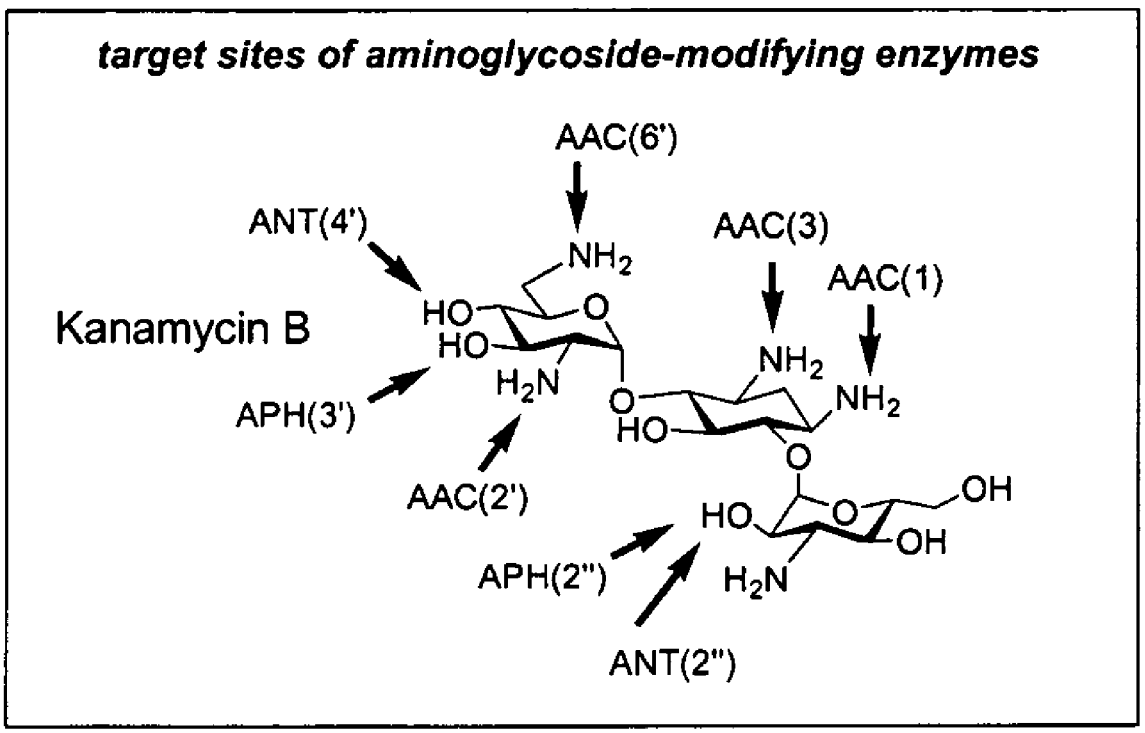
FIG. 2 shows prior art target sites of modifying enzymes.

The present invention is of a novel group of aminoglycosides which share some structural features of currently available aminoglycosides with regard to the backbone, while also having significant structural differences. The similarity enables these aminoglycosides to be effective antibiotics, whilezzz the significant differences enable these aminoglycosides to reduce or even block antibiotic resistance. The aminoglycosides of the present invention are suitable for inhibition of anthrax lethal factor, hence are suitable for use as a cure for anthrax.

The anthrax lethal factor (LF), a Zn-dependent endopeptidase, has a major role in the development and virulence of anthrax. The compounds of the present invention have been found to act as powerful inhibitors of the proteolytic activity of LF at seemingly physiological conditions and simultaneously function as antibiotics against *Bacillus anthracis*.

To find novel inhibitors of LF, a library of approximately 3000 compounds were tested, over 60 of which were synthetic and commercial aminoglycosides (23). While a number of the tested compounds demonstrated some level of inhibitory activity, neomycin B was found to be the most potent inhibitor of LF with apparent $K_i$ value in the low nM concentration range.

The compounds of the present invention were obtained through rational design of antibiotics, based upon known aminoglycosides. However, unlike the previously described rational design strategies, which have many significant drawbacks with regard to the potency and/or side effects of the designed compounds, the compounds of the present invention were designed according to a new and better strategy. Without wishing to be limited by a single hypothesis, it would appear that since aminoglycoside antibiotics, such as neomycin B, exert their antibacterial activity by selectively recognizing and binding to the decoding A site on the 16S subunit of the bacterial rRNA, causing deleterious misreading of the genetic code (24). At physiological pH, aminoglycosides are highly charged and their RNA binding relies on electrostatic interactions (25-26). Examination of the recently determined X-ray crystal structure of LF shows that the active site of the protease also consists of a broad, 40 Å groove with a highly negative electrostatic potential (27).

Docking experiments were performed, which showed that neomycin B could reside within the vicinity of the catalytic zinc, and multiple potential contacts could occur between the negatively charged residues of LF and neomycin B (23).

Based on these data, it was hypothesized that since the interaction of neomycin B with both the rRNA and LF is mainly determined by electrostatic interactions, it is likely that by maintaining the antibiotic backbone intact but adding one or more additional recognition/binding elements, superior binding to both rRNA and LF, and probably better antibacterial performance is expected to result. Enhanced RNA binding by using dimerized aminoglycosides (26), bifunctional aminoglycosides (27), and amino-aminoglycosides (28), along with the inhibition of various nucleic acids metabolizing enzymes by aminoglycosides (29), support this hypothesis.

Figure 16:
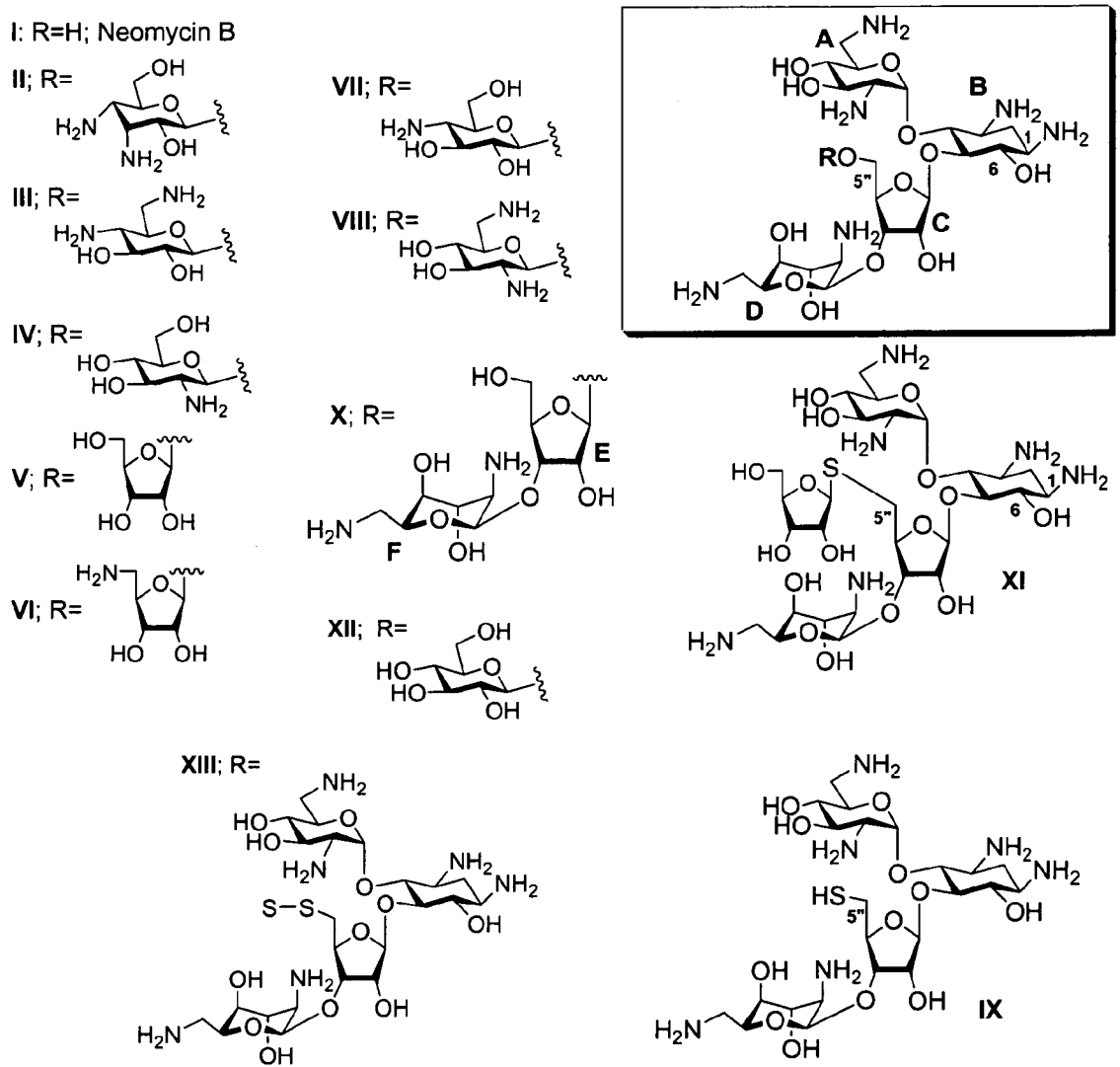
FIG. 16 shows the structures of neomycin B (Compound I) and Compounds II-XIII according to the present invention.

The compounds of FIG. 16 keep the whole antibiotic constitution intact as a recognition element to both the rRNA and LF. The extended sugar ring(s) of each structure was designed in a manner that incorporates different combinations of hydroxyl and amino groups as potential functionalities directed for the recognition of the phosphodiester bond of rRNA (30) and in parallel the Asp/Glu and Asn/Gln clusters in the active site of LF (23).

The principles and operation of the compositions, processes and methods according to the present invention may be better understood with reference to the Examples and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Figure 3:
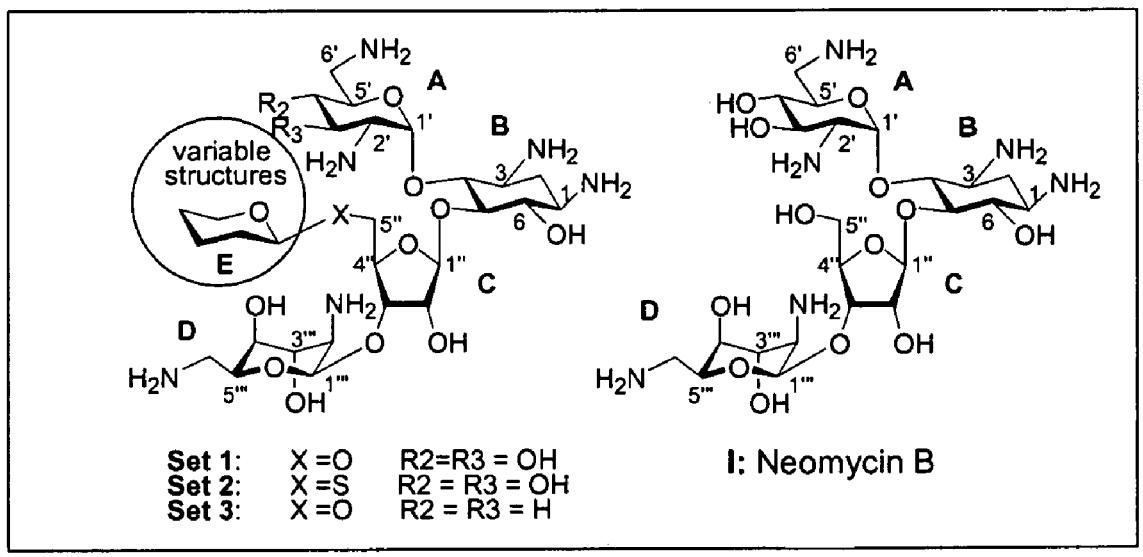
FIG. 3 shows some exemplary structures of compounds according to the present invention.

The compounds of the present invention are based upon neomycin B (Compound I, FIG. 3) as a base structure, with three sets of designed bifunctional mimetics (set1-set3, FIG. 3).

Preferred compounds according to the present invention can be collectively represented by general Formula I:

Formula I wherein:

$R_1$ is a monosaccharide residue or an oligosaccharide residue;

X and Y are independently oxygen or sulfur;

$R_2$ and $R_3$ are each independently selected from the group consisting of hydrogen, hydroxy, thiol, amine, alkyl, cycloalkyl, aryl, alkoxy, aryloxy, thioalkoxy and thioaryloxy, as these terms are defined hereinabove; and wherein the carbon at the fifth position of ring B has an R configuration or an S configuration;

and pharmaceutically acceptable salts thereof.

Preferably X is oxygen. Also preferably, Y is oxygen. Optionally and preferably, $R_1$ is a monosaccharide residue. More preferably, the monosaccharide residue is a five-membered (furanose) or a six-membered (pyranose) monosaccharide residue. Also more preferably, the monosaccharide residue comprises at least one amine group and/or at least one aminoalkyl group. Optionally and more preferably, the at least one amine group and/or the at least one aminoalkyl group is at one or more of positions 2, 3, 4 or 5. As used herein, the term "aminoalkyl" refers to an alkyl group, as defined hereinabove, which is substituted by an amine group, as defined hereinabove. Optionally, at least one aminoalkyl group is an aminomethyl group ($CH_2$—$NH_2$).

Optionally and preferably, if the monosaccharide residue is a pyranose monosaccharide residue, the aminomethyl group is at position 5.

Also optionally and preferably, if the monosaccharide residue is a pyranose monosaccharide residue, the amine group is at one or more of positions 2, 3 or 4.

Also optionally and preferably, if the monosaccharide residue is a furanose monosaccharide residue, the aminoalkyl group is at position 4.

Optionally, the monosaccharide residue is a L-monosaccharide or a D-monosaccharide.

According to preferred embodiments of the present invention, $R_1$ is an oligosaccharide residue. Preferably, the oligosaccharide residue comprises at least two monosaccharide residues, wherein each is independently a five-membered (furanose) or a six-membered (pyranose) monosaccharide residue. More preferably, at least one of the at least two monosaccharide residues comprises at least one amine group and/or at least one aminoalkyl group. Most preferably, the at least one amine group is at position 2 of a pyranose monosaccharide residue. Also most preferably, the at least one aminoalkyl group is at position 5 of a pyranose monosaccharide residue.

Optionally and preferably, the oligosaccharide comprises a furanose monosaccharide linked to a pyranose monosaccharide.

Optionally, each of the at least two monosaccharide residues is independently a D-monosaccharide or a L-monosaccharide.

Optionally, $R_1$ comprises an oligosaccharide residue consisting of at least four monosaccharide residues, whereby each of the monosaccharide residues is a a five-membered (furanose) or a six-membered (pyranose) monosaccharide residue.

Such oligosaccharide residues can be, for example, an aminoglycoside residue such as a Neomycin B residue, a Paromomycin residue, a Ribostamycin residue, a Gentamycin residue, a Amikacin residue, a Neamine residue, a Nebramine residue and a Tobramine residue.

Such oligosaccharide residues preferably further comprise a free chemical group that is coupled to X in Formula I above. Preferably, both X and the chemical group in the oligomers residue are S, such that the olidosacchride residue is coupled via a disulfide bond.

According to other preferred embodiments of the present invention, X is sulfur and $R_1$ is a monosaccharide residue. Preferably, the monosaccharide is a furanose monosaccharide residue.

According to still other preferred embodiments of the present invention, there are provided novel compounds each having the general formula II:

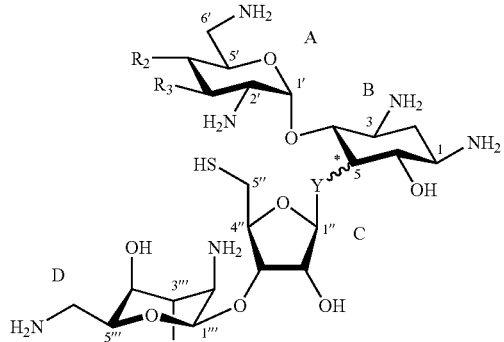

Formula II wherein:

Y is oxygen or sulfur;

$R_2$ and $R_3$ are each independently hydrogen, hydroxy, thiol, amine, alkyl, cycloalkyl, aryl, alkoxy, aryloxy, thioalkoxy and thioaryloxy; and wherein the carbon at the fifth position of ring B has an R configuration or an S configuration;

and pharmaceutically acceptable salts thereof.

Preferably, Y is oxygen, and $R_2$ and $R_3$ are both hydroxy.

According to still other preferred embodiments of the present invention, there are provided novel compounds each having the general formula III:

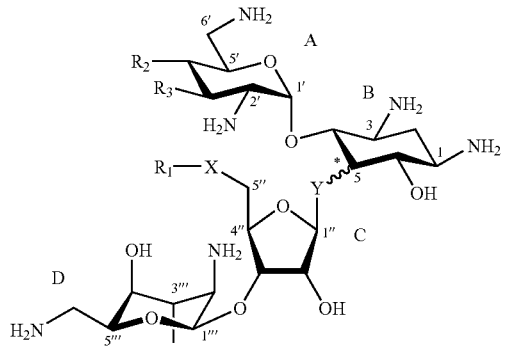

Formula III wherein:

X is disulfide, as defined hereinabove;

Y is oxygen or sulfur;

$R_1$ is an oligosaccharide residue having at least four monosacchride residues, as described hereinabove;

$R_2$ and $R_3$ are each independently hydrogen, hydroxy, thiol, amine, alkyl, cycloalkyl, aryl, alkoxy, aryloxy, thioalkoxy and thioaryloxy, as these terms are defined hereinabove; and wherein the carbon at the fifth position of ring B has an R configuration or an S configuration;

and pharmaceutically acceptable salts thereof.

It should be noted that wherever reference is made to a general formula or a specific compound according to the present invention, pharmaceutically acceptable salts are also optionally included.

All of the different structures of the preferred compounds according to the present invention are shown in FIG. 16.

In selecting the modification site in neomycin B and the degree of modification, recent structural information has been included in the design process, again without wishing to be limited by a single hypothesis, as follows. Superposition of neomycin B bound to the aminoglycoside kinase APH(3') ternary complex with ADP (10), and paromomycin I (contains C6'—OH instead of C6'-$NH_2$ in neomycin B, FIG. 1) bound to A-site bacterial ribosome (25) reveals that all the functional groups of aminoglycosides that are utilized for binding are identical in both antibiotics, with the exception of two groups, which are not employed for binding in the antibiotic-resistance enzyme.

One of these different groups is the C5"-OH of neomycin B which is phased towards the second substrate, ATP, and may have a crucial role for the formation of the reactive ternary complex prior to occurrence of the phosphorylation step. Therefore, without wishing to be limited by a single hypothesis, incorporation of gross changes, such as the addition of extra rigid sugar ring in this region, is expected to have a dramatic effect on the formation of a precise ternary complex required for enzymatic catalysis. For a number of reasons, including the above hypothesis and also ease of synthesis, position C5" in neomycin B was selected as the base for the new generation of pseudo-pentasaccharides of set1 (FIG. 3), with the expectation that they will function better than neomycin B against both the resistant and non-resistant organisms.

Figure 7:
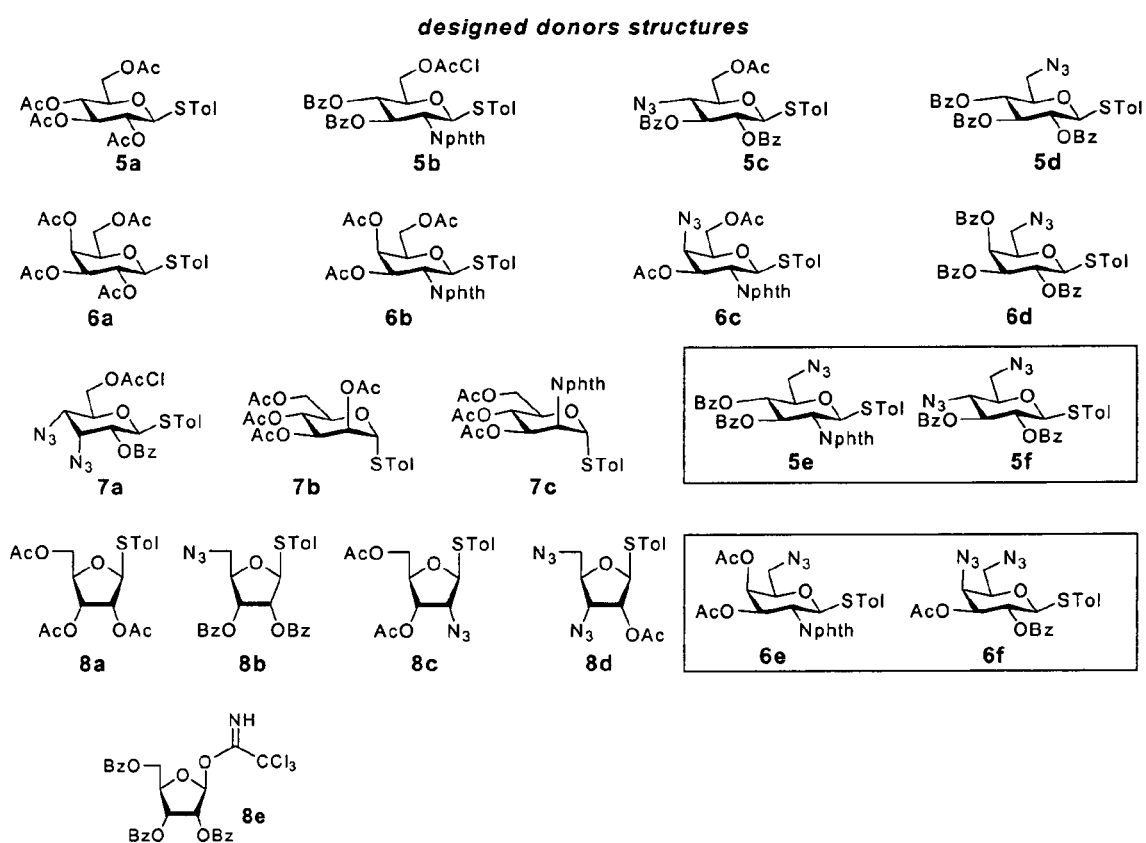
FIG. 7 shows some exemplary donor structures according to the present invention.

These structures maintain the antibiotic backbone intact as a recognition element to the rRNA, while the extended sugar ring ($R_1$) in each structure is designed in a manner that incorporates either plain pyranose sugar, a single amino group at various positions, cis-1,2-diamine, flexible 1,3-diamine, cis-1,3-hydroxyamine, or ribofuranose ring as potential functionalities directed for the recognition of the phosphodiester bond of RNA (29-31) (For the detailed structures at ring $R_1$ see structures of the designed donors in FIG. 7).

The designed structures of set2 (FIG. 3) are similar to that of set1 except for the sulfur atom at C5". These structures were specially designed, again without wishing to be limited by a single hypothesis, to avoid in vivo enzymatic hydrolysis of the added sugars (ring E) by various exoglycosidases (especially in those structures in which ring E contain either plain sugar or 2-aminohexose). The structures of set3 are similar to that of set1 except for the ring A. In the structures of set3, ring A is 3',4'-dideoxy sugar, again without wishing to be limited by a single hypothesis, to combat against the action of various APH(3') enzymes.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLE 1

Figure 4:
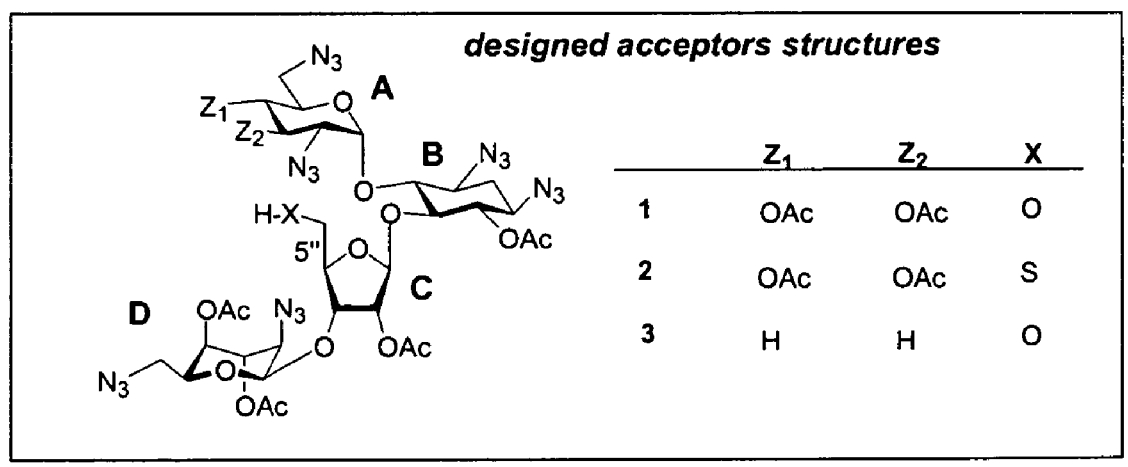
FIG. 4 shows structures of some exemplary designed acceptors according to the present invention.

General Synthesis of the Compounds of the Present Invention and Syntheses of Specific Exemplary Intermediates The strategy for the construction of all three sets of compounds in FIG. 3 featured the use of a common acceptor for each set (acceptors 1-3 in FIG. 4), to which the monosaccharide donors were connected, followed by a two-step deprotection to yield the target C5"-branched derivatives. The protecting groups used in this study served admirably in terms of ease of attachment and removal and survivability under the reaction conditions, whereas the thioglycoside-NIS (31) and trichloroacetimidate-$BF_3$ (32) glycosidation methods proved to be both rapid and efficient.

This Example describes the overall synthetic procedure with optional variations; the following Examples include specific non-limiting examples of the synthetic process as it was performed for the present invention.

Figure 5:
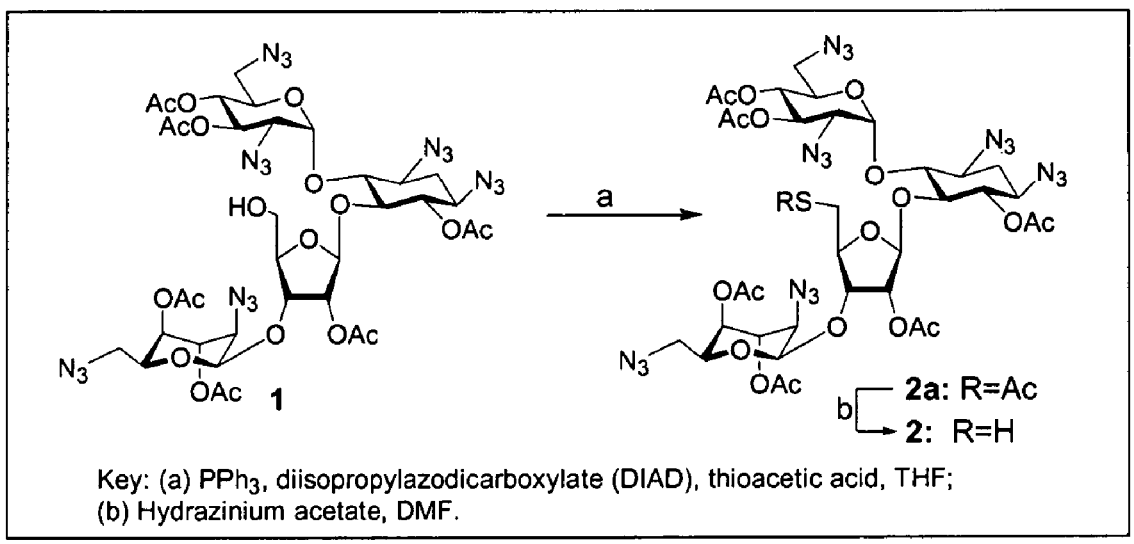
FIG. 5 shows a general outline of a synthetic scheme according to the present invention.

The neomycin acceptor 1 is readily accessible from the commercial neomycin B (49). The C5"-SH acceptor 2 can easily be prepared from the selectively protected hexaazido derivative of neomycin B (acceptor 1) in two steps as outlined in FIG. 5. Briefly, acceptor 2 was prepared as follows: Triphenylphosphine (1.153 grams, 4.4 mmol) was dissolved in dry THF (10 mL) under argon and was stirred at 0° C. for 15 minutes. The mixture was then added dropwise with diisopropylazodicarboxylate (0.627 mL, 4.4 mmol). The mixture was stirred for 45 minutes at 0° C. and a white precipitate of the betaine was observed. In an additional flask acceptor 1 (1.5 gram, 1.467 mmol) and thioacetic acid (0.23 mL, 4.4 mmol) were dissolved in THF (4 mL) under argon, and added dropwise in to the flask containing the betaine. Propagation of the reaction was monitored by TLC (EtOAc 50%, Hexane 50%), which indicated completion after 4.5 hours. The mixture was diluted with EtOAc and washed with brine. The combined organic layer was dried over $MgSO_4$, evaporated and purified by column chromatography (silica, EtOAc/Hexane) to yield the corresponding thioacetate 2a as white solid 1.36 gram (86%).

$^1$H NMR (500 MHz, $CDCl_3$) data of this thioacetate are summarized in Table 12 hereinbelow.

$^{13}$C NMR: δ=20.4, 20.6, 20.7, 20.9, 31.0 (C-2), 31.2 (C-5"), 50.5 (C-6'"), 50.9 (C-6'), 56.6, 57.9, 59.1, 60.6, 65.5, 68.7, 69.1, 69.2, 69.9, 73.1, 74.9, 75.2, 75.7, 77.8, 80.2, 81.4, 96.2 (C-1'), 99.9 (C-1'"), 105.6 (C-1"), 168.5, 169.5, 169.7, 169.9, 170.0, 195.1

ESIMS: m/z=1119.3 ($M+K^+$, $C_{37}H_{48}N_{18}O_{19}S$ requires 1119.5).

The pure thioacetate 2a from the above (250 mg, 0.231 mmol) was dissolved in dry DMF under argon, and added with hydraziniumacetate (42.6 mg, 0.463 mmol). Propagation of the reaction was monitored by TLC (EtOAc 50%, Hexane 50%), which indicated completion after 3 hours. The mixture was diluted with EtOAc and washed with brine. The combined organic layer was dried over $MgSO_4$, evaporated and purified by column chromatography (silica, EtOAc/Hexane) to yield the thiol acceptor 2 as white solid 156 mg (65%).

$^1$H NMR (500 MHz, $CDCl_3$) data of acceptor 2 are summarized in Table 13 hereinbelow.

$^{13}$C NMR: δ=20.4, 20.5, 20.6, 20.7, 26.5 (C-5"), 31.3 (C-2), 50.6 (C-6'"), 50.8 (C-6'), 56.3, 57.9, 59.0, 60.5, 65.5, 68.6, 69.2, 69.7, 73.4, 75.0, 75.3, 75.9, 77.1, 81.3, 81.6, 96.2 (C-1'), 99.0 (C-1'''), 106.3 (C-1''), 168.4, 169.4, 169.6, 169.6, 169.9, 169.9

MALDI-TOFMS: m/z=1077.0 (M+K$^+$, $C_{35}H_{46}N_{18}O_{18}S$ requires 1077.6).

Figure 6:
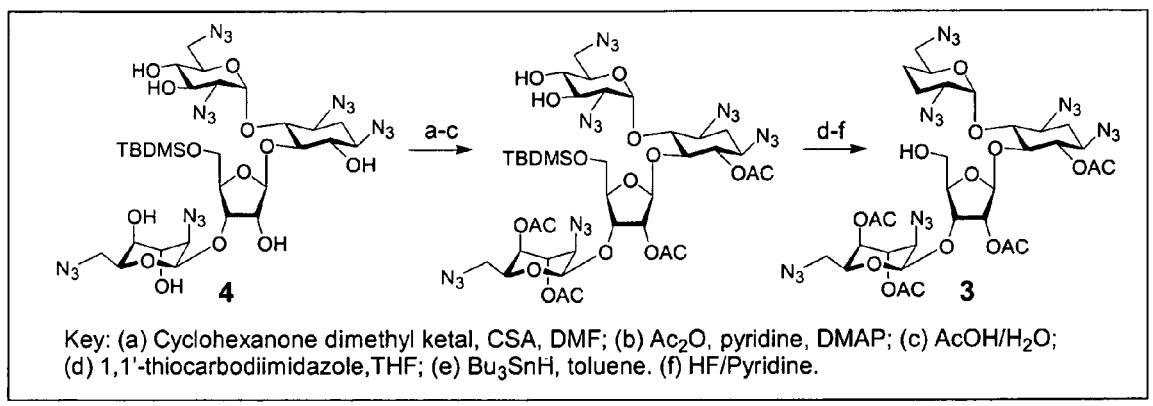
FIG. 6 shows preparation of an acceptor according to the present invention.

The dideoxy acceptor 3 can be prepared from compound 4 (FIG. 6) by selective protection of C3' and C4' hydroxyls by cyclohexylidene, followed by acetylation, selective removal of cyclohexylidene, and two-step simultaneous deoxygenation of C3' and C4' hydroxyls according the reported procedure (32). As an alternative to acetate protection which may not be stable under Bu$_3$SnH treatment, benzyl protection is used.

These newly designed acceptors can be represented by the general formula IV:

Formula IV

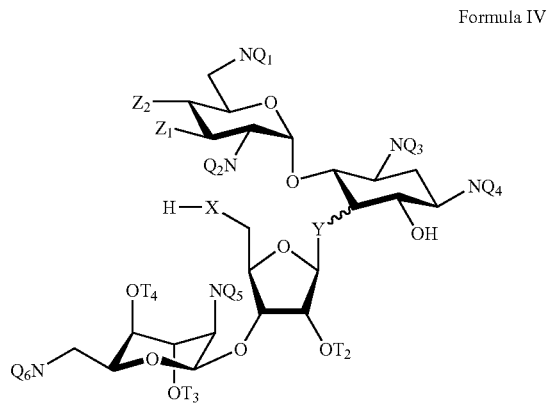

wherein:

each of $Z_1$ and $Z_2$ is independently selected from the group consisting of hydrogen, alkyl, cycloalkyl, aryl, a hydroxy protecting group, an amino protecting group and a thiol protecting group; each of $T_1$-$T_4$ is independently a hydroxy protecting group; each of $Q_1$-$Q_6$ is independently an amino protecting group;

X is oxygen or sulfur; Y is oxygen or sulfur; and wherein the carbon at the fifth position of ring B has an R configuration or an S configuration.

As is exemplified hereinabove, the hydroxy protecting group can be, for example, an O-acetyl group, whereas the amino protecting group can be, for example, an azido group.

As used herein, the phrase "an O-acetyl group" refers to a —O—C(=O)CH$_3$ group, in which the hydroxy group is protected by an acetyl group.

The phrase "an azido group" refers to a —N$_3$ group, in which the amino group is protected by an azo group.

However, other hydroxy and amino protecting groups commonly used in chemical syntheses in general and in saccharide syntheses in particular are also usable in this context of the present invention.

Acceptors 1-3, according to the present invention, are compounds having the general formula IV above, wherein, for acceptor 1, X is oxygen, each of $Z_1$, $Z_2$ and $OT_1$-$OT_4$ is an O-acetyl group and each of $NQ_1$-$NQ_6$ is an azido group; for acceptor 2, X is sulfur, each of $Z_1$, $Z_2$ and $OT_1$-$OT_4$ is an O-acetyl group and each of $NQ_1$-$NQ_6$ is an azido group; and, for acceptor 3, X is oxygen, each of $Z_1$, $Z_2$ is hydrogen, each of $OT_1$-$OT_4$ is an O-acetyl group and each of $NQ_1$-$NQ_6$ is an azido group.

The donors in FIG. 7 were designed as thioglycosides since the thioglycoside-NIS glycosidation method proved to be both rapid and efficient. The N-phth and ester protections at C-2 of the monosaccharide donors were designed to allow, through neighboring group participation, selective β-glycoside bond formation between rings E and C (33-34).

The donors, according to preferred embodiments of the present invention, are therefore compounds having the general formula V, VI or VII:

Formula V

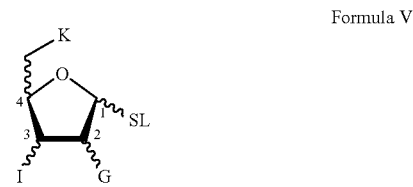

Formula VI

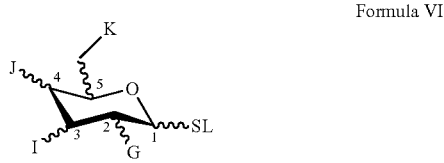

Formula VII

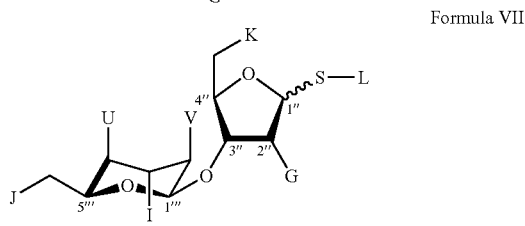

wherein each of G, I, J, K, U and V is independently selected from the group consisting of a hydroxy protecting group (e.g., O-acetyl group, O-chloroacetyl group, and O-benzoyl group) and an amino protecting group (e.g., an azido group and a N-phtalimido group); SL is a thiolated leaving group (e.g., thioethyl and para-thiotoluene); and each of the carbons at positions 1, 3 and 4 in Formula I and at position 1 in Formula II has an R configuration or an S configuration.

The overall synthesis of each of the pseudo-pentasaccharides of the present invention having the general formula I above is therefore effected, according to preferred embodiments of the present invention, by:

(i) providing an acceptor having the general formula IV described hereinabove;

(ii) providing a donor having the general formula V, VI or VII;

(iii) coupling the acceptor and the donor, to thereby provide a protected pseudo-pentasaccharide; and (iv) removing the protecting groups, to thereby provide the desired compound.

Figure 8:
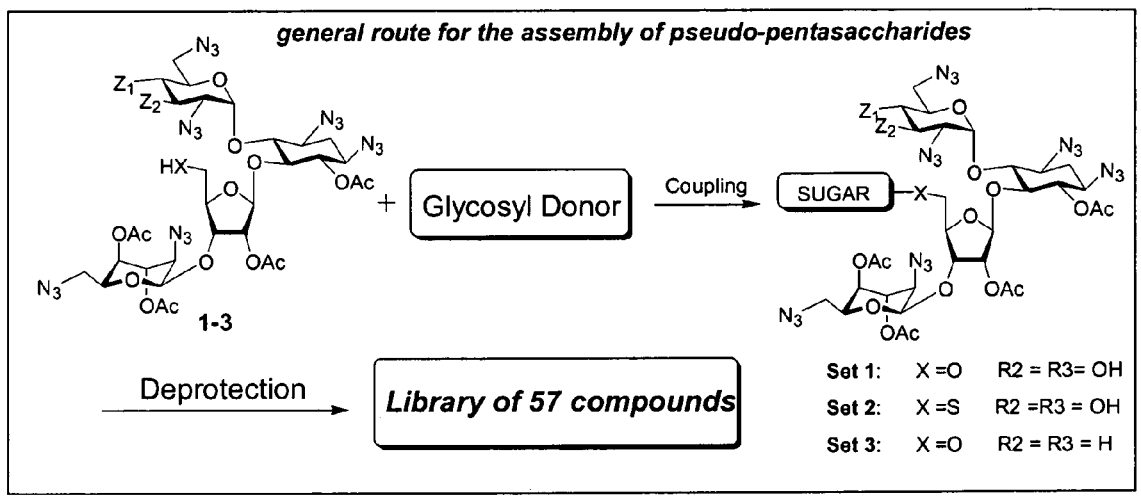
FIG. 8 shows an exemplary synthetic scheme for producing a library of structures.

Preferably, the assembly of the designed protected pseudo-pentasaccharides (set1-set3) is performed by NIS-promoted coupling of each of the acceptors 1-3 with the thioglycoside donors (5a-f, 6a-f, 7a-c, and 8a-d, FIG. 7). The resulting protected compounds are then subjected to a two-step deprotection process: removal of all the ester and phtalimido groups by treatment with methylamine (33% solution in EtOH) and reduction of all the azido groups by Staudinger reaction, to furnish a library of 57 pseudo-pentasaccharide derivatives of neomycin B, as generally illustrated in FIG. 8. Note that for the preparation of set2 structures, the thioglycoside donors are converted to the corresponding trichloroacetimidates and the coupling steps are performed under acidic conditions (BF$_3$.Et$_2$O, CH$_2$Cl$_2$).

The overall synthesis of each of the compounds of the present invention having the general formula II described above is effected, according to preferred embodiments of the present invention, by:

(i) providing an acceptor having the general formula IV, as described hereinabove, wherein X is sulfur; and (ii) removing the protecting groups.

The overall synthesis of each of the compounds of the present invention having the general formula III described above is effected, according to preferred embodiments of the present invention, by:

(a) providing a compound having the general formula IV, as described hereinabove, wherein X is preferably sulfur;

(b) providing an oligosaccharide comprised of at least four monosaccharide residues and having at least one free thiol group attached to at least one of the monosaccharide residues, wherein any hydroxy group or amino group attached to the monosaccharide residues is protected by a hydroxy protecting group or an amino protecting group, respectively;

(c) coupling the compound having general formula IV with the oligosaccharide, to form a disulfide bond therebetween; and (d) removing each of the hydroxy protecting groups and amino protecting groups, to provide the compound of general formula III.

The reacting oligosaccharide can thus be a compound having the general formula IV, such that this synthesis results is a Neomycin B "dimer" in which the two units are linked by a disulfide bond. Alternatively, the reacting oligosaccharide can be, for example, Neamine, Tobramine, Tobramycin, or Gentamycin, which can preferably be modified as described herein with respect to acceptors 1-3 so as to have a free thiol group. The hydroxy or amino protecting groups, present in cases where the oligosaccharide bears hydroxy or amino groups, are as described herein.

Coupling is preferably effected by Lewis acid ($BF_3 \cdot Et_2O$) promoted coupling, which after two-steps deprotection as above provided the desired thioglycoside.

EXAMPLE 2

Selection of Structures for Compounds of the Present Invention

The previous Example related to a general scheme which may optionally be used for any compound according to the present invention, as well as optionally for generating a library of compounds according to the present invention. This Example describes the selection of some non-limiting, illustrative structures for compounds according to the present invention.

One important aspect of the present invention is the use of functional aminoglycosides to solve the problem of cytotoxicity. Without wishing to be limited by a single hypothesis, these structures were selected to ameliorate this problem. One of the major drawbacks of aminoglycosides is their relatively high toxicity. Neomycin B is the most toxic of aminoglycosides, yet it is primarily used for topical infections. It is highly nephrotoxic and ototoxic and is by far the most potent in the area of neuromuscular blockage. Aminoglycosides are nephrotoxic because a small but sizable proportion of the administered dose (about 5%) is retained in the epithelial cells (35). Aminoglycosides accumulated by these cells are mainly localized with endosomal and lysosomal vacuoles but are also localized with the Golgi complex, causing an array of morphological and functional alterations of increasing severity. It is also believed that aminoglycosides cause the formation of free radicals, which lead to cell death (36).

Very recently (37), however, it has been shown that aminoglycosides stabilize DNA and RNA triplexes. A clear correlation between the toxicity ($LD_{50}$ values, the lethal dose, or dose sufficient to kill half the test population) of these antibiotics and their ability to stabilize DNA triple helix was demonstrated and suggested that aminoglycosides may be able to aid H-DNA formation in vivo, which might be one of the reasons for their toxicity. Interestingly, these results also showed that neomycin B, which is most toxic among all aminoglycosides, is also the most active of all aminoglycosides in stabilizing triple helices, and that neomycin B does not influence the double helical structures of DNA structures. Paromomycin (FIG. 1), which differs from neomycin B in that it has one less amino group, is much less toxic than neomycin B ($LD_{50}$ of neomycin=24 mg/kg, paromomycin=160 mg/kg). Thus, this difference of one charge makes a great difference in the toxicity of the two compounds. Further deletion of charged amino groups in ribostamycin makes it least toxic ($LD_{50}$ of ribostamycin=260 mg/kg). On the other hand, lividomycin, which differs from paromomycin by an additional mannose, is much less toxic, with a $LD_{50}$ value of 280 mg/kg. From these data it seems that two factors that significantly reduce the toxicity of aminoglycoside are: reduction of the number of amino groups and/or addition of an extra saccharide.

Figure 9:
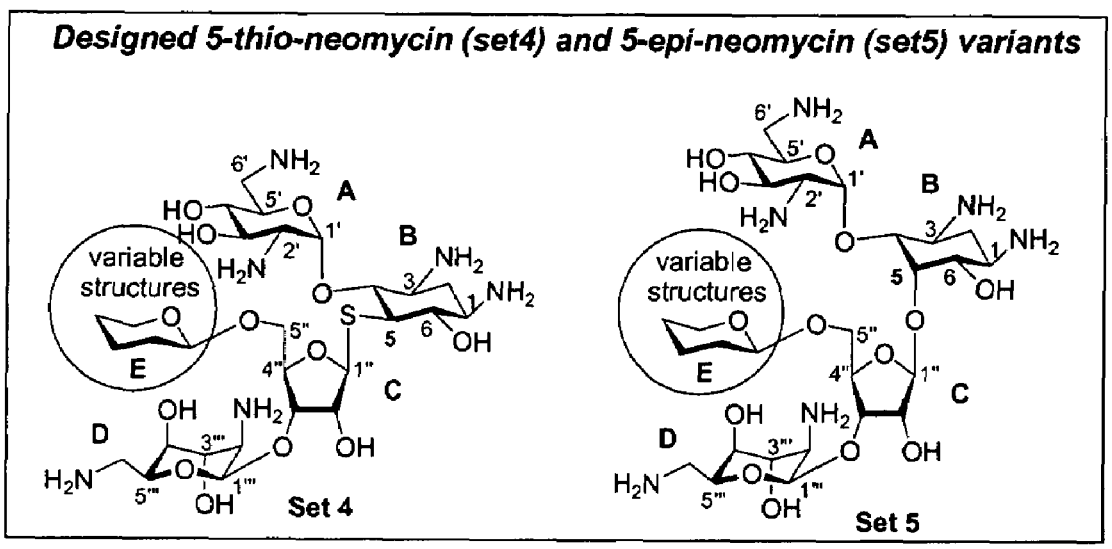
FIG. 9 shows two sets of exemplary neomycin derivatives according to the present invention.

Without wishing to be limited by a single hypothesis, the above features of aminoglycosides and their different levels of cytotoxicity were considered when selecting suitable structures for the compounds of the present invention. Since neomycin B is at the "head of the peak" with lowest $LD_{50}$ value, this structure was selected for designing two sets of derivatives, set4 and set5 (FIG. 9). The rationale in designing set4 structures is to generate new analogs of neomycin B, "thio-neomycins," with superior acid stability, which can lead to a reduction in the required dose for administration and subsequently a lowering of the associated toxicity. The choice of the thioglycosidic linkage between the rings B and C in set4 structures is based on the fact that the glycosidic bond of a furanose is more acid sensitive than that of pyranose. Indeed, this is the reason that neomycin B and all the members of neomycin family suffer a high acid sensitivity. To solve this problem, Chang and co-workers (12f) have recently reported on the new class of "pyranmycins" in which the furanose ring of ribostamycin has been replaced by various pyranose structures. Some of the resulted pseoudo-trisaccharides have indeed showed increased acid stability and substantial antibacterial activity. The suggested production of the "thio-neomycins" is an improved, elegant solution to this problem.

The rationale behind the design of set5 structures is largely based on the recent structural information obtained by Fong and Berghuis (10). This work has shown that while the conformation of aminoglycosides and the functional groups utilized for the binding are effectively identical when comparing the neomycin B-bound structure of APH(3')-IIIa and the paromomycin I-bound structure of the 30S ribosome, there are significant differences when examining the van der Waals interactions. The most striking difference found is that the face of the aminoglycoside that forms most of the van der Waals interactions with APH(3')-IIIa is opposite to that which interacts with the 16S ribosomal RNA.

Without wishing to be limited by a single hypothesis, this observation was used to design novel variant(s) of neomycin B which can interact with the ribosome A-site but which are unable to be detoxified by APH(3')-IIIa and related enzymes.

Examples of these variants according to the present invention include the set5 structures, "epi-neomycins". In these structures, the configuration of neomycin is inverted at C5, which is the branch point between two parts of the molecule, rings A-B and C-D. Such an inversion of configuration in neomycin is expected to result in broad effects. Without wishing to be limited by a single hypothesis, the change of orientation at C5 (from equatorial in neomycin to axial in epi-neomycin) should allow more rotational freedom between rings A and B, and between A-B and C-D. Consequently, but again without wishing to be limited by a single hypothesis, the face of the resulted epi-neomycins is expected to be preferentially recognized by rRNA, while it will be highly hindered for the recognition by aminoglycoside-modifying enzymes. In addition, the resulted conformational changes in set5 structures, relative to neomycin, should affect the stabilization of DNA triple helix and subsequently decrease the toxicity of this set of compounds. Optionally, the two concepts of these structures may be combined to obtain variants of "thio-epi-neomycins."

EXAMPLE 3

Specific Synthesis of Selected Compounds of the Present Invention

Example 1 included a general synthetic scheme which may optionally be used for any compound according to the present invention, as well as optionally for generating a library of compounds according to the present invention. This Example provides an illustrative, non-limiting synthetic process that was performed for selected compounds according to the present invention.

Figure 10:
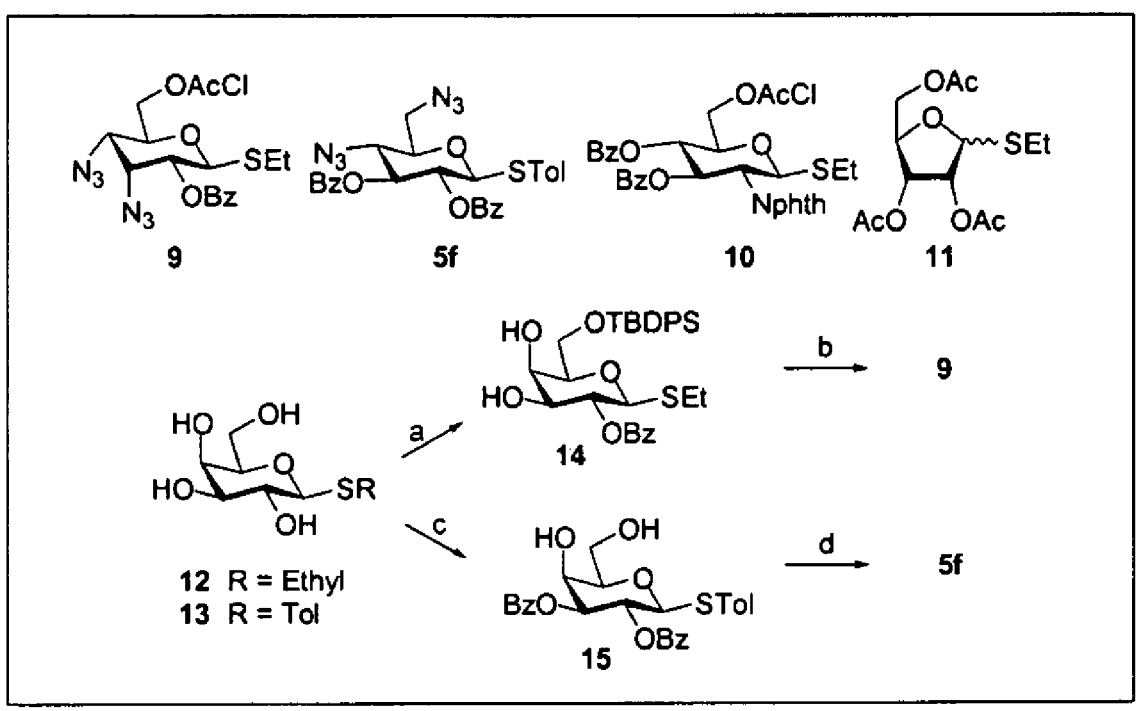
FIG. 10 shows an exemplary synthetic scheme according to the present invention.
Figure 11:
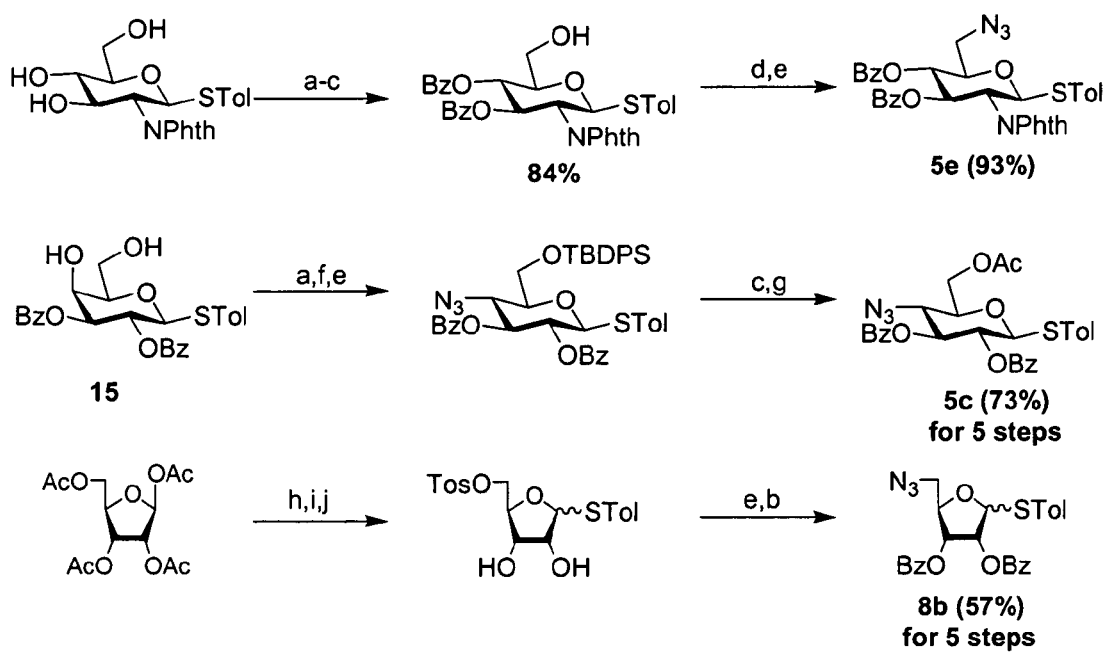
FIG. 11 shows an exemplary synthetic scheme for glycosyl donors 5e, 5c and 8b according to the present invention.

As shown in FIGS. 10-12, a compound was prepared according to a synthetic scheme which started with neomycin B being converted to a general acceptor, as described with regard to Example 1. FIGS. 10 and 11 show the syntheses of the monosaccharide donors. Neomycin B (Compound I) is shown in FIG. 12 after being converted to an acceptor 1 to which the monosaccharide donors of FIG. 7 can be coupled.

The protecting groups used in this study served admirably in terms of the ease of attachment and removal and survivability under the reaction conditions, whereas the thioglycoside-NIS glycosidation method (Veeneman, G. H.; van Leeuwen, S. H.; van Boom, J. H. *Tetrahedron Lett.* 1990, 31, 1331-1334) proved to be both rapid and efficient. The N-phth and ester protections at C-2 of the monosaccharide donors were designed to allow, through neighboring group participation, selective, glycoside bond formation between rings E and C.

For FIG. 10, the following reagents and conditions were used: for stage a, (i) TBDPSCl, pyridine, DMAP, 60° C.; (ii) 2,2-dimethoxypropane, acetone, CSA; (iii) BzCl, pyridine, DMAP; (iv) AcOH/$H_2O$ 9:1, THF, 60° C., 55% for four steps. For stage b, (i) $Tf_2O$, pyridine; (ii) $NaN_3$, DMF, HMPA, 63% for two steps; (iii) HF/pyridine; (iv) ClAcCl, pyridine, 91% for two steps. For stage c, (i) Anisaldehyde-dimethylacetal, CSA, THF; (ii) BzCl, pyridine; (iii) AcOH/$H_2O$ 9:1, THF, 60° C., 58% for three steps. For stage d, (i) $Tf_2O$, pyridine; (ii) $NaN_3$, DMF, HMPA, 86% for two steps.

As a general note for all procedures described herein (unless otherwise noted), reactions were monitored by TLC on Silica Gel 60 F254 (0.25 mm, Merck), and spots were visualized by charring with a yellow solution containing $(NH_4)Mo_7O_{24}\cdot4H_2O$ (120 grams) and $(NH_4)_2Ce(NO_3)_6$ (5 grams) in 10% $H_2SO_4$ (800 mL). Flash column chromatography was performed on Silica Gel 60 (70-230 mesh). All reactions were carried out under an argon atmosphere with anhydrous solvents, unless otherwise noted. All chemicals unless otherwise stated, were obtained from commercial sources.

The diazido monosaccharides 9 and 5f, having D-allo and D-gluco configurations, respectively, were constructed from the common D-galactose derivatives (FIG. 10) by selectively inverting the configurations at C3 and C4 (in 9) and at C4 (in 5f). Briefly, the diol 14 was prepared from the known thioglycoside 12 (Pozsgay, V.; Jennings, H. J. *Tetrahedron Lett.* 1987, 28, 1375-1376) in four steps (selective silylation of the primary hydroxyl, acetonide formation at C3-OH and C4-OH, benzoylation, and removal of the acetonide) without isolation of intermediate products in an overall yield of 55%.

More specifically, ethyl 2-O-benzoyl-6-O-tert-butyldiphenylsilyl-1-thio-β-D-galactopyranoside (compound 14) was prepared from ethyl 2,3,4,6-tetra-O-acetyl-1-thio-β-D-galactopyranoside (Pozsgay, V.; Jennings, H. J. *Tetrahedron Lett.* 1987, 28, 1375-1376), by using the following five steps procedure.

To a suspension of ethyl 2,3,4,6-tetra-O-acetyl-1-thio-β-D-galactopyranoside (6.25 grams, 16 mmol) in dry MeOH (70 mL) and dry dichloromethane (70 mL) was added catalytic amount of NaOMe (0.5M solution in MeOH) at 0° C. Propagation of the reaction was monitored by TLC (MeOH 10%, dichloromethane 90%). After 2 hours the reaction mixture was neutralized by Dowex H+ and evaporated to dryness. The resultant crude preparation of 12 (3.2 grams, 14.3 mmol) was used for the next step without further purification.

The crude of 12 from the previous step (3.2 grams, 14.3 mmol) in dry pyridine (35 mL) was added with a catalytic amount of DMAP and stirred under argon at 60° C. for 10 minutes. The mixture was added with tert-butyldiphenylsilyl-chloride (6.7 mL, 25.7 mmol) and the reaction progress was monitored by TLC (EtOAc 65%, Hexane 35%). After 30 minutes the mixture was diluted with EtOAc and washed with brine, 1.5% $H_2SO_4$, $NaHCO_3$ (saturated), and finally with brine. The organic layer was dried over $MgSO_4$ and evaporated to give a pale yellow syrup (8.2 grams) that was used for the next step without further purification.

The crude from the previous step (8.2 grams) in acetone (50 mL) and 2,2-dimethoxypropane (25 mL) was stirred at ambient temperature for 5 minutes and then added with a catalytic amount of camphorsulfonic acid. Propagation of the reaction was monitored by TLC (EtOAc 30%, Hexane 70%). After 3 hours the reaction mixture was neutralized by $NH_4OH$ (2.5%) and evaporated to dryness. The crude was diluted with EtOAc and washed with brine. The combined organic layer was dried over $MgSO_4$ and evaporated to give a pale yellow syrup (8.7 grams).

The crude from the previous step (8.7 grams) was added with a catalytic amount of DMAP in dry pyridine (50 mL) and stirred at ambient temperature for 5 minutes. The reaction mixture was added with benzoylchloride (4.14 mL, 35.7 mmol) and the propagation of the reaction was monitored by TLC ($Et_2O$ 20 percentages, Hexane 80%). After 4 hours the mixture was diluted with EtOAc and the organic phase was washed as follows: brine, HCl (2%), $NaHCO_3$ (sat.) and brine. The combined organic layer was then dried over $MgSO_4$ and evaporated to give a pale yellow syrup (9.3 grams).

The crude from the previous step (9.3 grams) was dissolved in THF (10 mL), AcOH (50 mL) and water (5 mL). The reaction mixture was stirred at 60° C. for 5 hours. Propagation of the reaction was monitored by TLC (EtOAc 30%, Hexane 70%). The reaction mixture was diluted with EtOAc and the organic phase was neutralized with $NaHCO_3$ (sat.), and washed with brine. The combined organic layer was dried over MgSO$_4$, evaporated and purified by flash chromatography (silica, EtOAc/Hexane) to yield compound 14 as pale-yellow syrup (4.34 grams, 48% yield for the five steps).

$^1$H NMR (500 MHz, CDCl$_3$): δ=1.05 (s, 9H, t-Bu), 1.25 (t, 3H, J=7.5 Hz, SCH$_2$CH$_3$), 2.68 (m, 2H, SCH$_2$CH$_3$), 3.59 (m, 1H, H-5), 3.76 (dd, 1H, J$_1$=3, J$_2$=9.5 Hz, H-3), 3.97 (m, 2H, H'-6, H-6), 4.14 (d, 1H, J=2.18 Hz, H-4), 5.01 (d, 1H, J=10 Hz, H-1), 5.14 (t, 1H, J=9, Hz, H-2), 7.38-8.12 (m, 15H, aromatic).

$^{13}$C NMR (125 MHz, CDCl$_3$): δ=26.8 (C(CH$_3$)$_3$), 63.7 (C-6), 69.7 (C-4), 72.2 (C-2), 74.2 (C-3), 78.0 (C-5), 80.1 (C-1), 127.6, 127.7, 128.6, 129.7, 129.8, 130.1, 133.7, 135.6, 135.8.

ESIMS: m/z=605.1 (M+K$^+$ C$_{31}$H$_{38}$O$_6$SSi requires 605.3).

Simultaneous triflation of both hydroxyls in 14 was followed by nucleophilic displacement with azide (without isolation of the intermediate ditriflate) to afford the corresponding diazide (63% isolated yield for two steps). Desilylation was then followed with a chloracetylation step to produce the allo-donor 9. Ethyl 2-O-Benzoyl-3,4-dideoxy-3,4-diazido-6-O-chloroacetyl-1-thio-β-D-allopyranoside (compound 9) was prepared as follows. Compound 14 (1.68 gram, 2.97 mmol) was dissolved in dichloromethane (8 mL) and pyridine (0.73 mL, 7.4 mmol), and was stirred at 0° C. for 10 minutes. To this mixture was added Tf$_2$O (1.08 mL, 6.4 mmol) and the propagation of the reaction was monitored by TLC (EtOAc 20%, Hexane 80%), which indicated completion after 15 minutes. In an additional flask a mixture of NaN$_3$ (3.795 grams, 58.3 mmol), dry DMF, (40 mL) and HMPA (5 mL) was vigorously stirred under argon, and added at once in to the reaction mixture. The reaction was heated to 50° C., and propagation was monitored by TLC (EtOAc 20%, Hexane 80%). After 3 hours the mixture was diluted with EtOAc and washed with brine, HCl (2%), NaHCO$_3$ (sat.), brine. The combined organic layer was dried over MgSO$_4$, evaporated and purified by flash chromatography (silica, Diethylether/Hexane) to yield the corresponding 3,4-diazido product as a pale yellow syrup (1.15 gram, 63%).

$^1$H NMR (500 MHz, CDCl$_3$): δ=1.07 (s, 9H, t-Bu), 1.24 (t, 3H, J=9.5, SCH$_2$CH$_3$), 2.68 (m, 2H, SCH$_2$CH$_3$), 3.73 (broad d, 1H, J=9.5, Hz, H-5), 3.88 (dd, 1H, J$_1$=3.0, J$_2$=12.0 Hz, H-6), 3.97 (d, 1H, J=11.5 Hz, H-6'), 4.51 (dd, 1H, J$_1$=3.0, J$_2$=6.0 Hz, H-3), 4.06 (dd, 1H, J$_1$=3.0, J$_2$=9.5 Hz, H-4), 4.95 (d, 1H, J=9.5 Hz, H-1), 5.19 (dd, 1H, J$_1$=3.0, J$_2$=10, H-2), 7.38-8.11 (m, 15H, aromatic).

$^{13}$C NMR (125 MHz, CDCl$_3$): δ=26.8 (C(CH$_3$)$_3$), 57.7 (C-4), 63.0 (C-6), 63.1 (C-3), 70.2 (C-2), 75.7 (C-5), 79.6 (C-1), 127.6, 127.7, 128.6, 129.7, 129.8, 130.1, 133.7, 135.6, 135.8.

ESIMS: m/z=655.2 (M+K$^+$ C$_{31}$H$_{36}$N$_6$O$_4$SSi requires 655.3).

The di-azido product (1.15 gram, 1.87 mmol) was dissolved in pyridine (4 mL) and stirred in a polyethylene vessel at 0° C. for 10 minutes. The mixture was added with HF/Pyr (4 mL) and its propagation was monitored by TLC (EtOAc 20%, Hexane 80%). After 5 minutes the mixture was diluted with EtOAc and neutralized with NaHCO$_3$ (sat.). The combined organic layer was dried over MgSO$_4$ and evaporated to dryness. The residue was dissolved in pyridine (10 mL) and added with a catalytic amount of DMAP, followed by the addition of chloroacetylchloride (0.286 mL, 3.73 mmol). Propagation was monitored by TLC (EtOAc 20%, Hexane 80%). After 25 minutes the mixture was diluted with EtOAc, washed with brine, HCl (2%), NaHCO$_3$ (sat.), and brine. The combined organic layer was dried over MgSO$_4$, evaporated and purified by flash chromatography (silica, EtOAc/Hexane) to yield the titled compound 9 as a pale yellow syrup (777 mg, 91%).

$^1$H NMR (500 MHz, CDCl$_3$): δ=1.23 (t, 3H, J=10.0, SCH$_2$CH$_3$), 2.68 (m, 2H, SCH$_2$CH$_3$), 3.73 (dd, 1H, J$_1$=3.0, J$_2$=10.0 Hz, H-4), 3.94 (ddd 1H, J$_1$=2.5, J$_2$=4.5, 1H, J$_3$=10.0 Hz, H-5), 4.1 (s, 2H, COCH$_2$Cl) 4.29 (dd, 1H, J$_1$=5, J$_2$=12.5 Hz, H-6), 4.51 (m, 2H, H-3, H-6), 4.97 (d, 1H, J=10 Hz, H-1), 5.16 (dd, 1H, J$_1$=3.5, J$_2$=10.0 Hz, H-2), 7.44-8.08 (5H, aromatic).

$^{13}$C NMR (125 MHz, CDCl$_3$): δ=15 (SCH$_2$CH$_3$), 24.2 (SCH$_2$CH$_3$), 40.6 (COCH$_2$Cl), 58 (C-4), 62.5 (C-3), 64.7 (C-6), 70.0 (C-2), 72.6 (C-5), 80.4 (C-1), 127.6, 127.7, 128.6, 129.7, 129.8, 130.1, 133.7, 135.6, 135.8.

ESIMS: m/z=493.5 (M+K$^+$ C$_{17}$ClH$_{19}$N$_6$O$_5$S requires 493.6).

Alternatively, selective protection of C6 and C4 hydroxyls in the galactoside 13 by p-methoxybenzylidene, followed by benzoylation and hydrolysis of the benzylidene, gave the diol 15 in an overall 58% yield for three steps.

p-Methylphenyl 2,3-Di-O-benzoyl-1-thio-β-D-galactopyranoside (compound 15) was prepared as follows: To a solution of p-methylphenyl-1-thio-β-D-galactopyranoside (Zhang, Z.; Ollmann, I. R.; Ye, X-S.; Wischnat, R.; Baasov, T.; Wong, C-H. *J. Am. Chem. Soc.,* 1999, 121, 734) (4.7 g, 16 mmol) in DMF (30 mL) and anisaldehyde dimethylacetal (3.6 mL, 21 mmol) was added a catalytic amount of camphorsulfonic acid and stirred at ambient temperature. The reaction was monitored by TLC (EtOAc 70%, Hexane 30%). After 2 hours the mixture was diluted with EtOAc, and washed with brine, NaHCO$_3$ (sat.), and once again with brine. The combined organic layer was dried over MgSO$_4$, evaporated and purified by flash chromatography (silica, EtOAc/Hexane) to yield the corresponding 4,6-O-benzylidene (4.9 grams, 76%).

$^1$H NMR (125 MHz, CDCl$_3$): δ=2.47 (s, 3H, Me-STol), 3.62 (broad s, 1H, Hz, H-5), 3.75 (dd 1H, J$_1$=J$_2$=9.5 Hz, H-2), 3.79 (dd, 1H, J$_1$=3, J$_2$=9.5 Hz, H-3), 3.92 (s, 3H, Me-OMP), 4.10 (d, 1H, J=11.5 Hz, H-6), 4.28 (d, 1H, J=3 Hz, H-4) 4.45 (d, 1H, J=11.5 Hz, H-6'), 4.10 (d, 1H, J=9.5 Hz, H-1), 5.55 (s, 1H, Benzylic Proton), 6.96-7.70 (m, 8H, aromatic).

$^{13}$C NMR (125 MHz, CDCl$_3$): δ=21.2 (Me-STol), 55.2 (Me-OMP), 68.6, 69.2, 69.9, 73.7, 75.3, 87, 101.1 (C-1), 113.4, 127.8, 129.6, 131.9, 132.1, 134.2, 138.3.

Positive CIMS: m/z=405.1 (M+H$^+$ C$_{21}$H$_{24}$O$_6$S requires 404.2).

The product from the previous step (4.9 grams, 12.2 mmol) was dissolved in dry pyridine under argon and added with a catalytic amount of DMAP. After being stirred at ambient temperature for 5 minutes, the reaction mixture was added with benzoylchloride (3.7 mL, 31.4 mmol). Propagation of the reaction was monitored by TLC (EtOAc 30%, Hexane 70%), which indicated completion after 4 hours. The reaction mixture was diluted with EtOAc and the organic phase was washed as follows: brine, HCl (2%), NaHCO$_3$ (sat.), brine. The combined organic layer was dried over MgSO$_4$, and evaporated to dryness to yield 6.3 grams of crude that was used for the next step without further purification.

The crude from the previous step (6.3 grams) was added with THF (10 mL), AcOH (50 mL), and water (5 mL). The reaction mixture was stirred at 50° C. for 3 hours. Propagation of the reaction was monitored by TLC (EtOAc 30%, Hexane 70%). The reaction mixture was diluted with EtOAc and the organic phase was neutralized by NaHCO$_3$ (sat.), and washed with brine. The combined organic layer was dried over MgSO$_4$, evaporated and purified by flash chromatography (silica, EtOAc/Hexane) to yield compound 15 (4.62 grams, 58% for the three steps).

$^1$H NMR (500 MHz, CDCl$_3$/CD$_3$OD 10/1): δ=2.21 (s, 3H, Me-STol), 3.50-3.90 (m, 3H, H-5, H-6, H-6'), 4.27 (d, 1H, J=3.5 Hz, H-4), 4.80 (d, 1H, J=9.9 Hz, H-1), 5.17 (dd, 1H, J$_1$=4.5, J$_2$=9.9 Hz, H-3), 5.64 (t, 1H, J=4.2 Hz, H-2) 6.98-7.90 (m, 14H, aromatic).

$^{13}$C NMR (125 MHz, CDCl$_3$): δ=20.9 (Me-STol), 61.4, 67.3, 68.2, 75.6, 78.5, 87.2 (C-1), 128.2, 128.8, 129.3, 129.6, 132.6, 133.1, 133.2, 138.1, 165.5, 166.0.

Negative CIMS: m/z=494.3 (M+H$^+$ C$_{26}$H$_{20}$O$_7$S requires 495.3).

This diol (compound 15) was then subjected to a similar triflation and azidation steps as for compound 14 to afford the 4,6-diazido donor 5f in an isolated yield of 86% for two steps.

p-Methylphenyl-4,6-Dideoxy-4,6-diazido-2,3-O-benzoyl-1-thio-β-D-glucopyranoside (compound 5f) was prepared as follows. Compound 15 (4.62 grams, 9.35 mmol) in dry pyridine (20 mL) was stirred under argon at 0° C. for 10 minutes and added with Tf$_2$O (1.97 mL, 11.7 mmol). The mixture was allowed to warm to room temperature. Propagation of the reaction was monitored by TLC (EtOAc 20%, Hexane 80%), which indicated completion after 15 minutes. In an additional flask, a mixture of NaN$_3$ (12.17 grams, 187 mmol) in dry DMF, (40 mL) and HMPA (5 mL) was vigorously stirred under argon, and added at once into the reaction mixture. Propagation was monitored by TLC (EtOAc 20%, Hexane 80%), which indicated completion after 3 hours. The mixture was diluted with EtOAc and washed with brine, HCl (2%), NaHCO$_3$ (sat.), and brine. The combined organic layer was dried over MgSO$_4$, evaporated and purified by flash chromatography (silica, EtOAc/Hexane) to yield compound 5f (3.66 grams, 72 percentages yield).

$^1$H NMR (500 MHz, CDCl$_3$): δ=2.33 (s, 3H, Me-STol), 3.51 (dd, 1H, J$_1$=4.5, J$_2$=13.5 Hz, H-6), 3.56 (ddd 1H, J$_1$=1.5, J$_2$=4.5, 1H, J$_3$=15.0 Hz, H-5), 3.70 (dd, 1H, J$_1$=1.5, J$_2$=13.0 Hz, H-6'), 3.83 (t, 1H, J=9.5 Hz, H-4), 4.82 (d, 1H, J=10.0 Hz, H-1), 5.26 (t, 1H, J=9.5 Hz, H-2), 5.61 (d, 1H, J=9.5 Hz, H-3), 7.10-7.95 (m, 14H, aromatic).

$^{13}$C NMR (125 MHz, CDCl$_3$): δ=21.2 (Me-STol), 51.5 (C-6), 60.5 (C-4), 70.1 (C-2), 74.9 (C-3), 77.4 (C-5), 86.1 (C-1), 126.6, 128.4, 128.5, 129.0, 129.7, 129.8, 133.4, 133.5, 134.6, 134.7, 139.1, 165.0, 165.6.

ESIMS: m/z=583.1 (M+K$^+$ C$_{27}$H$_{24}$O$_5$N$_6$S requires 583.3).

Ethyl 3,4-Di-O-benzoyl-6-O-chloroacetyl-2-deoxy-2-phthalimido-1-thio-β-D-glucopyranose (compound 10) was prepared by the same synthetic path which was used for the preparation of phenyl 6-O-acetyl-3,5-di-O-benzoyl-2-deoxy-2-phthalimido-1-thio-β-D-glucopyranose (Solomon, D.; Fridman, M.; Zhang, J.; Baasov, T. *Organic Letters* 2001, 3, 4311-4314).

Ethyl 2,3,5-Tri-O-acetyl-1-thio-D-ribofuranose (compound 11) was prepared as follows. The commercial 1,2,3,5-tetra-O-acetyl-β-D-ribofuranose (3.5 grams, 11 mmol) in dichloromethane (30 mL) was added with ethylthiotrimethylsilane (4.44 mL, 27.5 mmol) and TMSOTf (2 mL, 11 mmol). The mixture was stirred at ambient temperature and the reaction progress was monitored by TLC (EtOAc/Hexane 1:1), which indicated completion after 3.5 hours. The mixture was diluted by EtOAc (200 mL), neutralized by NaHCO$_3$ (sat.), and washed with brine. The combined organic layer was dried over MgSO$_4$, evaporated and purified by flash chromatography (silica, EtOAc/Hexane) to yield compound 11 3.4 grams, (96% yield) as a mixture of anomers (α/β; 1:3).

$^1$H NMR (500 MHz, CDCl$_3$) for 9-α-anomer: δ=4.07 (dd, 1H, J$_1$=4.0, J$_2$=11.5 Hz, H-5), 4.17 (dd, 1H, J$_1$=4.0, J$_2$=9.5 Hz, H-4), 4.28 (dd, 1H, J$_1$=3.0, J$_2$=12.0 Hz, H-5), 5.09 (d, 1H, J$_1$=3.0 Hz, H-1), 5.16 (dd, 1H, J$_1$=J$_2$=5.0 Hz, H-2), 5.26 (dd, 1H, J$_1$=J$_2$=5.5 Hz, H-3).

$^{13}$C NMR (125 MHz, CDCl$_3$): δ=14.7, 20.37, 20.4, 20.7, 24.5, 63.5 (C-5), 71.6, 74.4, 79.5, 85.5 (C-1), 169.4, 169.5, 170.3.

$^1$H NMR (500 MHz, CDCl$_3$) for 9-β-anomer: δ=4.12 (dd, 1H, J$_1$3.5, J$_2$=12.0 Hz, H-5), 4.25 (dd, 1H, J$_1$=3.5, J$_2$=12.0 Hz, H-5'), 4.27 (dd, 1H, J$_1$=4.0, J$_2$=8.0 Hz, H-4), 5.08 (t, 1H, J=6.0 Hz, H-3), 5.30 (d, 1H, J=6.5 Hz, H-2), 5.53 (d, 1H, J=4.5 Hz, H-1). $^{13}$C NMR (125 MHz, CDCl$_3$), 14.9, 20.3, 20.4, 20.6, 25.3, 62.8 (C-5), 70.4, 71.3, 74.4, 86.7 (C-1), 169.3, 169.7, 170.4.

$^{13}$C NMR (125 MHz, CDCl$_3$): δ=21.2 (Me-STol), 51.5 (C-6), 60.5 (C-4), 70.1 (C-2), 74.9 (C-3), 77.4 (C-5), 86.1 (C-1), 126.6, 128.4, 128.5, 129.0, 129.7, 129.8, 133.4, 133.5, 134.6, 134.7, 139.1, 165.0, 165.6.

Negative CIMS: m/z=319.1 (M–H$^+$ C$_{13}$H$_{20}$O$_7$S requires 320.1).

p-Methylphenyl-2-deoxy-2-phthalimido-6-deoxy-6-azido-3,4-di-O-benzoyl-1-thio-β-D-glucopyranoside (5e) was prepared from p-Methylphenyl-2-deoxy-2-phthalimido-1-thio-β-D-glucopyranoside (Wong, Chi-Huey; Zhang, Zhiyuan; Ollmann, Ian; Baasov, Timor; Ye, Xin-Shan, *J. Am. Chem. Soc*, 1999, 121, 734-753), by the following four steps:

p-Methylphenyl-2-deoxy-2-phthalimido-1-thio-β-D-glucopyranoside (2 grams, 4.8 mmol) in dry pyridine (35 mL), was added with a catalytic amount of DMAP and stirred under argon at 60° C. for 10 minutes. The mixture was added with tert-butyldiphenylsilylchloride (2.51 mL, 9.63 mmol) and the reaction progress was monitored by TLC (EtOAc 65%, Hexane 35%). After 2 hours the mixture was allowed to cool back to room temperature, and added with benzoyl chloride (1.67 mL, 14.45 mmol) and the propagation of the reaction was monitored by TLC (EtOAc 40%, Hexane 60%). After 4 hours the mixture was diluted with EtOAc and the organic phase was washed as follows: brine, HCl (2%), NaHCO$_3$ (sat.) and brine. The combined organic layer was then dried over MgSO$_4$ and evaporated to afford a pale yellow syrup.

The crude from the previous step was dissolved in pyridine (15 mL) and stirred under argon at 0° C. for 10 minutes in a polyethylene vessel. The mixture was added with HF/Pyr (15 mL) and its propagation was monitored by TLC (EtOAc 20%, Hexane 80%). After 5 minutes the mixture was diluted with EtOAc and neutralized with NaHCO$_3$ (sat.). The combined organic layer was dried over MgSO$_4$, evaporated to dryness and purified by flash chromatography (silica, EtOAc/Hexane) to yield the titled compound as 2.52 grams (84% for the 3 steps).

$^1$H NMR (200 MHz): δ=1.63 (broad s, 1H, 6-OH), 2.31 (s, 3H, SPhCH$_3$), 3.69 (dd, 1H, J$_1$=4.7, J$_2$=12.7 Hz, H-6), 3.82-3.93 (m, 2H, H-5, H-6'), 4.54 (t, 1H, J=10.4 Hz, H-2), 5.46 (t, 1H, J=9.8 Hz, H-4), 5.81 (d, 1H, J=10.6 Hz, H-1), 6.28 (t, 1H, J=10.2, Hz, H-3), 6.91-7.92 (m, 18H, aromatic).

Positive CIMS: m/z=623.3 (M$^+$ C$_{35}$H$_{29}$NO$_8$S requires 623.1).

The pure alcohol from the above (1.5 gram, 2.4 mmol) was dissolved in pyridine (30 mL), and was stirred at 50° C. for 10 minutes followed by the addition of freshly crystallized p-toluenesulfonyl chloride (1.15 gram, 6.01 mmol). Propagation of the reaction was monitored by TLC (EtOAc 20%, Hexane 80%), which indicated completion after 15 minutes. The mixture was diluted with EtOAc and the organic phase was washed as follows: brine, HCl (2%), NaHCO$_3$ (sat.) and again with brine. The combined organic layer was then dried over MgSO$_4$ and evaporated to afford a pale yellow syrup. The tosylation product was then put under argon and added NaN$_3$ (1.562 gram, 24 mmol), dry DMF (40 mL) and HMPA (5 mL). The reaction was heated to 50° C., and propagation was monitored by TLC (EtOAc 20%, Hexane 80%). After 3 hours the mixture was diluted with EtOAc and washed with brine, HCl (2%), NaHCO$_3$ (sat.), brine. The combined organic layer was dried over MgSO$_4$, evaporated and purified by flash chromatography (silica, EtOAc/Hexane) to yield 5e as white solid (2.23 grams, 93% yield).

$^1$H NMR (500 MHz, CDCl$_3$): δ=2.36 (s, 3H, SPhCH$_3$), 3.44 (dd, 1H, J$_1$=2.5, J$_2$=13.5 Hz, H-6), 3.50 (dd, 1H, J$_1$=6.0, J$_2$=13.5 Hz, H-6'), 4.06 (ddd, 1H, J$_1$=3.0, J$_2$=6.5, J$_3$=13.0 Hz H-5), 4.55 (t, 1H, J=10.5 Hz, H-2), 5.48 (t, 1H, J=9.5 Hz, H-4), 5.83 (d, 1H, J=10.5 Hz, H-1), 6.23 (t, 1H, J=10.0, Hz, H-3), 7.13-7.90 (m, 18H, aromatic).

$^{13}$C NMR (125 MHz, CDCl$_3$): δ=21.2 (SPhCH$_3$), 51.4, 53.7, 70.3, 71.9, 77.4, 83.4, 123.7, 128.3, 128.4, 128.5, 129.8, 131.2, 131.6, 134.2, 134.3, 134.5, 139.1, 165.2, 165.6, 166.9, 168.0.

ESIMS: m/z=687.4 (M+K$^+$ C$_{35}$H$_{28}$N$_4$O$_7$S requires 687.2).

p-Methylphenyl-5-deoxy-5-azido-2,3-di-O-benzoyl-1-thio-D-ribofuranose (8b) was prepared from the commercially available 1,2,3,5-tetra-O-acetyl-β-D-ribofuranose (Sigma) by the following 5 steps:

1,2,3,5-Tetra-O-acetyl-β-D-ribofuranose (3 grams, 9.43 mmol) in dry dichloromethane (35 mL) was added with 4-methylbenzenethiol (1.4 gram, 11.78 mmol), treated with TMSOTf (0.35 mL, 1.925 mmol) and stirred at ambient temperature under argon. Propagation of the reaction was monitored by TLC (EtOAc/Hexane 1:1), which indicated completion after 11 hours. The mixture was diluted by EtOAc (200 mL), neutralized by NaHCO$_3$ (sat.), and washed with brine. The combined organic layer was dried over MgSO$_4$, evaporated and used for the next step without further purification.

A suspension of the crude from the previous step in dry MeOH (40 mL) and dry dichloromethane (40 mL) was added a catalytic amount of NaOMe (0.5M solution in MeOH) at 0° C. Propagation of the reaction was monitored by TLC (MeOH 10%, dichloromethane 90%). After 2 hours the reaction mixture was neutralized by Dowex H$^+$ and evaporated to dryness. The resulted crude was used for the next step without further purification.

The crude from the previous step was dissolved under argon in dry dichloromethane (60 mL) and added with dry triethylamine (3 mL). The mixture was then added with freshly crystallized p-toluenesulfonyl chloride (2.16 grams, 11.31 mmol) and stirred 4° C. Propagation of the reaction was monitored by TLC (MeOH 10%, dichloromethane 90%) and indicated completion after 12 hours. The mixture was then evaporated to dryness and added NaN$_3$ (1.562 gram, 24 mmol), dry DMF (30 mL) and HMPA (3 mL). The reaction was heated to 50° C., and propagation was monitored by TLC (EtOAc 40%, Hexane 60%). After 3 hours the mixture was diluted with EtOAc and washed with brine, HCl (2%), NaHCO$_3$ (sat.), brine. The combined organic layer was dried over MgSO$_4$, evaporated to dryness to afford the crude product as a pale orange colored oil.

The crude from the previous step was dissolved in dry pyridine (40 mL) under argon. The mixture was added with benzoyl chloride (3.27 mL, 27.4 mmol) and propagation was monitored by TLC (EtOAc 30%, Hexane 70%). After 4 hours, the mixture was diluted with EtOAc and washed with brine, HCl (2%), NaHCO$_3$ (sat.), brine. The combined organic layer was dried over MgSO$_4$, evaporated and purified by column chromatography (silica, EtOAc/Hexane) to yield 8b 2.63 grams, (57% yield for the five steps) as a mixture of anomers (α/β; 1:4).

$^1$H NMR (500 MHz, CDCl$_3$) for the β-anomer: δ=2.36 (s, 3H, Me-STol), 3.58 (d, 2H, J=4.5 Hz, H-5, H-5'), 4.40 (dd, 1H, J$_1$=4.5, J$_2$=9.5 Hz, H-4), 5.47 (t, 1H, J=5.5 Hz, H-3), 5.34 (s, 1H, H-1), 5.58 (t, 1H, J=5.0 Hz, H-2), 7.17-8.11 (17.5H. aromatic protons of both anomers).

$^{13}$C NMR (125 MHz, CDCl$_3$): δ=21.1 (Me-Stol), 52.7 (C-5), 72.5 (C-3), 74.6 (C-2), 81.6 (C-4), 88.5 (C-1), 128.4, 128.8, 128.9, 129.8, 129.9, 130.6, 165.0, 165.3.

For the α-anomer $^1$H NMR (500 MHz, CDCl$_3$): δ=2.33 (s, 3H, Me-STol), 3.65 (dd, 1H, J$_1$=4.0, J$_2$=13.0 Hz, H-5), 3.75 (dd, 1H, J$_1$=3.0, J$_2$=13.5 Hz, H-5'), 4.67 (dd, 1H, J$_1$=4.0, J$_2$=7.0 Hz, H-4), 5.59 (dd, 1H, J$_1$=4.5, J$_2$=5.5 Hz, H-3), 5.74 (t, 1H, J=6.0 Hz, H-2), 6.03 (d, 1H, J=6.0 Hz, H-1) 7.17-8.11 (17.5H. aromatic protons of both anomers).

$^{13}$C NMR (125 MHz, CDCl$_3$): δ=21.1 (Me-Stol), 51.8 (C-5), 71.8 (C-3), 72.2 (C-2), 80.2 (C-4), 90.9 (C-1), 127.7, 128.5, 128.9, 129.0, 129.7, 138.8, ESIMS m/z 528.3 (M+K$^+$ C$_{26}$H$_{23}$N$_3$O$_5$S requires 528.5).

p-Methylphenyl-6-O-Acetyl-4-deoxy-4-azido-3,4-di-O-benzoyl-1-thio-β-D-glucopyranoside (5c) was prepared from p-Methylphenyl-2,3-di-O-benzoyl-1-thio-β-D-galactopyranoside 15 by the following four steps:

p-Methylphenyl-2,3-di-O-benzoyl-1-thio-β-D-galactopyranoside (900 mg, 1.82 mmol) in dry pyridine (12 mL), was added with a catalytic amount of DMAP and stirred under argon at 50° C. for 10 minutes. The mixture was added with tert-butyldiphenylsilylchloride (1.07 mL, 4.09 mmol) and the reaction progress was monitored by TLC (EtOAc 50%, Hexane 50%). After 30 minutes, the mixture was diluted with EtOAc and washed with brine, HCl (2%), NaHCO$_3$ (sat.), brine. The combined organic layer was dried over MgSO$_4$, evaporated and purified by column chromatography (silica, EtOAc/Hexane) to yield the product as white solid 1.1 gram (82% yield).

$^1$H NMR (500 MHz, CDCl$_3$): δ=1.06 (s, 9H, tert-butyl-SiPh$_2$), 2.30 (s, 3H, SPhCH$_3$), 3.76 (t, 1H, J=5.5 Hz, H-5), 3.93 (dd, 1H, J$_1$=4.5, J$_2$=15.5 Hz, H-6), 4.02 (dd, 1H, J$_1$=4.5, J$_2$=16.0 Hz, H-6'), 4.45 (d, 1H, J=3.0 Hz, H-4), 4.85 (d, 1H, J=10.0 Hz, H-1), 5.28 (dd, 1H, J$_1$=3.0, J$_2$=10.0 Hz, H-3), 5.78 (t, 1H, J=9.5 Hz, H-2), 6.98-7.98 (24H, aromatic).

$^{13}$C NMR (125 MHz, CDCl$_3$): δ=21.2 (SPhCH$_3$), 26.8 (tert-butylSiPh$_2$), 64.0, 68.0, 68.5, 75.8, 77.9, 86.9 (C-1), 127.8, 127.9, 128.3, 128.4, 128.6, 129.2, 129.6, 129.8, 129.9, 132.7, 133.1, 133.3, 135.6, 135.7, 138.2, 165.2, 165.9.

ESIMS: m/z=771.2 (M+K$^+$ C$_{43}$H$_{44}$O$_7$SiS requires 771.8).

The product of the previous step (1 gram, 1.36 mmol) was dissolved in pyridine (8 mL), and stirred at 0° C. for 15 minutes followed by the dropwise addition of trifluoromethanesulfonic anhydride (0.26 mL, 1.564 mmol). Propagation of the reaction was monitored by TLC (EtOAc 20%, Hexane 80%), which indicated completion after 15 minutes. The mixture was evaporated under vacuum to afford a pale yellow syrup, and was then put under argon and added NaN$_3$ (1.848 gram, 28 mmol), dry DMF (30 mL) and HMPA (5 mL) and stirred at room temperature. Propagation was monitored by TLC (EtOAc 15%, Hexane 85%). After 10 hours and the mixture was diluted with EtOAc and washed with brine, HCl (2%), NaHCO$_3$ (sat.), brine. The combined organic layer was dried over MgSO$_4$ evaporated and used for the next step without further purification.

The crude from the previous step was dissolved in pyridine (8 mL) and stirred under argon at 0° C. for 10 minutes in a polyethylene vessel. The mixture was added with HF/Pyr (4 mL) and its propagation was monitored by TLC (EtOAc 25%, Hexane 75%). After 5 minutes the mixture was diluted with EtOAc and neutralized with NaHCO$_3$ (sat.). The combined organic layer was dried over MgSO$_4$, evaporated to dryness and used for the next step without further purification.

The crude from the previous step was dissolved in pyridine (8 mL). The mixture was then added with a catalytic amount of 4-DMAP and acetic anhydride (0.258 mL, 2.8 mmol) with HF/Pyr (4 mL) and its propagation was monitored by TLC (EtOAc 20%, Hexane 80%). After 2 hours the mixture was diluted with EtOAc and neutralized with NaHCO$_3$ (sat.). The combined organic layer was dried over MgSO$_4$, evaporated to dryness and used for the next step without further purification. The mixture was diluted with EtOAc and washed with brine, HCl (2%), NaHCO$_3$ (sat.), brine. The combined organic layer was dried over MgSO$_4$, evaporated and purified by column chromatography (silica, EtOAc/Hexane) to yield the 5c as white solid 615 mg (73% yield for the four steps).

$^1$H NMR (500 MHz, CDCl$_3$): δ=2.14 (s, 3H, OCOMe), 2.32 (s, 3H, SPhCH$_3$), 3.63 (ddd, 1H, J$_1$=2.0, J$_1$=4.5, J$_1$=10.0 Hz, H-5), 3.79 (t, 1H, J=10.0 Hz, H-4), 4.30 (dd, 1H, J$_1$=5.0 J$_2$=12.5 Hz, H-6), 4.52 (dd, 1H, J$_1$=2.0, J$_2$=12.0 Hz, H-6'), 4.45 (d, 1H, J=3.0 Hz, H-4), 4.80 (d, 1H, J=9.5 Hz, H-1), 5.29 (t, 1H, J=9.5 Hz, H-2), 5.60 (t, 1H, J=9.5 Hz, H-3), 7.07-7.94 (14H, aromatic).

$^{13}$C NMR (125 MHz, CDCl$_3$): δ=20.8.7 (SPhCH$_3$), 21.2 (OCOMe), 60.5, 63.0, 70.3, 79.4, 76.2, 76.9, 86.3 (C-1), 127.6, 128.4, 128.7, 129.1, 129.7, 129.8, 129.9, 133.4, 133.5, 134.0, 138.8, 165.1, 165.6, 170.5.

ESIMS: m/z=600.1 (M+K$^+$ C$_{29}$H$_{27}$N$_3$O$_7$S requires 600.7).

Turning now to FIG. 12, the neomycin acceptor 1 was readily prepared in four chemical steps from the commercial neomycin B (Compound I) in an overall yield of 57% (briefly, these steps included perazidation of the commercial neomycin B (obtained from Sigma Israel) with TfN$_3$ according to the procedure of Wong (Kumar, V.; Jones, G. S., Jr.; Blacksberg, I.; Remers, W. A. *J. Med. Chem.* 1980, 23, 42-49; Yoshikawa, M.; Ikeda, Y.; Takenaka, K. *Chem. Lett.* 1984, 13, 2097-2100), selective silylation of the primary hydroxyl at C5", acetylation of all the remaining hydroxyls, and desilylation as depicted in FIG. 12).

The neomycin acceptor 1 was prepared as follows: Hexaazido-neomycin was prepared from the commercial neomycin B (tri-sulfate salt, 5 grams, 5.5 mmol) following the published procedure (Alper, P. B.; Hendrix, M.; Sears, P.; Wong, C.-H. *J. Am. Chem. Soc.* 1998, 120, 1965-1978) and was used for the next step without purification. The crude hexaazido-product was dissolved in pyridine (40 mL), added with DMAP (cat.) and stirred at 70° C. for 15 minutes. The reaction was then added with tert-butyldimethylsilylchloride (1.66 gram, 11 mmol), and TLC (EtOAc 100%) indicated completion after 30 minutes. The mixture was allowed to stir for additional 10 minutes and then added with pyridine (20 mL), DMAP (cat), and Ac$_2$O (7.8 mL, 82.5 mmol). Propagation of the reaction was monitored by TLC (EtOAc 30%, Hexane 70%), which indicated completion after 3 hours. The mixture was diluted with EtOAc and washed with brine, HCl (2%), NaHCO$_3$ (sat.), and brine. The combined organic layer was dried over MgSO$_4$, evaporated and purified by flash chromatography (silica, EtOAc/Hexane) to yield the corresponding silyl ether as a white powder (3.5 grams, 62% yield for 3 steps).

$^1$H NMR (500 MHz, CDCl$_3$) data for this compound is summarized in Table 1 hereinbelow.

$^{13}$C NMR (150.92 MHz): δ=18.2, 20.5, 20.6, 20.7, 20.9, 25.8, 29.6, 31.4, 50.7, 51.1, 56.7, 58.1, 59.2, 60.8, 63, 65, 68.7, 69, 70, 73.1, 75.2, 76, 76.7, 76.9, 77, 77.2, 81.6, 83.3, 96.0 (anomeric carbon), 99.6 (anomeric carbon), 106.3 (anomeric carbon), 168.5, 169.5, 169.7, 167.9, 170.2, 170.3.

ESIMS: m/z=1175.6 (M+K$^+$, C$_{41}$H$_{60}$O$_{19}$N$_{18}$Si requires 1175.4).

The silyl ether from the above (1.06 gram, 0.93 mmol) was dissolved in pyridine (8 mL) and stirred in a polyethylene vessel at 0° C. for 10 minutes. The mixture was added with HF/Pyr (4 mL). Propagation of the reaction was monitored by TLC (EtOAc 20%, Hexane 80%), which indicated completion after 5 minutes. The mixture was diluted with EtOAc, neutralized with NaHCO$_3$ (sat.). The combined organic layer was dried over MgSO$_4$, evaporated and purified by flash chromatography (silica, EtOAc/Hexane) to yield acceptor 1 as a white powder (884 mg, 93% yield).

$^1$H NMR (500 MHz, CDCl$_3$) data of acceptor 1 is summarized in Table 2 hereinbelow.

$^{13}$C NMR: δ=15.9, 16, 22.3, 22.4, 22.5, 22.6, 33.3, 52.6, 52.7, 58.3, 59.7, 60.8, 62.1, 67.4, 70.5, 70.9, 71, 71.1, 75.2, 77.8, 83.2, 83.6, 99.0 (anomeric carbon), 101.2 (anomeric carbon), 108.0 (anomeric carbon), 170.4, 171.2, 171.4, 171.6, 171.7, 171.9.

ESIMS: m/z=1061.2 (M+K$^+$, C$_{35}$H$_{46}$O$_{19}$N$_{18}$ requires 1061.4).

NIS-promoted coupling of acceptor 1 with various thioglycosides furnished the designed protected pseudo-pentasaccharides 16a-h in 58-89% yields. Purity and exclusive stereochemistry of new glycosidic bonds in 16a-d were confirmed by $^1$H NMR spectroscopy (16a: H-1, δ 4.86 ppm, J$_{1,2}$=8.0 Hz. 16b: H-1, δ 4.81 ppm, J$_{1,2}$=7.5 Hz. 16c: H-1, δ 5.62 ppm, J$_{1,2}$=8.5 Hz. 16d: H-1, δ 5.95 ppm, J$_{1,2}$=4.5 Hz; see below for a more detailed description and tables).

Compound 16a was prepared as follows: To powdered, flame dried 4 Å molecular sieves (0.4 gram) was added CH$_2$Cl$_2$ (4 mL), followed by the addition of acceptor 1 (100 mg, 0.098 mmol) and donor 9 (65 mg, 0.143 mmol). After being stirred for 10 minutes at room temperature, the mixture was treated with NIS (64.3 mg, 0.286 mmol). After an additional 5 minutes at room temperature, TfOH (cat.) was added. Propagation of the reaction was monitored by TLC (EtOAc 50%, Hexane 50%), which indicated completion after 10 minutes. The reaction was diluted with EtOAc, and filtered through celite. After thorough washing with EtOAc, the washes were combined and extracted with 10% Na$_2$S$_2$O$_3$, saturated (aq.) NaHCO$_3$, brine, dried over MgSO$_4$ and concentrated. The crude was purified by flash chromatography to yield 16a (112 mg, 81% yield).

$^1$H NMR (500 MHz, CDCl$_3$) data of 16a are summarized in Table 3 hereinbelow.

$^{13}$C NMR: δ=20.4, 20.6, 20.7, 29.6, 31, 40.7, 50, 50.9, 56.3, 58, 58.8, 60.6, 6.60, 62.5, 65, 68.1, 68.4, 69, 70.3, 71, 72.4, 74.8, 75, 75.5, 76.4, 80.2, 83.5, 96.4 (anomeric carbon), 98.8 (anomeric carbon), 99.0 (anomeric carbon), 108.2 (anomeric carbon), 128.9, 129.3, 129.7, 133.7, 167.7, 167.1, 168.3, 169.5, 169.6, 169.8, 170.1.

ESIMS: m/z=1453.2 (M$^+$K$^+$, C$_{50}$ClH$_{59}$N$_{24}$O$_{24}$ requires 1453).

Compound 16b. The titled compound was prepared as was described for the preparation of compound 16a. The conditions used were: donor 5f (430 mg, 0.79 mmol), acceptor 1 (646 mg, 0.63 mmol), NIS (430 mg, 1.9 mmol), TfOH (cat.) CH$_2$Cl$_2$ (15 mL), and 4 Å molecular sieves (1.5 gram). The reaction was performed at 0° C. to yield 16b (780 mg, 86%) as a mixture of anomers (α/β 1:2) as determined by NMR.

ESIMS: m/z=1481.7 (M$^+$K$^+$, C$_{55}$H$_{62}$N$_{24}$O$_{24}$ requires 1481.6).

The above mixture could not be separated until after the next step. Thus, compound 16b (200 mg, 0.138 mmol, as a mixture of anomers) was dissolved in 33% solution of MeNH$_2$ in EtOH (40 mL) and stirred at room temperature for 48 hours. Propagation of the reaction was monitored by TLC (MeOH 20%, CHCl$_3$ 80%). The reagent and the solvent were removed by evaporation and the residue was purified by flash chromatography (silica, MeOH/CHCl$_3$) to yield the corresponding octaazido-octaol as a β-anomer 16bβ (72.7 mg, 53%), and the octaazido-heptaol-$C_{2'}$—O-benzoyl as an α-anomer 16bα (49.2 mg, 36%).

$^1$H NMR (500 MHz, $CDCl_3/CD_3OD$; 10:1) data of the β-anomer and of the α-anomer are summarized in Table 4 and Table 5 hereinbelow, respectively.

$^{13}$C NMR (β-anomer): δ=29.5, 38.1, 51.1, 51.2, 51.5, 59.6, 59.8, 60.6, 62.3, 62.5, 68.7, 68.9, 69.4, 71.1, 71.1, 73.6, 73.6, 73.7, 74.1, 75.3, 75.4, 75.9, 76.1, 80.6, 84.3, 96.2 (anomeric carbon), 98.3 (anomeric carbon), 102.8 (anomeric carbon), 108.5 (anomeric carbon).

ESIMS: m/z=1021.3 ($M+K^+$, $C_{29}H_{42}N_{24}O_{16}$ requires 1021.8).

$^{13}$C NMR (α-anomer): δ=29.5, 39.1, 51.0, 51.4, 51.7, 59.4, 59.7, 60.9, 62.9, 62.9, 68.5, 69.7, 70.8, 71.0, 71.2, 74.1, 75.0, 75.6, 75.9, 76.2, 80.6, 84.2, 96.5 (anomeric carbon), 97.7 (anomeric carbon), 98.4 (anomeric carbon), 107.3 (anomeric carbon), 120.1, 125.9, 128.3, 129.4, 135.9.

ESIMS: m/z=1125.3 ($M^+K^+$, $C_{36}H_{47}N_{24}O_{17}$ requires 1125.8).

Compound 16c. The titled compound was prepared as described for the preparation of compound 16a. The conditions used were: donor 10 (467.2 mg, 0.73 mmol), acceptor 1 (250 mg, 0.24 mmol), NIS (330 mg, 1.47 mmol), TfOH (cat.). $CH_2Cl_2$ (5 mL), 4 Å molecular sieves (500 mg), to yield 226 mg of 16c (58%).

$^1$H NMR (500 MHz, $CDCl_3$) data of 16c are summarized Table 6 hereinbelow.

$^{13}$C NMR: δ=20.4, 20.7, 20.8, 20.9, 29.6, 40.8, 50.5, 54.7, 56.6, 58.2, 59.0, 60.7, 65.5, 69.0, 69.8, 70.2, 70.8, 72.0, 73.0, 75.1, 75.3, 76.4, 76.9, 81.0, 81.2, 96.4 (anomeric carbon), 98.6 (anomeric carbon), 99.5 (anomeric carbon), 107.2 (anomeric carbon), 128.3, 128.4, 128.5, 128.6, 129.7, 129.9, 133.3, 133.5, 165.2, 165.7, 167.1, 168.4, 169.5, 169.7, 169.8, 169.9, 170.1.

ESIMS: m/z=1636.3 ($M+K^+$, $C_{65}H_{68}N_{19}O_{28}Cl$ requires 1637.1).

Compound 16d: The titled compound was prepared as was described for the preparation of compound 16a with the following modifications: Donor 11 (157 mg, 0.49 mmol), acceptor 1 (200 mg, 0.196 mmol), NIS (110 mg, 0.49 mmol), TfOH (cat.), 4 Å molecular sieves (400 mg). In an attempt to increase the beta selectivity, acetonitrile (4 mL) was used as a solvent and the reaction temperature was –35° C. Under these conditions, 16d was isolated as a mixture of anomers α/β; 1:11 (238 mg, (95%). This mixture was further separated to afford 178 mg (71%) of the pure β-anomer.

$^1$H NMR (500 MHz, $CDCl_3$) data of 16d are summarized in Table 7 hereinbelow.

$^{13}$C NMR: δ=20.4, 20.6, 20.7, 20.8, 23.8, 29.5, 29.7, 50.6, 50.7, 56.7, 57.9, 59.2, 60.43, 60.86, 62.1, 63.44, 64.45, 65.62, 68.6, 68.9, 69.2, 70.0, 70.7, 70.9, 71.2, 72, 73.2, 75.2, 75.3, 76.1, 77.3, 77.8, 78.5, 79.1, 81.3, 81.7, 97.9 (anomeric carbon), 101.4 (anomeric carbon), 106.1 (anomeric carbon), 108.5 (anomeric carbon), 170.4, 171.5, 171.6, 171.8, 171.9, 172.5.

ESIMS: m/z=1319.3 ($M+K^+$, $C_{46}H_{60}N_{18}O_{26}$ requires 1319.5).

These protected compounds (16a-d) were subjected to a two-step deprotection, removal of all the ester and phthalimido groups by treatment with methylamine (33% solution in EtOH) and reduction of all the azido groups by Staudinger reaction, to furnish the final products, compounds II-V, with high purity and isolated yields, as described in greater detail below after the preparation of compounds 16e-h.

Compound 16i: To a powdered, flame dried 4 Å molecular sieves (0.7 gram) was added $CH_2Cl_2$ (7 mL) containing donor 8e (298 mg, 0.491 mmol) (prepared according to the published: Ivan Chiu-Machado, Julio C Castro-Palomino, Madrazo-Alonso, Carlos Lopetegui-Palacios and Vicente Veers-Bencomo *J. Carbohydr. Chem.* 1995, 14, 551-561) and acceptor 2 (127.6 mg, 0.123 mmol). After being stirred for 20 minutes at room temperature, the mixture was cooled to –10° C. and treated with $BF_3OEt_2$ (40 μL). Propagation of the reaction was monitored by TLC (EtOAc 45%, Hexane 55%), which indicated completion after 45 minutes. The reaction was quenched with triethylamine, diluted with EtOAc, and filtered through celite. After thorough washing of the celite with EtOAc, the washes were combined and extracted with saturated (aq.) $NaHCO_3$, brine, dried over $MgSO_4$ and concentrated. The crude was purified by flash chromatography (silica, EtOAc/Hexane) to yield 16i compound (164 mg, 90% yield).

$^1$H NMR (500 MHz, $CDCl_3$) data of 16i are summarized in Table 14 hereinbelow.

$^{13}$C NMR: δ=20.5, 20.6, 20.7, 20.9, 31.3 (C-2), 33.6 (C-5"), 50.5 (C-6'"), 51.0 (C-6'), 60.75, 64.3 (C-5""), 65.6, 68.8, 69.2, 69.5, 70.0, 72.5, 73.7, 74.4, 75.3, 76.2, 76.3, 78.1, 79.4, 80.9, 81.1, 86.9 (C-1""), 96.4 (C-1'), 98.9 (C-1'"), 106.3 (C-1"), 128.4, 128.5, 128.6, 128.8, 129.1, 129.6, 129.7, 129.8, 128.9, 133.1, 133.4, 133.6, 165.1, 165.2, 166.1, 168.5, 169.5, 169.6, 169.8, 170.1, 170.1.

MALDI-TOFMS: m/z=1522.0 ($M+K^+$, $C_{61}H_{66}N_{18}O_{25}S$ requires 1521.9).

Compound 19a was prepared according to the procedure published by Swayze et al. (Baogen Wu, Jun Yang, Yun He and Eric E. Swayze, *Organic Letters*, 2002, 4(20), 3455-3458). Acceptor 1 (250 mg, 0.2445 mmol) was dissolved in dry $CH_2Cl_2$ (9.8 mL) under argon, and added with 4-methylbenzenethiol (33.1 mg, 0.269 mmol) and stirred at 0° C. for 15 minutes. The mixture was then treated with $BF_3OEt_2$ (0.093 mL, 0.733 mmol), stirred at 0° C. for 20 minutes and then allowed to warm to room temperature. Propagation of the reaction was monitored by TLC (EtOAc/Hexane; 1:1) and indicated termination after 45 minutes.

The reaction was quenched with triethylamine, diluted with EtOAc, and extracted with saturated (aq.) $NaHCO_3$, brine, dried over $MgSO_4$ and concentrated. The crude was purified by flash chromatography (silica, EtOAc/Hexane) to yield the neamine moiety (18, FIG. 13), 133.4 mg (99% yield) (full NMR and mass spectra data are given in the reference above) and compound 19a (FIG. 13), 47 mg (32% yield).

$^1$H NMR (500 MHz, $CDCl_3$) data of 19a: δ=2.12 (s, 3H, OCOMe), 2.16 (s, 3H, OCOMe), 2.17 (s, 3H, OCOMe) 2.35 (s, 3H, MeSTol), 3.33 (dd, 1H, $J_1$=4.5, $J_2$=13.0 Hz, HII-6), 3.45 (bs, 1H, HII-2), 3.59 (dd, 1H, $J_1$=7.0, $J_2$=12.5 Hz, HII-6'), 3.78 (dd, 1H, $J_1$=2.5, $J_2$=12.5 Hz, HI-5), 3.85 (dd, 1H, $J_1$=2.5, $J_2$=12.5 Hz, HI-5'), 4.07 (dd, 1H, $J_1$=$J_2$=6.0 Hz, HII-5), 4.20 (m, 1H, HI-4), 4.53 (dd, 1H, $J_1$=$J_2$=5.5 Hz, HI-3), 4.72 (bs, 1H, HII-4), 4.90 (s, 1H, HII-1), 5.45 (bs, 1H, HII-3), 5.20 (dd, 1H, $J_1$=$J_2$=3.5 Hz, HI-2'), 5.38 (d, 1H, J=3.0 Hz, HI-1), 7.16 (d, J=7.5 Hz, 2H, ortho to the methyl of S-Tol), 7.41 (d, J=8.0 Hz, 2H, ortho to the sulfur of S-Tol).

$^{13}$C NMR: δ=20.7, 20.7, 20.8, 50.7 (CI-6), 56.6 (CII-2), 61.3 (CII-5), 65.6 (CII-4), 68.7, 73.2 (CI-2), 75.3 (CI-2), 76.5 (CI-3), 83.1 (CI-4), 88.6 (CI-1), 99.3 (CII-1), 128.3, 130.0, 133.1, 138.6, 168.5, 169.8, 170.2.

MALDI-TOFMS: m/z=633.1 ($M+K^+$, $C_{24}H_{30}N_6O_{10}S$ requires 633.3).

Compound 19b (FIG. 13) was prepared by deacetylation of compound 19a, using sodium methoxide in methanol, followed by selective protection of the primary alcohol by TBDPS and treatment with acetic anhydride in pyridine.

General procedure for the coupling of donors 5c, 5e, 8b, 19a and acceptor 1: To a powdered, flame dried 4 Å molecular sieves (0.5 gram) was added $CH_2Cl_2$ (5 mL), followed by the addition of acceptor 1 (150 mg, 0.147 mmol) and donor 5e (65 mg, 0.293 mmol). After being stirred for 10 minutes at room temperature, the mixture was treated with NIS (66.0 mg, 0.286 mmol). After additional 5 minutes at room temperature, TfOH (cat) was added. Propagation of the reaction was monitored by TLC (EtOAc 50%, Hexane 50%), which indicated completion after 10 minutes. The reaction was diluted with EtOAc, and filtered through celite. After thorough washing of the Celite with EtOAc, the washes were combined and extracted with 10% $Na_2S_2O_3$, saturated (aq.) $NaHCO_3$, brine, dried over $MgSO_4$ and concentrated. The crude was purified by flash chromatography to yield 16g (207 mg, 91% yield).

$^1$H NMR (500 MHz, $CDCl_3$) data of 16g are summarized in Table 8 hereinbelow.

$^{13}$C NMR: δ=20.3, 20.7, 20.8, 21.0, 31.3 (C-2), 50.3 (C-6'''), 51.2 and 51.4 (C6' and C-6''''), 54.6, 56.7, 58.3, 59.0, 60.6, 65.4, 68.6 (C-5''), 68.9, 69.8, 70.3, 70.4, 70.7, 72.7, 73.7, 75.3, 75.5, 77.4, 81.1, 82.3, 96.5 (C-1'), 98.3 (C-1''''), 99.6 (C-1'''), 107.4 (C-1), 122.8, 123.1, 128.3, 128.4, 128.6, 129.7, 129.8, 129.9, 130.4, 133.3, 133.5, 165.1, 165.7, 168.4, 169.6, 169.7, 169.8, 169.9, 170.3, 177.1.

ESIMS: m/z=1585.3 (M+K$^+$, $C_{63}H_{66}N_{22}O_{26}$ requires 1585.8).

Compound 16f: The titled compound was prepared as was described for the preparation of compound 16g. The conditions used were: Donor 5c (149 mg, 0.306 mmol), acceptor 1 (250 mg, 0.245 mmol), NIS (68 mg, 0.302 mmol), TfOH (cat.), acetonitrile anhydrous (7 mL), 4 Å molecular sieves (500 mg) to yield 16f (271 mg, 80%).

$^1$H NMR (500 MHz, $CDCl_3$) data of 16f are summarized in Table 9 hereinbelow.

$^{13}$C NMR: δ=20.7, 20.8, 20.9, 30.2 (C-2), 50.3 and 51.0 (C-6''', C-6' could not be distinguished), 53.6 (C-5''''), 56.3, 58.1, 58.8, 60.9, 64.6, 65.4, 67.3 (C-5''), 68.6, 69.2, 69.4, 70.1, 72.6, 73.3, 74.2, 75.4, 75.4, 80.1, 80.3, 81.3, 96.3 (C-1'), 98.9 (C-1'''), 105.6 (C-1'), 107.3 (C-1''''), 124.8, 128.4, 128.5, 128.7. 129.1, 129.7, 129.7, 133.5, 133.6, 165.3, 165.5, 168.6, 169.4, 169.7, 169.8, 170.2, 170.3.

ESIMS: m/z=1426.4 (M+K$^+$, $C_{54}H_{61}N_{21}O_{24}$ requires 1426.2).

Compound 16e: The titled compound was prepared as described for the preparation of compound 16g. The conditions used were: Donor 8b (207 mg, 0.36 mmol), acceptor 1 (250 mg, 0.24 mmol), NIS (81 mg, 0.36 mmol), TfOH (cat.), acetonitrile anhydrous (8 mL), 4 Å molecular sieves (800 mg), −40° C., to yield 16e (226 mg, 87%).

$^1$H NMR (500 MHz, $CDCl_3$) data of 16e are summarized in Table 10 hereinbelow.

$^{13}$C NMR: δ=20.5, 20.7, 20.8, 31.0 (C-2), 49.9 (C-6'''), 51.1 (C-6'), 56.2, 58.1, 58.9, 60.5, 60.8 (C-5''), 65.2, 67.7 (C-6''''), 68.4, 68.5, 69.4, 70.4, 71.9, 72.3, 72.6, 73.6, 74.7, 74.9, 75.5, 76.6, 80.2, 83.4, 96.6 (C-1), 98.7 (C-1'''), 101.1 (C-1''''), 108.2 (C-1''), 128.5, 128.7, 129.5, 129.7, 129.8, 133.1, 133.5, 164.9, 169.6, 169.7, 169.9, 170.2, 170.7.

ESIMS: m/z=1498.3 (M+K$^+$, $C_{57}H_{64}N_{21}O_{26}$ requires 1497.8).

Compound 16h: The titled compound was prepared as described for the preparation of compound 16g. The conditions used were: Donor 19a (135 mg, 0.212 mmol), acceptor 1 (150 mg, 0.147 mmol), NIS (52 mg, 0.231 mmol), TfOH (cat.), acetonitrile anhydrous (5 mL), 4 Å molecular sieves (600 mg), to yield 16h (101.7 mg, 67%).

$^1$H NMR (500 MHz, $CDCl_3$) data of 16h are summarized in Table 11 hereinbelow.

$^{13}$C NMR: δ=20.5, 20.6, 20.7, 20.8, 31.4 (C-2), 50.5 and 50.6 (C-6'''' and C-6'''), 51.0 (C-6'), 56.1, 56.4, 58.0, 59.0, 60.6, 64.4 (C-5''''), 65.6, 65.7, 68.6 (C-5''), 68.7, 68.8, 69.3, 69.3, 69.9, 73.4, 73.9, 74.1, 74.2, 75.3, 75.4, 76.2, 76.3, 78.8, 79.9, 81.1, 96.3 (C-1'), 98.6 (C-1''''), 98.8 (C-1'''), 105.1 (C-1''''), 106.8 (C-1''), 168.5, 168.6, 169.5, 169.6, 169.8, 169.8, 169.9, 170.0, 170.2, 170.8.

MALDI-TOFMS: m/z=1574.3 (M+K$^+$, $C_{54}H_{70}N_{24}O_{30}$ requires 1574.3).

Compound 16j: The titled compound was prepared as was described for the preparation of compound 16g. The conditions used were: Donor 5a (150 mg, 0.372 mmol), acceptor 1 (250 mg, 0.245 mmol), NIS (104.6 mg, 0.465 mmol), TfOH (cat.). Acetonitrile (8 mL), 4 Å molecular sieves (800 mg), −40° C., to yield 16j (282 mg, 85%).

$^1$H NMR (500 MHz, $CDCl_3$) data of 16j are summarized in Table 16 hereinbelow.

$^{13}$C NMR (125 MHz, $CDCl_3$): δ=20.4, 20.5, 20.6, 20.7, 20.8, 31.7 (C-2), 50.8 (C-6'''), 52.4 (C-6'), 57.3, 58.3, 59.0, 60.5, 61.2 (C-5''), 65.2, 68.1 (C-6''''), 68.4, 68.5, 69.4, 71.1, 71.7, 72.3, 72.6, 73.8, 74.5, 75.1, 75.8, 76.6, 80.8, 83.4, 97.1 (C-1), 98.1 (C-1'''), 101.4 (C-1''''), 110.2 (C-1''), 163.9, 164.2, 166.9, 169.1, 169.4, 169.6, 169.7, 169.9, 170.2, 170.7.

MALDI-TOFMS m/z 1392.4 (M+K$^+$, $C_{49}H_{64}N_{18}O_{28}$ requires 1392.1).

The preparation of compounds II-XIII according to the present invention is now described.

Compound II was prepared as follows: Compound 16a (0.11 gram, 0.078 mmol) was dissolved in 33% solution of $MeNH_2$ in EtOH (40 mL) and the mixture was stirred at room temperature for 30 hours. The reagent and the solvent were removed by evaporation and the residue was dissolved in THF (10 mL), NaOH 0.1M (2 mL) and stirred at 60° C. for 10 minutes after which $PMe_3$ (1M solution in THF, 3.73 mL, 3.73 mmol) was added. Propagation of the reaction was monitored by TLC ($CH_2Cl_2$/MeOH/$H_2O$/$MeNH_2$, 33% solution in EtOH, 10:15:6:15, Rf=0.33), which indicated completion after 3.5 hours. The reaction mixture was purified by flash chromatography on a short column of silica and the column was washed as follows: THF, EtOAc, MeOH/EtOAc (1:1), MeOH, and finally with $MeNH_2$ (33% solution in EtOH). The fractions containing the product were evaporated under vacuum, re-dissolved in water and evaporated again to afford the product as a free amine (48.7 mg, 81%). This product was then dissolved in water, the pH was adjusted to 7.5 with 0.01 M $H_2SO_4$ and the solution was then lyophilized to give the sulfate salt of Compound II (88.5 mg) as a white foamy solid.

$^1$H NMR (500 MHz, $D_2O$, pH 4.5, sulfate salt): δ=1.85 (ddd, 1H, $J_1=J_2=J_3=12.5$ Hz, H-2 axial), 2.38 (dt, 1H, $J_1=4.5$ $J_2=12.5$, H-2 equatorial), 3.07-4.53 (m, 26H), 4.78 (d, 1H, J=7.0 Hz, anomeric proton), 5.21 (d, 1H, J=1.5 Hz, anomeric proton), 5.34 (d, 1H, J=3.0 Hz, anomeric proton), 5.97 (d, 1H, J=4.0 Hz, anomeric proton).

$^{13}$C NMR (125.8 MHz, $D_2O$, pH 4.5, sulfate salt): δ=29.8, 34.6, 42.2, 42.3, 49.9, 50.3, 51.2, 51.6, 52.6, 55.1, 62.3, 64.3, 69.2, 69.4, 69.5, 69.9, 71.3, 71.9, 72.8, 73.8, 74.1, 74.9, 77.1, 82.0, 86.8, 96.9 (anomeric carbon), 97.1 (anomeric carbon), 102.0 (anomeric carbon), 112.1 (anomeric carbon).

ESIMS: m/z=781.2 (M+Li$^+$, $C_{29}H_{58}N_8O_{16}$ requires 781.2).

Compound III was prepared as was described for the preparation of Compound II with the following quantities: the product (β-anomer) that was obtained by the partial deprotection of compound 16b (122.4 mg, 0.124 mmol), THF (9 mL), NaOH 0.1M (3 mL), $PMe_3$ (1M solution in THF, 6.8 mL, 6.8 mmol), gave the product as a free amine (93.1 mg, 96%). This product was dissolved in water, the pH was adjusted to 7.5 with 0.01 M $H_2SO_4$, and the solution was lyophilized to afford the sulfate salt of Compound III (134.5 mg) as a white foamy solid.

$^1$H NMR (500 MHz, $D_2O$, pH 4.5, sulfate salt): δ=1.77 (ddd, 1H, $J_1=J_2=J_3$=12.5 Hz, H-2 axial), 2.38 (bd, 1H, H-2 equatorial), 2.83-4.39 (m, 26H), 4.54 (d, 1H, J=7.5 Hz, anomeric proton), 5.17 (s, 1H, anomeric proton), 5.31 (s, 1H, anomeric proton), 5.98 (s, 1H, anomeric proton).

$^{13}$C NMR (125.8 MHz, $D_2O$, pH 4.5, sulfate salt): δ=20.8, 23.6, 30.0, 42.2, 42.3, 42.5, 50.2, 51.8, 52.7, 55.1, 55.2, 55.8, 69.3, 69.4, 69.6, 69.9, 71.1, 71.6, 72.0, 73.7, 74.3, 74.4, 75.0, 77.1, 81.3, 86.9, 96.4 (anomeric carbon), 97.0 (anomeric carbon), 105.1 (anomeric carbon), 112.5 (anomeric carbon).

ESIMS: m/z=813.2 ($M+K^+$, $C_{29}H_{58}N_8O_{16}$ requires 813.8).

Compound IV was prepared as was described for the preparation of Compound II with the following quantities: 16c (180 mg, 0.113 mmol) was treated in the first step with 33% solution of $MeNH_2$ in EtOH (40 mL) for 40 hours; the product from this step was dissolved in THF (10 mL), NaOH 0.1M (2 mL), and treated with $PMe_3$ (1M solution in THF, 4.05 mL, 4.05 mmol) to yield Compound IV as a free amine (73.1 mg, 84%). The amine was dissolved in water, the pH was adjusted to 7.5 with $H_2SO_4$ (0.01 M), and the solution lyophilized to give the sulfate salt of Compound IV (117 mg) as a white foamy solid.

$^1$H NMR (500 MHz, $D_2O$, pH 3.75, sulfate salt): δ=1.94 (ddd, 1H, $J_1=J_2=J_3$=12.5 Hz, H-2 axial), 2.35 (broad dt, H-2 equatorial), 2.96 (t, 1H, J=10.0 Hz, H-2''''), 2.97 (broad t, 1H, H-3'''), 3.05 (dd, 1H, $J_1$=8.5 $J_2$=13.0 Hz), 3.21-3.33 (m, 5H, H-4''''), 3.37-3.47 (m, 5H, H-2', H-2''', H-5''''), 3.61-3.70 (m, 4H, H-4'''', H-3'''), 3.76-3.80 (m, 2H), 3.83-3.90 (m, 2H), 3.96 (t, 1H, J=10.0 Hz, H-3'), 4.14-4.20 (m, 2H, H-5''), 4.23 (broad t, 1H), 4.31 (broad t, 1H, H-3''), 4.41 (broad t, 1H, H-2''), 4.79 (d, J=8.5 Hz, 1H, H-1''''), 5.19 (s, 1H, H-1''), 5.32 (s, 1H, H-1'''), 5.98 (d, J=4.0 Hz, 1H, H-1').

$^{13}$C NMR: δ=26.4, 29.6, 42.2, 42.5, 50.3, 51.6, 52.6, 55.1, 57.4, 61.8, 68.9, 69.4, 69.7, 70.8, 71.4, 71.6, 72.3, 73.2, 73.6, 74.0, 74.6, 76.2, 76.6, 77.9, 81.7, 87.3, 96.70 (anomeric carbon), 96.73 (anomeric carbon), 101.0 (anomeric carbon), 112.5 (anomeric carbon).

ESIMS: m/z=798.2 ($M+Na^+$, $C_{29}H_{57}N_7O_{17}$ requires 798.3).

Compound V was prepared as follows: A catalytic amount of NaOMe (0.5M solution in MeOH) was added to a suspension of compound 16d (140 mg, 0.11 mmol) in dry MeOH (10 mL) at 0° C., and the propagation of the reaction was monitored by TLC (MeOH 10%, dichloromethane 90%). After 3 hours the mixture was neutralized with Dowex $H^+$ and evaporated to dryness. The resulted crude was then treated as described for the preparation of Compound II to yield the free amine of Compound V (57.1 mg, 70%).

$^1$H NMR (500 MHz, $D_2O$, pH 4.5, sulfate salt): δ=1.86 (ddd, 1H, J1=J2=J3=12.5 Hz, H-2 axial), 2.33 (broad dt, H-2 equatorial), 3.10 (dd, 1H, J1=7.0 J2=13.0 Hz), 3.20-4.43 (m, 17H), 3.84 (s, 1H, anomeric proton), 5.16 (s, 1H, anomeric proton), 5.30 (s, 1H, anomeric proton), 5.93 (d, J=3.0 Hz, 1H, anomeric proton).

$^{13}$C NMR (125.8 MHz, $D_2O$, pH 4.5, sulfate salt): δ=30.2, 42.2, 42.2, 50.3, 51.8, 52.6, 55.5, 62.0, 69.0, 69.5, 69.9, 71.2, 72.1, 74.3, 75.1, 76.6, 77.1, 83.0, 83.6, 86.7 (anomeric carbon), 96.9 (anomeric carbon), 96.9 (anomeric carbon), 112.0 (anomeric carbon).

ESIMS: m/z=769.2 ($M+Na^+$, $C_{28}H_{54}N_6O_{17}$ requires 769.3).

Compound VIII: The titled compound was prepared as described for the preparation of Compound II with the following quantities: 16g (207 mg, 0.134 mmol), in 33% solution of $MeNH_2$ in EtOH (40 mL), THF (4.5 mL), NaOH 0.1M (1 mL), $H_2O$ (1 mL), $PMe_3$ (1M solution in THF, (2.68 mL, 2.68 mmol), to yield of the free amine (81.9 mg, 79%). The product was dissolved in water and the pH was adjusted to 6.8 by $H_2SO_4$ (0.01 M), and lyophilized to afford the sulfate salt of Compound VIII as a white foamy solid.

NMR analyses were performed at 500 MHz, in $D_2O$, and at pH 3.45, adjusted by $H_2SO_4$).

$^1$H NMR: δ=1.93 (ddd, 1H, $J_1=J_2=J_3$=12.5 Hz, H-2 axial) 2.35 (broad dt, 1H, H-2 equatorial), 2.98 (t, J=9.0 Hz 1H), 3.05-3.09 (m, 2H), 3.17-3.89 (m, 17H), 3.97 (t, J=9.5 Hz 1H), 4.13-4.16 (m, 2H), 4.23-4.30 (m, 3H), 4.41 (bs, 1H), 4.56 (dd, 1H, $J_1=J_2$7.5 Hz), 4.89 (d, 1H, J=8.5 Hz, H-1''''), 5.20 (s, 1H, H-1'''), 5.35 (s, 1H, H-1''), 6.00 (d, 1H, J=4.0 Hz, H-1').

$^{13}$C NMR: δ=29.8 (C-2), 42.2 (C-6''' and C-6''''), 42.5 (C-6'), 50.2, 51.7, 52.6, 55.2, 57.4, 69.0, 69.4, 69.8, 70.5, 71.2, 72.3, 73.3, 73.6, 73.8, 74.1, 74.2, 74.5, 75.9, 76.6, 81.4, 87.1, 96.6, 96.7, 101.4, 112.4.

ESIMS: m/z=813.3 ($M+K^+$, $C_{29}H_{58}N_8O_{16}$ requires 813.3).

Compound VI: The titled compound was prepared as was described for the preparation of Compound II with the following quantities: compound 16e (261.2 mg, 0.188 mmol), in 33% solution of $MeNH_2$ in EtOH (40 mL), THF (6 mL), NaOH 0.1M (3 mL), $H_2O$ (2 mL), $PMe_3$ (1M solution in THF, (10.43 mL, 10.43 mmol), to yield the free amine (79.4 mg, 57%). The product was dissolved in water and the pH was adjusted to 6.8 by $H_2SO_4$ (0.01 M), and the solution lyophilized to afford the sulfate salt of Compound VI as a white foamy solid.

NMR analyses were performed at 500 MHz, in $D_2O$, and at pH 4.49, adjusted by $H_2SO_4$).

$^1$H NMR: δ=1.88 (ddd, 1H, $J_1=J_2=J_3$=12.5 Hz, H-2 axial) 2.27 (broad dt, 1H, H-2 equatorial), 2.90-2.95 (m, 1H), 3.03 (dd, 1H, $J_1$=8.5, $J_2$=13.5 Hz), 3.03 (dd, 1H, $J_1$=3.5, $J_2$=10.5 Hz), 2.20-2.29 (m, 4H), 3.32-3.37 (m, 2H), 3.44 (bs, 1H), 3.58 (t, 1H, J=9.5 Hz), 3.66 (dd, 1H, $J_1$=6.0, $J_2$=11.0 Hz) 3.79-4.19 (m, 10H), 4.37 (d, 1H, J=4.0 Hz), 4.45 (dd, 1H, $J_1$=4.5, $J_2$=7.5 Hz), 4.99 (s, 1H, H-1'''), 5.14 (s, 1H, H-1''''), 5.27 (s, 1H, H-1''), 5.97 (d, 1H, J=4.0 Hz, H-1').

$^{13}$C NMR: δ=27.5 (C-2), 42.3 (C-6'''), 42.4 (C-6'), 44.8 (C-5''''), 50.3, 51.7, 52.6, 55.5, 68.7, 69.1 (C-5''), 69.4, 69.8, 71.2, 72.3, 73.2, 74.0, 74.1, 74.2, 75.8, 75.9, 76.9, 87.2, 96.4 (C-1''' and C-1'), 109.7 (C-1''''), 112.4 (C-1'').

ESIMS: m/z=784.4 ($M+K^+$, $C_{28}H_{55}N_7O_{16}$ requires 784.8).

Compound VII: The titled compound was prepared as was described for the preparation of Compound II with the following quantities: compound 16f (220 mg, 0.151 mmol), in 33% solution of $MeNH_2$ in EtOH (60 mL), THF (4.5 mL), NaOH 0.1M (1 mL), $H_2O$ (1 mL), $PMe_3$ (1M solution in THF, (2.64 mL, 2.64 mmol), to yield of the free amine (98.3 mg, 84%). The product was dissolved in water and the pH was adjusted to 6.8 by $H_2SO_4$ (0.01 M), and the solution was lyophilized to afford the sulfate salt of Compound IV as a white foamy solid.

NMR analyses were performed at 500 MHz, in $D_2O$, and at pH 4.2, adjusted by $H_2SO_4$).

$^1$H NMR: δ=1.92 (ddd, 1H, $J_1=J_2=J_3$=12.5 Hz, H-2 axial) 2.32 (broad dt, 1H, H-2 equatorial), 2.98-3.05 (m, 2H), 3.20-3.47 (m, 10H), 3.56-3.86 (m, 10H), 3.92 (t, J=10.0 Hz 1H), 4.09-4.20 (m, 5H), 4.38 (d, 1H, J=3.5 Hz), 4.46 (d, 1H, J=8.0 Hz, H-1''''), 5.16 (s, 1H, H-1'''), 5.29 (s, 1H, H-1''), 5.96 (d, 1H, J=3.5 Hz, H-1').

$^{13}$C NMR: δ=29.7 (C-2), 42.2 (C-6'''), 42.6 (C-6'), 50.2, 51.7, 52.6, 54.1, 55.1, 62.0 (C-6''''), 69.2 (C-5''), 69.4, 69.8, 71.3, 72.0, 73.3, 73.7, 74.0, 74.2, 74.4, 75.2, 75.3, 76.9, 81.5, 87.0, 96.4 (C-1'''), 97.0 (C-1'), 104.8 (C-1''''), 112.6 (C-1'').

ESIMS m/z: 814.3 (M+K$^+$, $C_{29}H_{57}N_7O_{17}$ requires 814.3).

Compound X: The titled compound was prepared as was described for the preparation of Compound II with the following quantities: compound 16h (101.7 mg, 0.066 mmol), in 33% solution of MeNH$_2$ in EtOH (40 mL), THF (4.5 mL), NaOH 0.1M (0.5 mL), H$_2$O (0.5 mL), PMe$_3$ (1M solution in THF, (1.6 mL, 1.6 mmol), to yield of the free amine (48.2 mg, 80%). The product was dissolved in water and the pH was adjusted to 6.8 by H$_2$SO$_4$ (0.01 M), and the solution was lyophilized to afford the sulfate salt of Compound X as a white foamy solid.

NMR analyses were performed at 500 MHz, in D$_2$O, and at pH 3.45, adjusted by H$_2$SO$_4$).

$^1$H NMR: δ=1.93 (ddd, 1H, $J_1=J_2=J_3$=12.5 Hz, H-2 axial) 2.34 (broad dt, 1H, H-2 equatorial), 3.06-4.39 (m, 33H), 5.00 (d, 1H, J=2.5 Hz, H-1''''), 5.17 (s, 2H, C-1''', C-1''''), 5.31 (d, 1H, J=2.5 Hz, H-1''), 5.98 (d, 1H, J=3.5 Hz, H-1').

$^{13}$C NMR: δ=29.6 (C-2), 42.2 and 42.3 (C-6', C-6''', C6'''' could not be distinguished), 50.6, 51.6, 52.6, 52.7, 55.4, 63.3 (C-5''''), 69.0, 69.1, 69.4, 69.7, 70.5 (C-5''), 71.3, 72.0, 72.1, 72.9, 74.0, 74.7, 74.9, 76.5, 77.7, 79.0, 82.0, 80.1, 84.2, 87.0, 96.4 (C-1'), 97.0 and 97.5 (C-1''', C-1'''' could not be distinguished) 109.0 (C-1''''), 112.4 (C-1'').

MALDI-TOFMS: m/z=945.5 (M+K$^+$, $C_{34}H_{66}N_8O_{20}$ requires 945.9).

Compound XI: Compound 16i (0.164 gram, 0.11 mmol) was dissolved in 33% solution of MeNH$_2$ in EtOH (40 mL) and the mixture was stirred at room temperature for 24 hours. The reagent and the solvent were removed by evaporation and the residue was dissolved in THF (4 mL), NaOH 0.1M (1 mL) and stirred at room temperature for 10 minutes after which PMe$_3$ (1M solution in THF, 1.66 mL, 1.66 mmol) was added. Propagation of the reaction was monitored by TLC (CH$_2$Cl$_2$/MeOH/H$_2$O/MeNH$_2$, 33% solution in EtOH; 10:15:6:15), which indicated completion after 4.5 hours. The reaction mixture was purified by flash chromatography on a short column of silica and the column was washed as follows: THF, EtOAc, MeOH/EtOAc (1:1), MeOH, and finally the product was eluted with MeNH$_2$ (33% solution in EtOH). The fractions containing the product were evaporated under vacuum, re-dissolved in water and evaporated again to afford the free amine compound (61.2 mg, 73%). The product was then dissolved in water, and the pH was adjusted to 6.8 by H$_2$SO$_4$ (0.01 M), and the product was lyophilized to give the sulfate salt of Compound XI as a white foamy solid.

$^1$H NMR (500 MHz, D$_2$O, pH=3.04) data of XI are summarized in Table 15 hereinbelow.

$^{13}$C NMR: δ=29.6 (C-2), 35.2 (C-5''''), 42.2 (C-6'), 42.3 (C-6'''), 50.3, 51.6, 52.6, 55.3, 63.5 (C-5''), 69.0, 69.4, 69.7, 71.3, 72.1, 72.7, 73.0, 74.1, 75.0, 76.2, 76.4, 79.8, 82.1, 87.1, 87.2, 89.4 (C-1''''), 96.2 (C-1'''), 97.1 (C-1'), 112.5 (C-1'').

MALDI-TOFMS: m/z=801.1 (M+K$^+$, $C_{28}H_{54}N_6O_{16}S$ requires 801.3).

Compound XII: The titled compound was prepared as was described for the preparation of Compound XI with the following quantities: 16j (282 mg, 0.208 mmol), in 33% solution of MeNH$_2$ in EtOH (40 mL), THF (4.5 mL), NaOH 0.1M (1 mL), H$_2$O (1 mL), PMe$_3$ (1M solution in THF, (1.87 mL, 1.87 mmol), to yield of the free amine: 111.5 mg, (69%). The product was dissolved in water and the pH was adjusted to 6.8 by H$_2$SO$_4$ (0.01 M), and lyophilized to afford the sulfate salt of XII as a white foamy solid.

$^1$H NMR (500 MHz, D$_2$O, pH 4.2, adjusted by H$_2$SO$_4$ 0.01M) data of Compound XII are summarized in the attached Table 9.

$^{13}$C NMR (125 MHz, D$_2$O): δ=29.6 (C-2), 42.2 (C-6'''), 42.7 (C-6'), 50.1, 51.7, 52.6, 55.0, 62.3 (C-5''), 69.2 (C-6''''), 69.3, 69.4, 69.6, 71.3, 71.5, 72.0, 73.5, 74.1, 74.4, 74.8, 75.0, 76.7, 77.4, 77.6, 81.4, 87.0, 96.4 (C-1'), 97.0 (C-1'''), 104.9 (C-1''''), 112.6 (C-1'').

MALDI-TOFMS: m/z=815.2 (M+K$^+$, $C_{29}H_{56}N_6O_{16}$ requires 815.7).

Compounds IX and XIII: Lewis acid (BF$_3$.Et$_2$O) promoted coupling of the thiol acceptor 2 with the trichloroacetimidate donor 8e furnished the corresponding protected β-thioglycoside, which after two-steps deprotection, provided the designed thioglycoside 16i in 73% isolated yield. When the chromatographically pure thioacetate 2a was directly subjected to the same two-steps deprotection procedure, treatment with methylamine followed by Staudinger reaction, a mixture (a ratio of about 1:3) of Compound IX and the corresponding disulfide dimer Compound XIII were obtained in an overall yield of 88%. This mixture was purified on a Biogel P-2 column to yield the sufficiently pure Compounds IX and XIII for biological tests.

Compound 2a (250 mg, 0.231 mmol) was dissolved in 33% solution of MeNH$_2$ in EtOH (40 mL) and the mixture was stirred at room temperature for 24 hours. The reagent and the solvent were removed by evaporation and the residue was dissolved in THF (4 mL), NaOH 0.1M (1 mL) and stirred at 0° C. After 10 minutes, PMe$_3$ (1M solution in THF, 1.66 mL, 1.66 mmol) was added. Propagation of the reaction was monitored by TLC (CH$_2$Cl$_2$/MeOH/H$_2$O: MeNH$_2$ (33% solution in EtOH); 10:15:6:15), which indicated the full consumption of the starting material after 2.5 hours. At this point two products appeared on the TLC. The polar dimmer product appeared with the R$_f$ value of 0.16 and the less polar monomer appeared with the R$_f$ value of 0.54. The reaction mixture was purified by flash chromatography on a short column of silica gel and the column was washed as follows: THF, EtOAc, MeOH/EtOAc (1:1), MeOH, and finally the product was eluted with MeNH$_2$ (33% solution in EtOH). The fractions containing the mixture of monomer and dimmer products were evaporated under vacuum, re-dissolved in water and evaporated again to afford the mixture of free amines (128.3 mg, 88%). The mixture was then dissolved in water, the pH was adjusted to 6.8 by H$_2$SO$_4$ (0.01 M), and lyophilized to give the sulfate salts of the amines as a white foamy solid. The monomer and dimer were then separated using size exclusion chromatography (P-2 gel was packed in a column 47 cm length, 1.2 cm diameter column). The pure dimer Compound XIII and monomer Compound IX were then lyophilized.

Following are the data obtained in NMR and MS measurements of the pure thiol, Compound IX.

$^1$H NMR (500 MHz, D$_2$O pD=6.8): δ=1.45 (ddd, 1H, $J_1=J_2=J_3$=12.5 Hz, H2-ax), 2.08 (bd, 1H, J=12.0 Hz, H2-eq), 2.54 (dd, 1H, $J_1$=3.0, $J_2$=13.0 Hz, H5''), 2.66 (dd, 1H, $J_1$=9.0, $J_2$=13.0 Hz, H5''), 2.90-3.13 (m, 5H), 3.20-3.33 (m, 4H), 3.38 (bs, 1H), 3.47 (bt, 1H, J=9.0 Hz), 3.58 (bt, 1H, J=9.0 Hz), 3.64-3.75 (m, 3H), 3.87 (m, 1H), 4.06 (bs, 1H), 4.17 (bs, 1H), 4.27-4.37 (m, 3H), 5.11 (bs, 1H, H1'), 5.23 (bs, 1H, H1'''), 5.78 (bd, 1H, J=3.5 Hz, H1'').

$^{13}$C NMR (125 MHz, D$_2$O): δ=40.5, 40.7, 49.3, 50.6, 51.3, 54.3, 64.6, 68.0, 68.3, 69.2, 70.5, 71.2, 73.6, 73.7, 77.9, 80.1, 85.8, 96.6, 96.8, 110.6.

MALDI-TOF MS m/z 669.2 (M+K$^+$, $C_{28}H_{54}N_6O_{16}S$ requires 669.5).

Following are the data obtained in NMR and MS measurements of the pure thiol, Compound XIII.

$^1$H NMR (500 MHz, D$_2$O pD=6.8): δ=1.82 (m, 2H, H2axial), 2.26 (bd, J=12.0 Hz, 2H, H$_2$ equatorial), 2.80 (dd, 1H, $J_1$=8.5, $J_2$=13.0 Hz, H5''), 3.08 (dd, 1H, $J_1$=8.0, $J_2$=13.0

Hz, H5″), 3.13-3.36 (m, 12H), 3.60 (bt, 2H, J=10.0 Hz), 3.68 (bs, 2H), 3.83-3.92 (m, 2H), 3.99 (bt, 2H, J=9.5 Hz), 4.10 (bs, 2H), 4.19 (bs, 2H), 4.36-4.40 (m, 6H), 5.18 (bs, 2H, H1′), 5.33 (bs, 2H, H1‴), 5.93 (bd, 2H, J=3.0 Hz, H1′).

$^{13}$C NMR (125 MHz, D$_2$O): δ=40.3, 48.5, 49.8, 50.7, 53.6, 67.2, 67.6, 68.4, 69.2, 70.3, 70.9, 72.4, 73.2, 75.5, 78.4, 78.9, 85.3, 94.4 (C-1′), 95.3 (C-1‴), 110.1 (C-1″).

MALDI-TOF MS m/z 1298.5 (M+K$^+$, C$_{28}$H$_{54}$N$_6$O$_{16}$S requires 1298.2).

NMR Methods and Results $^1$H NMR, $^{13}$C NMR, DEPT, COSY, 2D TOCSY, 1D TOCSY, HMQC, HMBC spectra were recorded on a Bruker Advance 500 spectrometer, and chemical shifts reported (in ppm) are relative to internal Me$_4$Si (δ=0.0) with CDCl$_3$ as the solvent, and to HOD (δ=4.63) with D$_2$O as the solvent. Mass spectrometric analysis was performed using a Bruker Dal- tonix Apex 3 mass spectrometer using electron spray ionization (ESI), using a TSQ-70B mass spectrometer (Finnigan-MAT) or using matrix assisted laser desorption ionization with a time of flight mass detector (MALDI-TOF by Micromass) using α-cyano-4-hydrocinnamic acid as a matrix. Reactions were monitored by TLC on Silica Gel 60 F$_{254}$ (0.25 mm, Merck), and spots were visualized by charring with a yellow solution containing (NH$_4$)Mo$_7$O$_{24}$.4H$_2$O (120 grams) and (NH$_4$)$_2$Ce(NO$_3$)$_6$ (5 grams) in 10% H$_2$SO$_4$ (800 mL). Flash column chromatography was performed on Silica Gel 60 (70-230 mesh). All reactions were carried out under an argon atmosphere with anhydrous solvents, unless otherwise noted. All chemicals unless otherwise stated, were obtained from commercial sources.

Chemical structures corresponding to the previously described compounds, followed by the NMR results for those structures, are given below.

TABLE 1

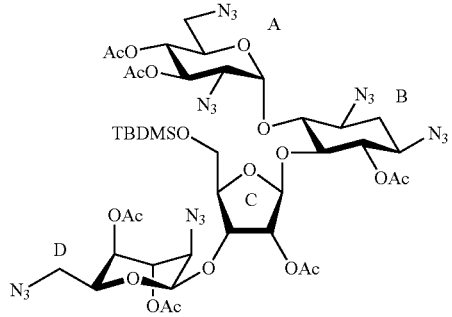

$^1$H NMR (500 MHz, CDCl$_3$) chemical shifts and coupling constants for the titled structure.[a]

| Ring | H1 | H2 | H3 | H4 | H5 | H5′ | H6 | H6′ |
|---|---|---|---|---|---|---|---|---|
| A | 6.09 | 3.14 | 5.45 | 4.92 | 4.42 | | 3.25-3.32 | 3.25-3.32 |
|   | d | dd | t | t | ddd | | m | m |
|   | J = 3.5 | J = 3.5, 10.5 | J = 9.5 | J = 10.0 | J = 3.0, 5.0, 8.5 | | | |
| C | 5.36 | 4.77 | 4.36 | 4.23 | 3.71 | 3.86 | | |
|   | d | t | t | dd | dd | m | | |
|   | J = 4.5 | J = 4.5 | J = 4.7 | J = 4.0, 6.0 | J = 4.5, 11.5 | | | |
| D | 4.79 | 3.25-3.32 | 5.00 | 4.67 | 3.49 | | 3.25-3.32 | 3.54 |
|   | d | m | t | s | ddd | | m | dd |
|   | J = 2.0 | | J = 3.0 | | J = 2.0, 4.5, 6.5 | | | J = 8.5, 13.0 |

| | H1 | H2eq | H2ax | H3 | H4 | H5 | H6 |
|---|---|---|---|---|---|---|---|
| B | 4.92 | 1.58 | 2.34 | 3.49 | 3.67 | 3.86 | 3.39 |
|   | t | ddd | dt | ddd | t | m | ddd |
|   | J = 1.0 | J$_1$ = J$_2$ = J$_3$ = 12.5 | J = 4.0, 13.5 | J$_1$ = J$_2$ = J$_3$ = 5.0 | J = 9.0 | | J = 4.0, 10.0, 12.5 |

[a]Values of chemical shifts are in ppm and values of coupling constants. are in Hz. The additional peaks in the spectrum were identified as follow: δ 0.06 (s, 3H, Me), 0.08 (s, 3H, Me), 1.07 (s, 9H, t-Bu), 2.01 (s, 3H, acetate), 2.03 (s, 3H, acetate), 2.06 (s, 3H, acetate), 2.12 (s, 3H, acetate), 2.14 (s, 3H, acetate), 2.16 (s, 3H, acetate).

TABLE 2

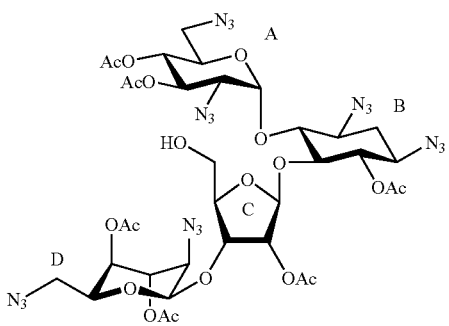

1

¹H NMR (500 MHz, CDCl₃) chemical shifts and coupling constants for the neomycin acceptor 1.ᵃ

| Ring | H1 | H2 | H3 | H4 | H5 | H5' | H6 | H6' |
|---|---|---|---|---|---|---|---|---|
| A | 6.02 d J = 4.0 | 3.21 dd J = 3.5, 10.5 | 5.61 dd J = 9.5, 10.5 | 5.08-5.15 m | 4.60 ddd J = 3.0, 5.5, 10.0 | | 3.47 dd J = 2.5, 13.5 | 3.40-3.42 m |
| C | 5.46 d J = 2.5 | 4.93 dd J = 3.0, 5.5 | 4.51 t J = 6.5 | 4.19-4.24 m | 4.02 dd J = 4.0, 12.5 | 3.83 dd J = 6.0, 12.5 | | |
| D | 4.99 d J = 1.5 | 3.40-3.42 m | 5.08-5.15 m | 4.80 s | 4.19-4.24 m | | 3.70 dd J = 8.5, 13.0 | 3.40-3.42 m |

| | H1 | H2eq | H2ax | H3 | H4 | H5 | H6 |
|---|---|---|---|---|---|---|---|
| B | 3.57 ddd J = 4.5, 10.5, 14.5 | 2.51 dt J = 4.5, 13.0 | 1.74 ddd J₁ = J₂ = 13.0, J₃ = 12.5 | 3.65 ddd J = 4.5, 10.0, 14.0 | 3.82 t J = 9.0 | 4.06 t J = 9.0 | 5.08-5.15 m |

ᵃValues of chemical shifts are in ppm and values of coupling constants are in Hz. The additional peaks in the spectrum were identified as follow: δ 1.85 (broad s, 1H, OH), 2.17 (s, 3H, acetate), 2.20 (s, 3H, acetate), 2.22 (s, 3H, acetate), 2.25 (s, 3H, acetate), 2.27 (s, 3H, acetate), 2.28 (s, 3H, acetate).

TABLE 3

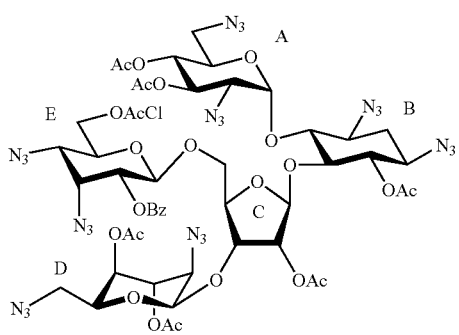

16a

¹H NMR (500 MHz, CDCl₃) chemical shifts and coupling constants for the protected pseudo-pentasaccharide 16a.ᵃ

| Ring | H1 | H2 | H3 | H4 | H5 | H5' | H6 | H6' |
|---|---|---|---|---|---|---|---|---|
| A | 6.12 d J = 3.5 | 3.24-3.30 m | 5.42 t J = 10 | 5.02 t J = 11.5 | 4.46-4.52 m | | 3.34-3.42 m | 3.63-3.67 m |
| C | 5.16 d J = 4.5 | 4.70 d J = 5 | 4.32 dd J = 6.5, 11.5 | 4.08 m | 3.71 dd J = 4.5, 11.5 | 3.86 bd | | |

TABLE 3-continued

| | | | | | | | | |
|---|---|---|---|---|---|---|---|---|
| D | 4.46-4.52 | 3.12 | 4.96 | 4.64 | 3.63-3.67 | | 3.34-3.42 | 3.52-3.56 |
| | m | bs | s | s | m | | m | m |
| E | 4.86 | 5.28 | 4.46-4.52 | 4.91 | 4.96 | | 4.46-4.52 | 4.40 |
| | d | dd | m | bdd | dd | | m | dd |
| | J = 8.0 | J = 3.0, 7.5 | | | $J_1$ = 2.0, 12.5 | | | J = 4.5, 12.5 |

| | H1 | H2eq | H2ax | H3 | H4 | H5 | H6 |
|---|---|---|---|---|---|---|---|
| B | 3.34-3.42 | 2.31 | 1.55 | 3.24-3.30 | 4.73 | 3.75 | 3.69 |
| | m | m | ddd | m | t | t | t |
| | | | $J_1 = J_2 = $ | | J = 11.0 | J = 9.5 | J = 9.0 |
| | | | $J_3 = 12.5$ | | | | |

[a]Values of chemical shifts are in ppm and values of coupling constants are in Hz. The additional peaks in the spectrum were identified as follow: δ 2.04 (s, 3H, acetate), 2.05 (s, 3H, acetate), 2.06 (s, 3H, acetate), 2.08 (s, 3H, acetate), 2.14 (s, 3H, acetate), 2.15 (s, 3H, acetate) 4.23 (s, 2H, chloroacetate), 7.57 (t, 2H, meta benzoyl protons), 7.65(t, 1H, para benzoyl proton), 8.06 (d, 2H, ortho benzoyl protons).

TABLE 4

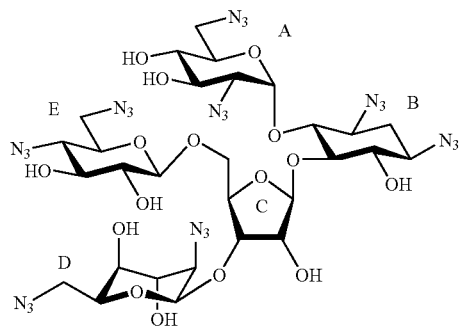

$^1$H NMR (500 MHz, CDCl$_3$) chemical shifts and coupling constants for the titled structure.[a]

| Ring | H1 | H2 | H3 | H4 | H5 | H5' | H6 | H6' |
|---|---|---|---|---|---|---|---|---|
| A | 5.77 | 3.22-3.29 | 3.77 | 3.22-3.29 | 3.98 | | 3.49 | 3.40 |
| | d | m | t | m | ddd | | dd | dd |
| | J = 4.0 | | J = 9.0 | | J = 3.0, 6.0, 9.5 | | J = 2.5, 9.5 | J = 4.5, 13.0 |
| C | 5.18 | 4.04 | 4.24 | 4.13-4.14 | 3.43-3.49 | 3.43-3.49 | | |
| | d | dd | dd | m | m | m | | |
| | J = 4 | $J_1 = J_2 = $ 4.0 | $J_1 = J_2 = $ 4.5 | | | | | |
| D | 4.98 | 3.68 | 3.87 | 3.21-3.25 | 3.90-3.92 | | 3.54-3.59 | 3.21-3.29 |
| | d | bs | s | m | m | | m | m |
| | J = 1.0 | | | | | | | |
| E | 4.21 | 3.24-3.3 | 3.46-3.49 | 3.24-3.3 | 3.36-3.39 | | 3.36-3.39 | 3.36-3.39 |
| | d | m | m | m | m | | m | m |
| | J = 8.5 | | | | | | | |

| | H1 | H2eq | H2ax | H3 | H4 | H5 | H6 |
|---|---|---|---|---|---|---|---|
| B | 3.24-3.36 | 2.13 | 1.55 | 3.24-3.36 | 3.24-3.36 | 3.54-3.57 | 3.48 |
| | m | dt | ddd | m | m | m | t |
| | | J = 4.5, 13.0 | $J_1 = J_2 = $ $J_3 = 12.5$ | | | | J = 8.5 |

[a]Values of chemical shifts are in ppm and values of coupling constants are in Hz.

TABLE 5

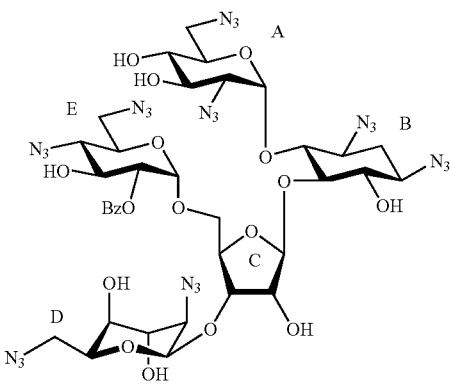

¹H NMR (500 MHz, CDCl₃) chemical shifts and coupling constants for the titled structure.[a]

| Ring | H1 | H2 | H3 | H4 | H5 | H5' | H6 | H6' |
|---|---|---|---|---|---|---|---|---|
| A | 5.73 d J = 4.0 | 3.09-3.13 m | 3.77 t J = 8.5 | 3.26-3.3 m | 3.98 ddd J = 2.0, 5.5, 8.5 | | 3.47 bd | 3.39 dd J = 5.5, 14.5 |
| C | 5.36 d J = 4.5 | 4.77 t J = 4.5 | 4.36 t J = 4.7 | 4.23 dd J = 4.0, 6.0 | 3.71 dd J = 4.5, 11.5 | 3.86 m | | |
| D | 4.99 d J = 1.0 | 3.66 bs | 3.86 bs | 3.27 bs | 3.41-3.52 m | | 3.41-3.52 m | 3.41-3.52 m |
| E | 5.86 d J = 5.5 | 4.85 dd J₁ = J₂ = 4.5 | 4.85 dd J = 5.2, 5.3 | 3.33-3.39 m | 3.42-3.46 m | | 3.33-3.39 m | 3.23 dd J = 3.0, 17.0 |

| Ring | H1 | H2eq | H2ax | H3 | H4 | H5 | H6 |
|---|---|---|---|---|---|---|---|
| B | 3.26-3.36 m | 2.12 dt J = 4.0, J₃ 13.0 | 1.31 ddd J₁ = J₂ = 12.5 | 3.26-3.36 m | 3.51-3.61 m | 3.51-3.61 m. | 3.41 t J = 9.0 |

[a]Values of chemical shifts are in ppm and values of coupling constants are in Hz. The additional peaks in the spectrum were identified as follow: δ 7.2-7.32 (m, 3H, benzoyl), 7.53-7.55(m, 2H, benzoyl).

TABLE 6

16c

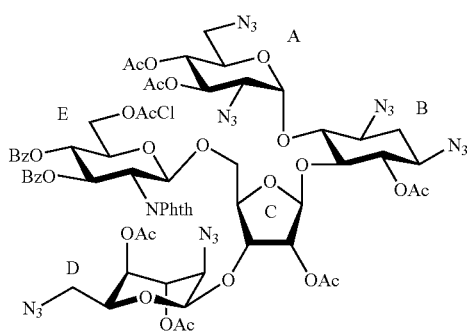

¹H NMR (500 MHz, CDCl₃) chemical shifts and coupling constants for the protected pseudo-pentasaccharide 16c.[a]

| Ring | H1 | H2 | H3 | H4 | H5 | H5' | H6 | H6' |
|---|---|---|---|---|---|---|---|---|
| A | 6.04 d J = 4.0 | 3.38-3.42 m | 5.51 dd J = 9.5, 10.5 | 5.08 t J = 9.5 | 4.50-4.59 m | | 3.42-3.53 m | 3.42-3.53 m |

TABLE 6-continued

| | | | | | | | | |
|---|---|---|---|---|---|---|---|---|
| C | 5.23 d J = 3.0 | 4.50-4.59 m | 4.13-4.16 m | 4.28 ddd J = 3.0, 5.0, 6.5 | 3.73 dd J = 4.5, 12.5 | 4.13-4.16 m | | |
| D | 4.68 d J = 2.5 | 3.25 bs | 5.08 t J = 3.0 | 4.70 bs | 4.03 ddd J = 1.5, 5.0, 6.0 | | 3.42-3.53 m | 3.38-3.42 m |
| E | 5.62 d J = 8.5 | 4.64 dd J = 8.5, 11.0 | 6.62 dd J = 9.0, 10.5 | 5.62 dd J = 9.5, 13.0 | 4.13-4.16 m | | 4.40 dd J = 3.0, 12.5 | 4.50-4.59 m |

| | H1 | H2eq | H2ax | H3 | H4 | H5 | H6 |
|---|---|---|---|---|---|---|---|
| B | 3.38-3.42 m | 2.12 dt J = 4.5, 13.0 | 1.75 ddd $J_1 = J_2 =$ $J_3 = 12.5$ | 3.42-3.53 m | 4.92 t J = 10.0 | 3.89 t J = 8.5 | 3.82 t J = 8.5 |

[a]Values of chemical shifts are in ppm and values of coupling constants are in Hz. The additional peaks in the spectrum were identified as follow: δ 1.98 (s, 3H, acetate), 2.09 (s, 3H, acetate), 2.10 (s, 3H, acetate), 2.16 (s, 3H, acetate), 2.165 (s, 3H, acetate), 2.19 (s, 3H, acetate) 4.17 (s, 2H, chloroacetate), 7.24-7.92(m, 14H, aromatic).

TABLE 7

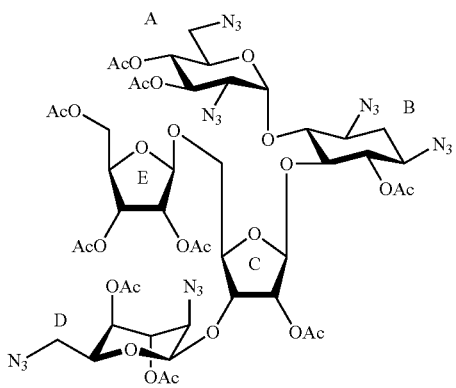

16d $^1$H NMR (500 MHz, CDCl$_3$) chemical shifts and coupling constants for the protected pseudo-pentasaccharide 16d.[a]

| Ring | H1 | H2 | H3 | H4 | H5 | H5' | H6 | H6' |
|---|---|---|---|---|---|---|---|---|
| A | 6.06 d J = 4.0 | 3.21-3.31 m | 3.71 dd J = 9.5, 11.0 | 4.89-4.95 m | 3.40 ddd J = 3.5, 5.0, 10.0 | 3.27-3.34 m | 3.27-3.34 m | |
| C | 5.33 d J = 4.5 | 4.79 dd $J_1 = J_2 =$ 4.5 | 4.35-4.37 m | 4.28-4.31 m | 3.45 dd J = 3.5, 10.0 | 3.74 dd J = 2.0, 10.0 | | |
| D | 4.83 d J = 4.0 | 3.27-3.34 m | 4.66 bs | 4.97 dd $J_1 = J_2 = 4.5$ | 4.05 ddd J = 2.0, 5.0, 6.5 | | 3.59 dd J = 8.5, 13.0 | 3.74 dd J = 4.0, 12.0 |
| E | 5.95 d J = 4.5 | 4.92 dd J = 3.5, 5.5 | 4.92 dd J = 3.5, 5.5 | 4.12-4.20 m | 4.12-4.20 m | 4.35-4.37 m | | |

| | H1 | H2eq | H2ax | H3 | H4 | H5 | H6 |
|---|---|---|---|---|---|---|---|
| B | 3.40 ddd J = 4.5, 10.5, 12.0 | 2.33 dt J = 4.0, 13.5 | 1.58 ddd $J_1 = J_2 =$ $J_3 = 12.5$ | 3.50 ddd J = 4.0, 10.0, 12.5 | 4.93 t J = 12.0 | 3.88 t J = 9.5 | 3.66 t J = 9.0 |

[a]Values of chemical shifts are in ppm and values of coupling constants are in Hz. The additional peaks in the spectrum were identified as follow: δ 2.00 (s, 3H, acetate), 2.05 (s, 6H, 2 acetates), 2.06 (s, 3H, acetate), 2.07 (s, 3H, acetate), 2.10 (s, 3H, acetate), 2.11 (s, 3H, acetate), 2.13 (s, 3H, acetate), 2.16 (s, 3H, acetate).

TABLE 8

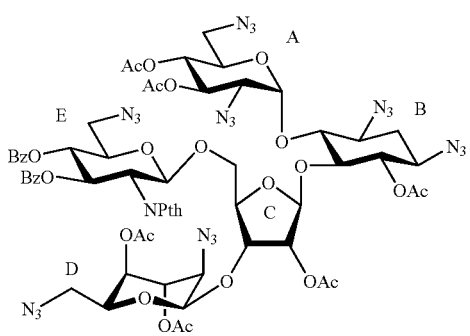

16g $^1$H NMR (500 MHz, CDCl$_3$) chemical shifts and coupling constants for the titled structure.[a]

| Ring | H1 | H2 | H3 | H4 | H5 | H5' | H6 | H6' |
|---|---|---|---|---|---|---|---|---|
| A | 6.15<br>d<br>J = 3.5 | 3.44-3.62<br>m | 5.52<br>t<br>J = 10.5 | 5.18<br>t<br>J = 10.0 | 4.60-4.64<br>m | | 3.44-3.62<br>m | 3.44-3.62<br>m |
| C | 5.24<br>d<br>J = 2.5 | 4.47<br>dd<br>J = 2.5,<br>4.5 | 4.16<br>t<br>J = 4.5 | 4.33<br>bdd | 3.73<br>dd<br>J = 3.5,<br>11.0 | 4.22<br>dd<br>J = 2.5,<br>11.0 | | |
| D | 4.99<br>d<br>J = 1.0 | 3.23<br>bs | 3.86<br>bs | 4.66-4.70<br>m | 3.98-4.03<br>m | | 3.41-3.52<br>m | 3.44-3.62<br>m |
| E | 4.60-4.64<br>m | 4.66-4.70<br>m | 6.26<br>t<br>J = 10.5 | 5.57<br>t<br>J = 9.5 | 4.10<br>ddd<br>J = 2.5,<br>7.5, 13.5 | | 3.27<br>dd<br>J = 5.5,<br>13.0 | 3.44-3.62<br>m |

| | H1 | H2eq | H2ax | H3 | H4 | H5 | H6 |
|---|---|---|---|---|---|---|---|
| B | 3.37<br>ddd<br>J = 4.5,<br>10.5, 13.5 | 2.41<br>dt<br>J = 4.5,<br>13.0 | 1.81<br>ddd<br>J$_1$ = J$_2$ = J$_3$<br>J$_3$ = 12.5 | 3.44-3.62<br>m | 3.98-4.03<br>m | 3.82<br>t<br>J = 9.0 | 4.96<br>t<br>J = 10.0 |

[a]Values of chemical shifts are in ppm and values of coupling constants are in Hz. The additional peaks in the spectrum were identified as follow: δ 1.94 (s, 3H, acetate), 2.08 (s, 3H, acetate), 2.10 (s, 3H, acetate), 2.14 (s, 3H, acetate), 2.17 (s, 3H, acetate), 2.18 (s, 3H, acetate), 7.29-8.10 (14H, aromatic protons).

TABLE 9

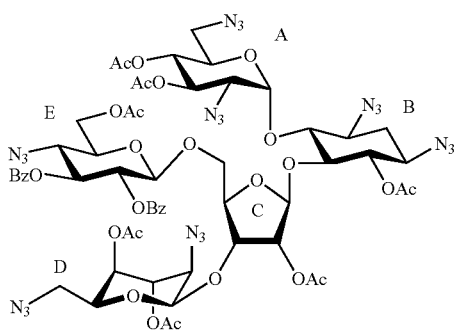

16f $^1$H NMR (500 MHz, CDCl$_3$) chemical shifts and coupling constants for the titled structure.[a]

| Ring | H1 | H2 | H3 | H4 | H5 | H5' | H6 | H6' |
|---|---|---|---|---|---|---|---|---|
| A | 6.14<br>d<br>J = 3.5 | 328-3.35<br>m | 5.47<br>t<br>J = 9.0 | 5.09<br>t<br>J = 9.5 | 3.98<br>ddd<br>J = 3.0,<br>3.0, 10.0 | | 3.41-3.52<br>m | 3.41-3.52<br>m |

TABLE 9-continued

| | | | | | | | | |
|---|---|---|---|---|---|---|---|---|
| C | 5.17 s | 4.71 d J = 5.0 | 4.27 dd J = 4.5, 7.0 | 4.08 m | 4.25 dd J = 1.0, 11.0 | 3.55-3.65 m | | |
| D | 4.36 d J = 1.5 | 4.92 t J = 2.0 | 4.60 bs | 3.41-3.52 m | 3.13 bt | | 3.28-3.35 m | 3.41-3.52 m |
| E | 4.66 d J = 8.0 | 5.45 t J = 10.0 | 5.59 t J = 10.0 | 3.99 t J = 10.0 | 3.55-3.65 m | | 4.45 dd J = 1.5, 11.5 | 4.40 dd J = 5.0, 12.0 |

| | H1 | H2eq | H2ax | H3 | H4 | H5 | H6 |
|---|---|---|---|---|---|---|---|
| B | 3.28-3.35 m | 2.34 dt J = 4.0, 13.0 | 1.65 ddd $J_1 = J_2 = J_3$ $J_3 = 12.5$ | 3.41-3.52 m | 3.93 t J = 9.5 | 377 t J = 9.0 | 3.86 t J = 9.5 |

[a]Values of chemical shifts are in ppm and values of coupling constants are in Hz. The additional peaks in the spectrum were identified as follow: δ 1.98 (s, 3H, acetate), 2.06 (s, 3H, acetate), 2.07 (s, 3H, acetate), 2.10 (s, 3H, acetate), 2.12 (s, 3H, acetate), 2.14 (s, 3H, acetate), 2.19 (s, 3H, acetate), 7.60 (t, J = 7.5 Hz, 2H, meta benzoyl protons), 7.69 (t, J = 8.0 Hz, 2H, meta benzoyl protons), 7.77 (t, J = 7.5 Hz, 1H, para benzoyl proton), 7.84 (t, J = 7.5 Hz, 1H, para benzoyl proton), 8.15 (d, J = 8.5 Hz, 1H, ortho benzoyl proton). 8.30 (d, J = 7.5 Hz, 1H, ortho benzoyl proton).

TABLE 10

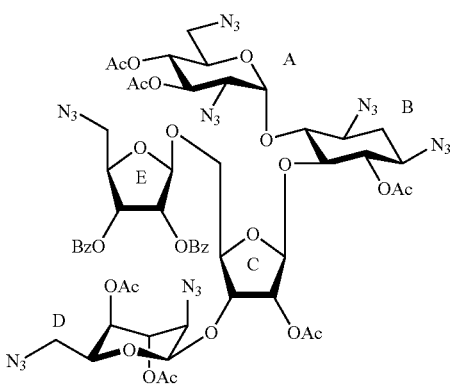

16e $^1$H NMR (500 MHz, CDCl$_3$) chemical shifts and coupling constants for the titled structure.[a]

| Ring | H1 | H2 | H3 | H4 | H5 | H5' | H6 | H6' |
|---|---|---|---|---|---|---|---|---|
| A | 5.73 d J = 4.0 | 3.09-3.13 m | 3.77 t J = 8.5 | 3.26-3.3 m | 3.98 ddd J = 2.0, 5.5, 8.5 | | 3.47 bd | 3.39 dd J = 5.5, 14.5 |
| C | 5.36 d J = 4.5 | 4.77 t J = 4.5 | 4.36 t J = 4.7 | 4.23 dd J = 4.0, 6.0 | 3.71 dd J = 4.5, 11.5 | 3.86 m | | |
| D | 4.99 d J = 1.0 | 3.66 bs | 3.86 bs | 3.27 bs | 3.41-3.52 m | | 3.41-3.52 m | 3.41-3.52 m |
| E | 5.86 d J = 5.5 | 4.85 dd $J_1 = J_2 =$ 4.5 | 4.85 dd J = 5.2, 5.3 | 3.33-3.39 m | 3.42-3.46 m | | 3.33-3.39 m | 3.23 dd J = 3.0, 17.0 |

TABLE 10-continued

|   | H1 | H2eq | H2ax | H3 | H4 | H5 | H6 |
|---|---|---|---|---|---|---|---|
| B | 3.26-3.36 | 2.12 | 1.31 | 3.26-3.36 | 3.51-3.61 | 3.51-3.61 | 3.41 |
|   | m | dt | ddd | m | m | m | t |
|   |   | J = 4.0, | $J_1 = J_2 = J_3$ |   |   |   | J = 9.0 |
|   |   | 13.0 | $J_3 = 12.5$ |   |   |   |   |

*a*Values of chemical shifts are in ppm and values of coupling constants are in Hz. The additional peaks in the spectrum were identified as follow: δ 1.99 (s, 3H, acetate), 2.02 (s, 3H, acetate), 2.03 (s, 3H, acetate), 2.04 (s, 3H, acetate), 2.12 (s, 3H, acetate), 2.13 (s, 3H, acetate), 7.29-8.10 (10H, meta aromatic benzoyl protons).

TABLE 11

16h $^1$H NMR (500 MHz, CDCl$_3$) chemical shifts and coupling constants for the titled structure.*a*

| Ring | H1 | H2 | H3 | H4 | H5 | H5' | H6 | H6' |
|---|---|---|---|---|---|---|---|---|
| A | 5.91 | 3.24-3.35 | 5.49 | 4.93-5.04 | 4.43-4.46 |   | 3.24-3.35 | 3.24-3.35 |
|   | d | m | dd | m | m |   | m | m |
|   | J = 3.5 |   | $J_1 = J_2 = 10.5$ |   |   |   |   |   |
| C | 5.34 | 4.93-5.04 | 4.07-4.24 | 4.07-4.24 | 3.59-3.66 | 4.07-4.24 |   |   |
|   | d | m | m | m | m | m |   |   |
|   | J = 1.0 |   |   |   |   |   |   |   |
| D | 4.89 | 3.24-3.35 | 4.93-5.04 | 4.71-4.72 | 4.07-4.24 |   | 3.48 | 3.19 |
|   | d | m | m | m | m |   | dd | dd |
|   | J = 1.5 |   |   |   |   |   | J = 5.0, | $J_1 = 4.0$ |
|   |   |   |   |   |   |   | 13.0 | $J_2 = 13.0$ |
| E | 5.17 | 5.23 | 4.61 | 4.29-4.32 | 4.43-4.46 | 4.07-4.24 |   |   |
|   | s | d | dd | m | m | m |   |   |
|   |   | J = 4.5 | J = 4.5, 7.5 |   |   |   |   |   |
| F | 4.93-5.04 | 3.24-3.35 | 4.93-5.04 | 4.71-4.72 | 4.07-4.24 |   | 3.59-3.66 | 3.24-3.35 |
|   | m | m | m | m | m |   | m | m |

|   | H1 | H2eq | H2ax | H3 | H4 | H5 | H6 |
|---|---|---|---|---|---|---|---|
| B | 3.59 | 2.39 | 1.64 | 3.48 | 3.71 | 3.91 | 4.93-5.04 |
|   | m | dt | ddd | m | t | t | m |
|   |   | J = 4.5, | $J_1 = J_2 = J_3 =$ |   | J = 9.0 | J = 9.0 |   |
|   |   | 13.0 | 13.0 |   |   |   |   |

*a*Values of chemical shifts are in ppm and values of coupling constants are in Hz. The additional peaks in the spectrum were identified as follow: δ 2.07 (s, 3H, acetate), 2.09 (s, 3H, acetate), 2.11 (s, 3H, acetates), 2.12 (s, 3H, acetate), 2.14 (s, 3H, acetate), 2.16 (s, 6H, acetate), 2.17 (s, 6H, acetates), 2.18 (s, 6H, acetate), 2.19 (s, 6H, acetate).

TABLE 12

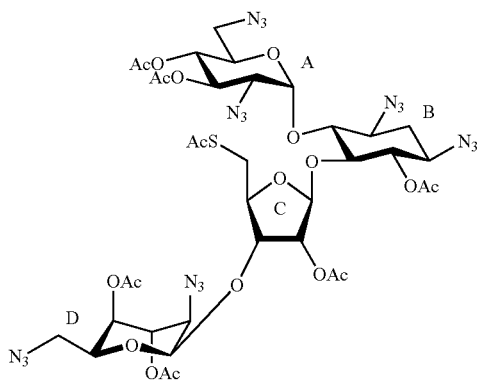

¹H NMR (500 MHz, CDCl₃) chemical shifts and coupling constants for the titled structure.[a]

| Ring | H1 | H2 | H3 | H4 | H5 | H5' | H6 | H6' |
|---|---|---|---|---|---|---|---|---|
| A | 5.93<br>d<br>J = 3.5 | 3.26-3.45<br>m | 5.48<br>t<br>J = 10.0 | 5.02-5.05<br>m | 4.44<br>ddd<br>J = 3.5, 6.5, 10.0 | | 3.26-3.45<br>m | 3.26-3.45<br>m |
| C | 5.28<br>d<br>J = 4.0 | 4.69-4.71<br>m | 5.48<br>t<br>J = 6.0 | 4.30<br>dd<br>J = 4.0, 8.0 | 4.05-4.08<br>m | 4.05-4.08<br>m | | |
| D | 4.81<br>s | 3.26-3.45<br>m | 4.69-4.71<br>m | 5.02-5.05<br>m | 3.64<br>dd<br>J = 7.5, 13.0 | | 3.26-3.45<br>m | 3.26-3.45<br>m |

| Ring | H1 | H2ax | H2eq | H3 | H4 | H5 | H6 |
|---|---|---|---|---|---|---|---|
| B | 3.26-3.45<br>m | 1.59<br>ddd<br>J₁ = J₂ = J₃ = 12.5 | 2.39<br>m | 3.49<br>ddd<br>J = 4.5, 8.5, 16.5 | 3.70<br>t<br>J = 9.5 | 3.88<br>t<br>J = 9.0 | 3.69<br>t<br>J = 10.5 |

[a]Values of chemical shifts are in ppm and values of coupling constants are in Hz. The additional peaks in the spectrum were identified as follow: δ 2.05 (s, 3H, acetate), 2.08 (s, 6H, acetate), 2.14 (s, 3H, acetate), 2.15 (s, 3H, acetate), 2.16 (s, 3H, acetate), 2.36 (s, 3H, MeSAc).

TABLE 13

2

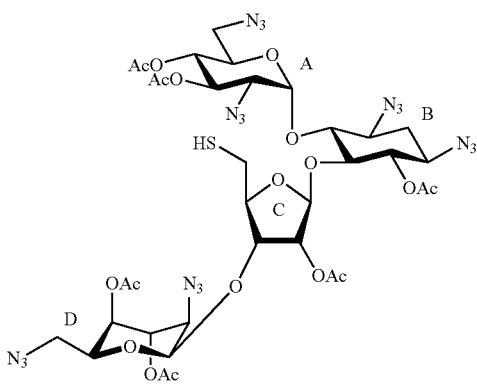

¹H NMR (500 MHz, CDCl₃) chemical shifts and coupling constants for the titled structure.[a]

| Ring | H1 | H2 | H3 | H4 | H5 | H5' | H6 | H6' |
|---|---|---|---|---|---|---|---|---|
| A | 5.94<br>d<br>J = 4.0 | 3.20-3.28<br>m | 5.45<br>t<br>J = 10.0 | 4.96-4.98<br>m | 4.40<br>ddd<br>J = 3.0, 6.0, 10.0 | | 3.20-3.28<br>m | 3.31<br>dd<br>J = 2.0, 13.0 |

TABLE 13-continued

| | | | | | | | | |
|---|---|---|---|---|---|---|---|---|
| C | 5.28 d J = 2.5 | 4.83 s (broad) | 4.29 t J = 5.5 | 4.11 m | 2.76 ddd J = 7.5, 14.0, 18.5 | 2.91 ddd J = 3.0, 8.5, 18.0 | | |
| D | 4.99 d J = 1.5 | 3.47 dd J = 2.5, 13.5 | 4.96-4.98 m | 4.65 s | 4.06 m | | 3.20-3.28 m | 3.54 dd J = 8.0, 13.0 |

| | H1 | H2eq | H2ax | H3 | H4 | H5 | H6 |
|---|---|---|---|---|---|---|---|
| B | 3.40 ddd J = 4.5, 10.5, 14.5 | 2.51 dt J = 4.0, 13.0 | 1.56 ddd $J_1 = J_2 = J_3 =$ 13.0 | 3.50 ddd J = 4.5, 12.5 | 3.67 t J = 9.0 10.0, 14.0 | 3.87 t J = 9.0 | 4.91 t J = 9.5 |

[a]Values of chemical shifts are in ppm and values of coupling constants are in Hz. The additional peaks in the spectrum were identified as follow: δ 1.78 (t, J = 8.0 Hz, 1H, SH), 2.00 (s, 3H, acetate), 2.04 (s, 3H, acetate), 2.05 (s, 3H, acetate), 2.10 (s, 6H, acetate), 2.12 (s, 3H, acetate),

TABLE 14

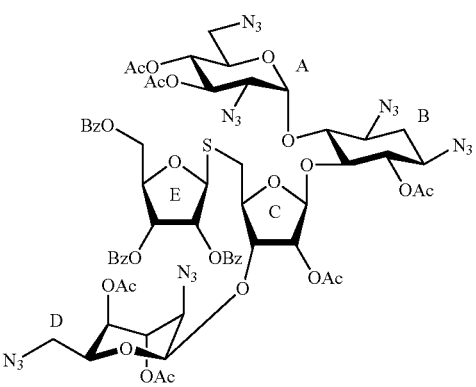

16i $^1$H NMR (500 MHz, CDCl$_3$) chemical shifts and coupling constants for the titled structure.[a]

| Ring | H1 | H2 | H3 | H4 | H5 | H5' | H6 | H6' |
|---|---|---|---|---|---|---|---|---|
| A | 5.91 d J = 5.5 | 3.24-3.33 m | 5.44 t J = 10.5 | 4.96-5.04 m | 3.41 ddd J = 3.0, 5.5, 9.5 | | 3.24-3.33 m | 3.24-3.33 m |
| C | 5.23 d J = 1.0 | 4.87-4.91 m | 4.28 bs | 4.28 bs | 3.14 m | 3.01 dd J = 7.5, 13.5 | | |
| D | 4.87-4.91 m | 3.24-3.33 m | 4.96 s | 4.64 s | 3.63-3.67 m | | 3.14 m | 3.52-3.56 m |
| E | 5.61 d J = 2.0 | 5.76 dd J = 2.0, 5.0 | 5.95 dd J = 5.5, 6.0 | 4.65-4.73 m | 4.65-4.73 m | 4.60 dd J = 5.0, 12.0 | | |

| | H1 | H2eq | H2ax | H3 | H4 | H5 | H6 |
|---|---|---|---|---|---|---|---|
| B | 3.24-3.33 m | 2.51 dt J = 5.0, 13.0 | 1.55 ddd $J_1 = J_2 = J_3 =$ 12.5 | 3.41 ddd J = 4.5, 10.0, 14.0 | 3.76 t J = 9.0 | 3.62 t J = 9.0 | 4.87-4.91 m |

[a]Values of chemical shifts are in ppm and values of coupling constants are in Hz. The additional peaks in the spectrum were identified as follow: δ 1.99 (s, 3H, acetate), 2.02 (s, 3H, acetate), 2.03 (s, 3H, acetate), 2.04 (s, 3H, acetate), 2.12 (s, 3H, acetate), 2.13 (s, 3H, acetate), 7.29-8.10 (10H, aromatic benzoyl protons).

TABLE 15

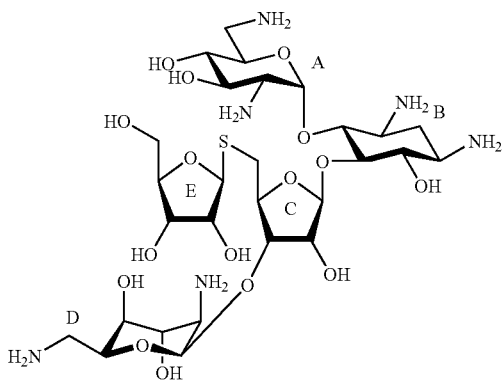

XI $^1$H NMR (500 MHz, D$_2$O pH = 3.04) chemical shifts and coupling constants for the titled structure.[a]

| Ring | H1 | H2 | H3 | H4 | H5 | H5' | H6 | H6' |
|---|---|---|---|---|---|---|---|---|
| A | 6.03 d J = 4.0 | 3.43-3.47 m | 3.95-3.99 m | 3.23-3.39 m | 3.80-3.89 m | | 3.14 dd J = 7.5, 13.5 | 3.23-3.39 m |
| C | 5.31 bs | 4.37 bs | 4.40 bt J = 5.0 | 4.26 bdd | 3.53 dd J = 6.0, 12.5 | 3.61-3.65 m | | |
| D | 5.19 bs | 3.43-3.47 m | 4.11-4.15 m | 3.68 bs | 4.21 bt | | 3.23-3.39 m | 3.23-3.39 m |
| E | 4.96 d J = 6.0 | 3.95-3.99 m | 4.03 t J = 4.0 | 3.80-3.89 m | 3.36-3.39 m | 2.86 dd J = 8.0, 13.5 | | |

| | H1 | H2eq | H2ax | H3 | H4 | H5 | H6 |
|---|---|---|---|---|---|---|---|
| B | 3.23-3.39 m | 2.35 bdt | 1.95 ddd $J_1 = J_2 = J_3 =$ 12.5 | 3.43-3.47 m | 3.61-3.65 m | 3.80-3.89 m | 4.11-4.15 m |

[a]Values of chemical shifts are in ppm and values of coupling constants are in Hz.

TABLE 16

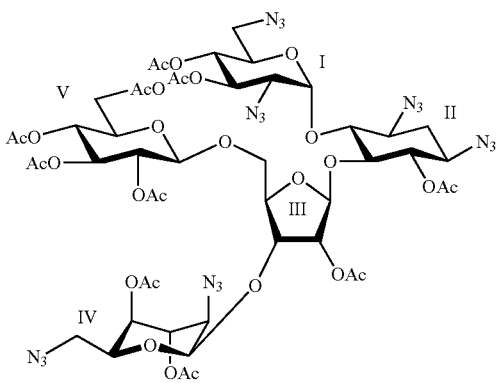

$^1$H NMR (500 MHz, CDCl$_3$) chemical shifts and coupling constants for the titled structure.[a]

| Ring | H1 | H2 | H3 | H4 | H5 | H5' | H6 | H6' |
|---|---|---|---|---|---|---|---|---|
| A | 6.21 d J = 3.5 | 3.31-3.38 m | 5.47 t J = 9.0 | 5.09 t J = 9.5 | 3.98 ddd J = 3.0, 3.0, 10.0 | | 3.40-3.48 m | 3.42 dd J = 2.5, 11.5 |

TABLE 16-continued

| | | | | | | | | |
|---|---|---|---|---|---|---|---|---|
| C | 5.22 d J = 1.0 | 4.74 d J = 5.0 | 4.27 dd J = 5.0, 6.5 | 4.30 dd J = 5.0, 7.5 | 4.25 dd J = 1.0, 11.0 | 3.58-3.67 m | | |
| D | 4.38 d J = 1.5 | 4.89 t J = 2.0 | 4.60 bs | 3.41-3.52 m | 3.15 t J = 2.5 | | 3.31-3.38 m | 3.41-3.52 m |
| E | 4.72 d J = 9.5 | 5.06 t J = 10.0 | 5.34 t J = 10.0 | 5.18 t J = 10.0 | 3.58-3.67 m | | 4.47 dd J = 1.5, 11.5 | 4.42 dd J = 4.0, 11.5 |

| | H1 | H2eq | H2ax | H3 | H4 | H5 | H6 |
|---|---|---|---|---|---|---|---|
| B | 3.31-3.38 m | 2.37 dt J = 4.5, 12.5 | 1.58 ddd $J_1 = J_2 = J_3 =$ 12.5 | 3.41-3.52 m | 3.93 t J = 9.5 | 3.77 t J = 9.0 | 3.86 t J = 9.5 |

[a]Values of chemical shifts are in ppm and values of coupling constants are in Hz. The additional peaks in the spectrum were identified as follow: δ 1.97 (s, 3H, acetate), 1.99 (s, 3H, acetate) 2.08 (s, 3H, acetate), 2.10 (s, 6H, acetate), 2.13 (s, 3H, acetate), 2.14 (s, 3H, acetate), 2.16 (s, 6H, acetate), 2.18 (s, 3H, acetate),

TABLE 17

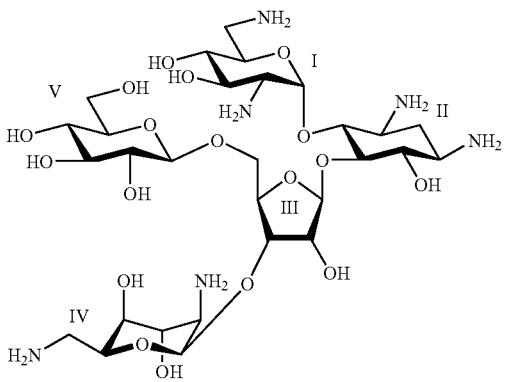

$^1$H NMR (500 MHz, CDCl$_3$) chemical shifts and coupling constants for the titled structure.[a]

| Ring | H1 | H2 | H3 | H4 | H5 | H5' | H6 | H6' |
|---|---|---|---|---|---|---|---|---|
| A | 5.95 d J = 3.5 | 3.49-3.68 m | 3.91 t J = 10.0 | 3.15-3.44 m | 3.71-3.91 m | | 3.49-3.68 m | 3.15-3.44 m |
| C | 5.28 d J = 2.5 | 4.37 d J = 2.0 | 4.64 m | 4.08-4.25 m | 3.49-3.65 m | 4.08-4.25 m | | |
| D | 5.15 d J = 1.0 | 3.15-3.44 m | 4.08-4.25 m | 3.49-3.68 m | 4.08-4.25 m | | 3.15-3.44 m | 3.15-3.44 m |
| E | 4.36 d J = 8.0 | 3.15-3.44 m | 3.15-3.44 m | 3.15-3.44 m | 3.49-3.68 m | | 3.71-3.91 m | 3.44-3.62 m |

| | H1 | H2eq | H2ax | H3 | H4 | H5 | H6 |
|---|---|---|---|---|---|---|---|
| B | 3.15-3.44 m | 2.32 m | 1.94 ddd $J_1 = J_2 = J_3 =$ 12.5 | 3.15-3.44 m | 3.15-3.44 m | 3.71-3.91 m | 4.08-4.25 m |

[a]Values of chemical shifts are in ppm and values of coupling constants are in Hz.

EXAMPLE 4

Additional Synthetic Strategies for Other Selected Compounds of the Present Invention Example 3 above related to a synthetic strategy for specific selected compounds according to the present invention. However, this strategy may optionally be generalized to obtain any member of the set4-set5 structures shown in FIG. 9.

Figure 13:
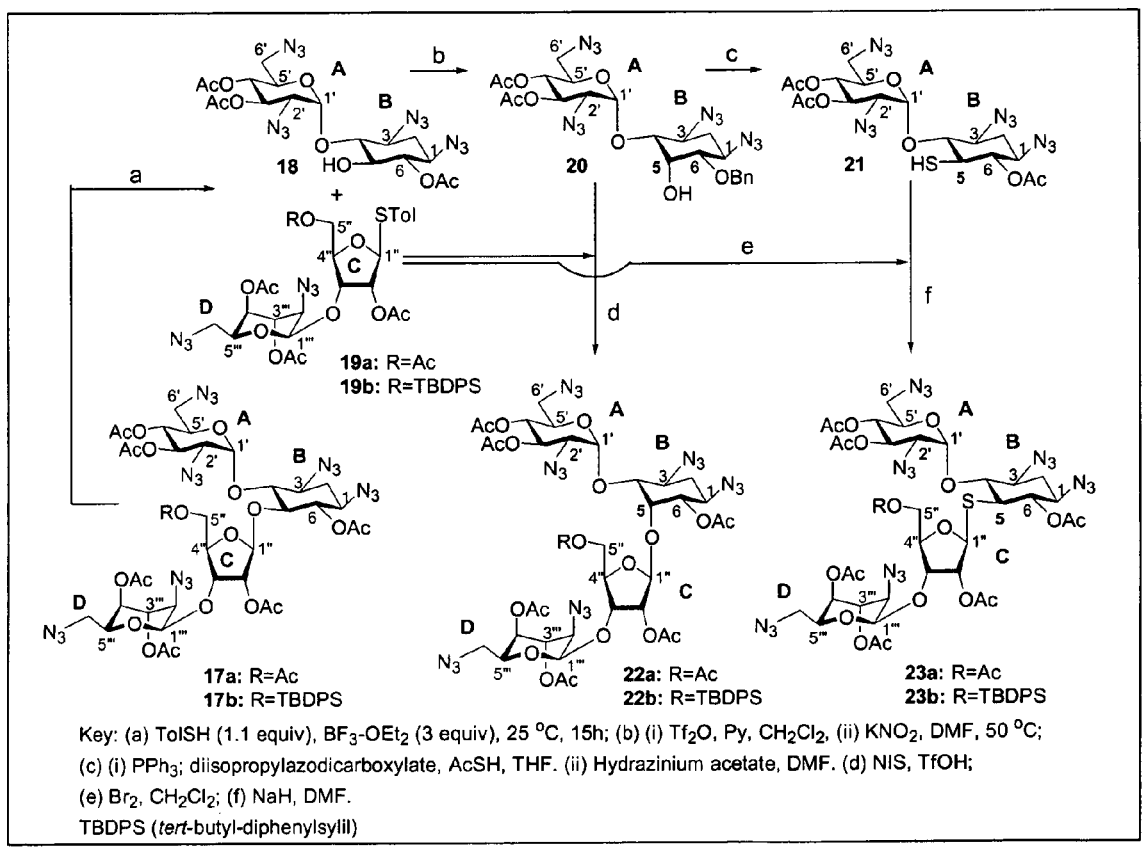
FIG. 13 shows synthesis of another exemplary group of intermediates according to the present invention.

FIG. 13 shows the overall synthetic protocol for the assembly of set4-set5 structures. The protected perazido-neomycin B (compound 17a, FIG. 13) can be sufficiently hydrolyzed in the presence of TolSH and $BF_3$—$OEt_2$ to yield the neamine fragment 18 and the thioglycoside 19a in 90% and 82% yields, respectively (38). Inversion of configuration at C5 of 18 provides the protected epi-neamine 20. While this step can be accomplished in various methods, the approach of Moriarty et al (39), that uses triflation of the alcohol followed by treatment with sodium nitrite, has been proved to be very successful when examined for different oligosaccharides. The 5-epi-neamine derivative 20 can be easily transformed to the corresponding 5-thio-neamine 21 in two simple steps: Conversion of the 5" hydroxyl in to the corresponding S-acetyl by the Mitsunobu procedure, followed by S-deacetylation using hydrazinium acetate in DMF. Treatment of 20 with the thioglycoside 19a will provide the core structure of the protected 5-epi-neomycin B (22a), which after subsequent deprotection steps will afford the epi-neomycin B. Similarly, treatment of the protected 5-thio-neamine 21 with the corresponding bromide of 19a and deprotection steps of the intermediate 23a will afford the 5-thio-neomycin B.

In summary, the synthetic strategy outlined in FIG. 13 involves the conversion of the natural neomycin B to the corresponding 5-epi-neomycin B (22a) and 5-thio-neomycin B (23a) with a maximum efficiency: no loss of neomycin fragments and no addition of extra sugars. This strategy is very advantageous, especially because of the relatively low cost of the commercial neomycin B. In addition, this strategy also provides an efficient method for the preparation of epi-ribostamycin and 5-thio-ribostamycin (FIG. 1). Thus, coupling of 20 with 8a, followed by simple deprotection steps as outlined above will result the 5-epi-ribostamycin. Similarly, coupling of 21 with the corresponding anomeric bromide of 8a after subsequent deprotection will afford a 5-thio-ribostamycin.

Furthermore, by starting this pathway with compound 17b (instead of 17a) it is possible to generate the corresponding 5-epi and 5-thio derivatives of neomycin, 22b and 23b, respectively. Selective deprotection of the silyl group in these compounds will result the corresponding C5"-OH derivatives, 22 (R=H) and 23 (R=H), which will be used as common acceptors for the preparation of set4 and set5 compounds.

Optionally, it is possible to further modify these structures and to thereby generate a library of set4 and set5 compounds. For this purpose optionally and preferably the general strategy outlined in FIG. 8 for the preparation of set1-set3 compounds is followed, but instead of 1-3 as acceptors compounds 22 and 23 are employed.

EXAMPLE 5

Antibiotic Activities of the Compounds According to the Present Invention

The new analogs have been tested for antibacterial activities against both Gram-negative and Gram-positive bacteria including pathogenic and resistant strains by determining minimal inhibitory concentrations (MICs). FIG. 16 shows the structures of neomycin B (Compound I) and Compounds II-XIII according to the present invention, which were tested as described in greater detail below.

In addition to the standard resistant strains, for which their mechanisms of resistance are well known, the activity of these neomycin B derivatives have been studied on multiple antibiotic resistant "natural" strains collected from human and farm origin. One exemplary model is the food-borne pathogen Salmonella, since it is among the leading cause of foodborne disease, foodborne-related hospitalization and foodborne-related deaths. The salmonellae bacteria are responsible for an estimated 16 million annual instances of typhoid fever, primarily in developing countries, and untold millions of cases of gastroenteritis in both industrialized and developing countries. This is a zoonotic pathogen that usually exposed to a variety of antibiotics in the farm, including a wide range of aminoglycosides.

This Example describes experiments which were performed to test the efficacy of the compounds of the present invention against different microorganisms, including strains of those microorganisms which were already shown to be antibiotic resistant.

The compounds were tested for antibacterial activities against both Gram-negative and Gram-positive bacteria, including pathogenic and resistant strains, and the minimal inhibitory concentrations (MIC) were determined using a microdilution assay with neomycin B and kanamycin as controls (see Phillips, I.; Williams, D. In *Laboratory Methods in Antimicrobial Chemotherapy*; Gerrod, L., Ed.; Churchill Livingstone Press: Edinburg 1978; pp 3-30).

Resistant strains included *E. coli* XL1(pET9d), *Pseudomonas aeruginosa* (ATCC 27853), and *Salmonella virchow* (SV49). *E. coli* XL1-(pET9d) is an antibiotic-sensitive laboratory strain of *E. coli* that harbors plasmid pET9d with the cloned orf2 gene, which codes for aminoglycoside kinase APH(3'). *P. aeruginosa* is a Gram-negative pathogen. The aph(3')-IIb gene, which codes for APH(3'), is a chromosomal gene that was found in many clinical isolates of *P. aeruginosa*, including the ATCC 27853 strain, and likely accounts at least partly for the resistance of *Pseudomonas* to aminoglycosides (Hachler, H.; Santanam, P.; Kayser, F. H. *Antimicrob. Agen. Chemother.* 1996, 40, 1254-1256). *S. virchow* (SV49) is a clinical multidrug-resistant strain obtained from poultry and found to be resistant to streptomycin, tetracycline, ampicillin, sulfa, kanamycin, and neomycin. The mechanism(s) of resistance of this strain is still not known.

The results are shown in Table 18 below.

From the MIC values, it turns out that among the four analogs, only Compound V having a ribose substituent at ring E is as potent as neomycin B against *E. coli* strains. The activity of this analogue against *E. coli* XL1(pET9d) having kanamycin resistance is even more impressive, exhibiting better activity than neomycin B. The analogue Compound V is also effective against Gram-positive bacteria, *Staphylococcus epidermidis* and *Bacillus subtilis*. Furthermore, Compound V demonstrates better activity than other analogues against pathogenic bacterium *Salmonella virchow* that is resistant to kanamycin and neomycin B. In this case Compound V is about 5 times more effective than kanamycin and 2 times more effective than neomycin B. The susceptibility of enterobacterium *Pseudomonas aeruginosa* was also examined, which is often very difficult to treat, sometimes requiring use of a combination of aminoglycosides with other antibiotics (Haddad, J.; Kotra, L. P.; Liano-Sotel, B.; Kim, C.; Azucena, E. F., Jr.; Liu, M.; Vakulenko, S. B.; Chow, C. S.;

Mobashery, S. *J. Am. Chem. Soc.* 2002, 124, 3229-3237). Interestingly, in this particular case, while Compound V demonstrates activity close to that of neomycin B, while the 2-glucosamino derivative Compound IV is even more effective than Compound V and the diamino derivative Compound III is superior to both.

As can be seen from these additional results, several of the compounds provide results which are at least as good as kanamycin and/or neomycin B for particular strains, such as certain strains of *E. coli*. Compounds VI-VIII and X provided improved results over kanamycin and similar results to neomycin B for other strains, such as resistant forms of

TABLE 18

MICs of Compound I-V against Various Bacterial Strains

| bacterial strain | MIC (μg/mL) | | | | | |
|---|---|---|---|---|---|---|
| | KAN[a] | I | II | III | IV | V |
| *E. coli* (R47-100) | ND[b] | 4-5.5 | 85 | 40-50 | 35-40 | 4.5-6 |
| *E. coli* (ATCC 25922) | ND | 8-10 | 95 | 40-50 | 25-30 | 10-11 |
| *E. coli* XL1 blue (pET9d) | 260-270 | 50-60 | >200 | >200 | >200 | 35-45 |
| *Staphylococcus epidermidis* (ATCC 12228) | ND | 0.3-0.4 | 5.5-7 | 1.5-1.8 | 1.4-1.8 | 0.2-0.4 |
| *Bacillus subtilis* (ATCC 6633) | ND | 0.8-0.9 | 8.5-10 | 3.5-4 | 1.4-1.8 | 0.6-0.8 |
| *Salmonella virchow* (SV49) | 500-570 | 200-250 | >1250 | >1250 | >1250 | 75-125 |
| *Pseudomonas aeruginosa* (ATCC 27853) | 450-500 | 55-60 | 110-130 | 30-35 | 40-50 | 60-65 |

[a]KAN = kanamycin. [b]ND = not determined.

The observed preliminary data obtained with Compounds II-V indicate that, without wishing to be limited by a single hypothesis, merely increasing the number of amino groups on the natural drug may not lead to an increase in antibacterial activity, even though the binding affinity of these analogues to RNA is likely to increase in vitro. However, the excellent activities observed for the amino derivatives III and IV against *Pseudomonas* but significantly weak activities against other bacterial strains imply that the structural and functional requirements for this family of drugs are not similar in order to reach analogous high antibacterial performance against different organisms, again without wishing to be limited by a single hypothesis.

Additional data has been obtained with other compounds according to the present invention, as shown with regard to Table 19 below. These experiments were performed in a manner similar to those described above.

*Pseudomonas aeruginosa*. Indeed for this strain, Compound VIII provided significantly better results than either kanamycin or neomycin B. Overall good results against different strains were demonstrated for all of the compounds for at least certain strains.

Overall, the neomycin B derivatives prepared in this study represent a new class of branched aminoglycoside antibiotics that show antibacterial activity superior to that of neomycin B and/or kanamycin against pathogenic and resistant bacterial strains, although the breadth of activity across different strains differed between the compounds.

EXAMPLE 6

Treatment of Genetic Disorder with Compounds According to the Present Invention

The previous Example discussed the antibiotic activities of some exemplary compounds of the present invention. How-

TABLE 19

MICs of Compounds VI-XI against various bacterial strains

| Bacterial strain | MIC (μg/mL) | | | | | | | |
|---|---|---|---|---|---|---|---|---|
| | KAN[a] | I | VI | VII | VIII | IX | X | XI |
| *E. coli* (R47-100) | ND[b] | 4-5.5 | 35-50 | 45-50 | 50-70 | 90-100 | 150-200 | 30-40 |
| *E. coli* (ATCC 25922) | ND | 8-10 | 35-40 | 45-60 | 30-50 | 100-150 | 100-150 | 25-40 |
| *E. coli* XL1 blue (pET9d)[c] | 260-270 | 50-60 | 200-250 | 250-400 | 150-200 | 700-800 | 250-500 | >200 |
| *Staphylococcus epidermidis* (ATCC 12228) | ND | 0.3-0.4 | 4-5 | 4.5-5.5 | 5.5-6.0 | 10-11 | 4-5 | 1.5-3 |
| *Bacillus subtilis* (ATCC 6633) | ND | 0.8-0.9 | 5-7 | 6-7 | 5-7 | 10-11 | 5-10 | 1-2.5 |
| *Salmonella virchow* (SV49) | 500-570 | 200-250 | >1000 | >1000 | >1000 | >800 | >1000 | >250 |
| *Pseudomonas aeruginosa* (ATCC 27853) | 400-500 | 55-60 | 55-60 | 45-50 | 10-15 | 350-400 | 40-60 | 200-400 |

[a]KAN, kanamycin; [b]ND, not determined.

ever, these compounds are expected to have other effects as well, some of which are discussed below.

One illustrative use of the compounds of the present invention is for treatment of genetic disorder, such as cystic fibrosis for example. The treatment of cystic fibrosis with the aminoglycosaccharide gentamicin has been shown (Wilschanski et al, "Gentamicin-induced correction of CFTR function in patients with cystic fibrosis and CFTR stop mutations", *New Eng. J. Med.*, vol 349, pp. 1433-41 Oct. 9, 2003; hereby incorporated by reference as if fully set forth herein). It is believed that this effect is obtained by blocking a premature stop codon which leads to a shortened version of CFTR (cystic fibrosis transmembrane conductance regulator); this mutation causes the effects of cystic fibrosis, which cause the lungs of the affected subject to fill with mucous, leading to bacterial infection, severely reduced pulmonary function and often premature death. Blocking the premature stop codon causes "read through", such that a longer protein is transcribed which has at least additional activity compared to the mutated protein. In the previously described reference, treatment with gentamicin was shown to result in full length CFTR in a number of patients.

Without wishing to be limited by a single hypothesis, it is believed that as the compounds of the present invention are also aminoglycoside derivatives, the compounds of the present invention should also be useful for treatment of cystic fibrosis. Such treatment may be effective for a number of reasons, including but not limited to, one or more of reduction or elimination of bacterial infection through the antibiotic effect of the compounds according to the present invention; and/or also blocking the premature stop codon.

Treatment would preferably include administration of a therapeutically effective amount of a compound according to the present invention to a subject. Dosing and administration routes could easily be determined by one of ordinary skill in the art, and would optionally include such routes as oral, topical, nasal, inhaled, optical, parenteral and so forth, as described in greater detail below; however, for cystic fibrosis treatment, optionally and preferably treatment would include administration of the compound according to the present invention directly to the lungs, for example through an inhaled spray or mist, and/or powder inhaler. Preferably, the compound would be provided in a suitable formulation, also as described in greater detail below. The compound may also optionally be combined with other type(s) of treatment for cystic fibrosis, for example by including treatment with one or more other medications that are known in the art.

Non-limiting examples of other genetic disorders for which treatment with a compound according to the present invention may be useful include Duchenne's muscular dystrophy or Hurler's syndrome which are also characterized by truncation mutations.

EXAMPLE 7

Other Activities of the Compounds According to the Present Invention

The previous Example discussed the antibiotic activities and also anti-cystic fibrosis activity of some exemplary compounds of the present invention. However, these compounds are expected to have other effects as well, some which are discussed below.

Aminoglycoside Variants as Potential Ribonucleases

Since aminoglycoside antibiotics exert their antibacterial activity by selectively recognizing and binding to a ribosomal RNA, it is hypothesized that the combination of this already existing recognition element in natural drugs with a catalytic element into a single molecule would significantly increase the activity of the resulted structure. The following observations supported this hypothesis. First, Wong and co-workers demonstrated a nearly linear relationship between the $IC_{50}$ of in vitro translation inhibition and the MIC values for a series of natural aminoglycosides and their synthetic analogs (12e, 14). In general, MIC values were at about 100-fold higher concentrations than the corresponding $IC_{50}$ values.

To explain these differences it was suggested that since the ribosomal RNA is the most dominant RNA in the cell, at low drug concentrations, a tight ribosome-binding drug titrates only a small fraction of the very large number of ribosomes and only at higher concentrations of drug are all ribosomes saturated and protein synthesis impaired. These data imply that an increasing binding affinity of the drug to target RNA should not merely result in better antibiotic function in the sense of required administered dose of the drug, and that most potent ribosome-targeting antibiotics could be envisioned if they were designed to be catalytic inhibitors (12e, 14).

Second, several examples of site-directed RNA cleaving agents that combine a reactive moiety capable of cleaving phosphodiester bond with a recognition element capable of sequence-specifically hybridizing to target RNA, have been reported (41). Third, in analogy to earlier observations in which several simple oligoamines, (42), as well as basic polypeptides (43) have been shown to catalyze RNA hydrolysis, it was likely that aminoglycosides that represent polycationic molecules could exhibit similar effect. Indeed, it has recently been shown that neomycin B, which has three times as many amines as 1,3-propanediame, catalyzes hydrolysis of adenylyl(3'-5')-adenosine (ApA) 3-fold faster than 1,3-propanediamine (44). Neomycin B consists of the meso-1,3-diaminocyclitol (2-deoxystreptamine) ring for which the $pK_a$ values of 5.74 and 8.04 were reported. This may lead to a higher population of a monocationic form at a given pH compared to 1,3-propanediamine, and therefore to a faster hydrolysis.

However, the observed first-order rate constants for neomycin was over 1000-fold lower than those reported for natural ribozymes. It is clear that further increase of the catalytic activity of natural aminoglycosides should be plausible if the molecular design will be more precise. The simplicity and stability of aminoglycosides, in conjunction with the recent progress in 3D structure determination of aminoglycosides bound to rRNA, are undoubtedly advantageous for this purpose.

Design and Synthesis of Neomycin Variants as Potential Ribonucleases.

Based on the results obtained with various oligoamines as a motif for the molecular recognition and hydrolysis of the phosphodiester bond of RNA, briefly introduced in the previous section, two series of neomycin analogs are prepared: (1) structures of set1-set5 that contain 1,2-diamino and 1,3-diamino moieties as "catalytic warheads"; (2) structures of set5 and set6 that represent pseudo-hexasaccharide variants.

(1) Variants with "catalytic warheads." For this purpose the diamine building blocks 5f, 6f, 7a, (FIG. 7) and 24 (FIG. 14) were specially designed. Structures 7a and 24 consist of 1,2-diamino moieties in a cis configuration. Such vic-cis-diamino moieties in 7a and 24 exhibit rigid spatial orientation of two neighboring amino groups and might be more advantageous for catalysis than highly flexible amines in 1,2-ethylenediamine. In addition, N—C—C—N torsion angle in ribofuranoside 24 (eclipsed relationship) is different than that in allopyranoside 7a (gauche relationship). Structures 5f and 6f contain 1,3-diamino moieties and have gluco and galacto configurations, respectively. It is noteworthy that although 1,3-diamino moiety is very common in aminoglycoside antibiotics, this moiety is mostly present in the 2-deoxystreptamine unit (meso-1,3-diamino cyclitol, ring B in neomycin B) and is different from the flexible diamine such as in 5f and 6f. Therefore, investigation of 5f and 6f, along with 7a and 24, is very challenging from both points of view: they represent new "catalytic warheads" for the cleavage of phosphodiester bond, and their incorporation into appropriate oligosaccharides, may result novel antibiotics.

Figure 14:
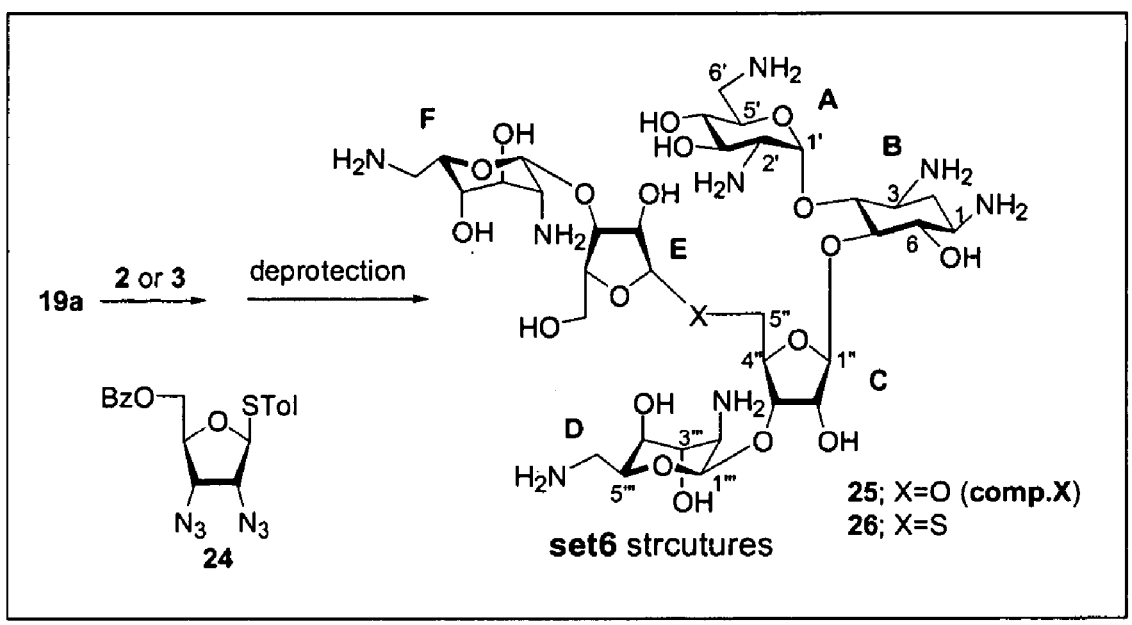
FIG. 14 shows an exemplary synthesis of set6 structures according to an embodiment of the present invention.

A description of this synthetic scheme is described with regard to FIG. 14.

These monosaccharide building blocks can be incorporated into the above designed set1-set5 structures as variable sugar rings to yield corresponding pseudo-pentasaccharides, which will be tested for ribonuclease activity as outlined below.

Figure 15:
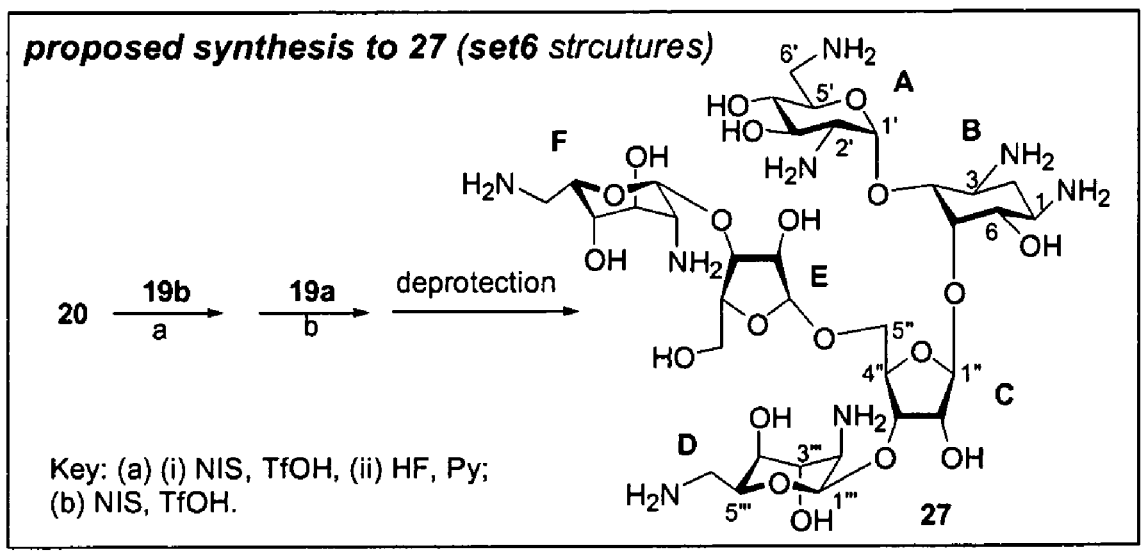
FIG. 15 shows an additional exemplary synthesis of set6 structures according to an embodiment of the present invention.

(2) pseudo-hexasaccharide variants. Electrostatic interactions have been shown to be critically important in RNA binding (45). Increasing the number of positively charged ammonium groups in ligands resulted enhanced binding affinities by RNA host. Since binding affinity of substrate to the catalyst is very important and strongly contributes to the overall efficiency of any catalytic system, it is clear that by increasing the binding affinities of our designed structures to RNA substrate we should subsequently increase their probability as catalysts. Therefore, in attempts to improve the catalytic power of the above designed pseudo-pentasaccharides (set1-set5), a new set, set6, of the pseudo-hexasaccharides are prepared (FIGS. 14 and 15). The two pseudo-hexasaccharides 25 and 26 can be easily assembled by coupling of the disaccharide donor 19a (FIG. 13) with either 1 or 2 as acceptors and subsequent deprotection steps as illustrated in FIG. 14. (Note added: As an illustrative example, compound 25 (which is also the final product Compound X in FIG. 16) has been successfully synthesized and the data of this synthesis and antibacterial tests are summarized in the previous sections.) These two compounds remain the original neomycin structure, so that the likelihood of their binding to the rRNA A-site is very high. The other structure of set 6, compound 27, has the epi-neomycin core, and can be easily assembled from the neomycin fragments discussed above. Thus, coupling of neamine derivative 20 with 19b will afford the corresponding epi-neamine derivative, which after deprotection of the primary alcohol, coupling with 19a, and deprotection steps will furnish the epi-neomycin hexasaccharide derivative 27 (FIG. 15).

EXAMPLE 8

Antibacterial Activity Against *Bacillus Anthracis* and Inhibition of Anthrax Lethal Factor by the Compounds of the Present Invention Example 5 above showed that the compounds according to the present invention can be used for treatment of a subject suffering from infection by an infectious microorganism, including gram-negative and gram-positive bacteria for example.

This Example provides an illustrative, non-limiting example of use of selected compounds according to the present invention against the Gram-positive bacterium, *Bacillus anthracis* for treatment of anthrax, and for inhibition of Anthrax Lethal Factor.

The new derivatives of neomycin B, Compounds II-XIII of FIG. 16, were synthesized according to the general strategy described in Example 1 for compounds of Formula I (FIG. 8), via the corresponding intermediates. The synthetic strategy and preparation of the exemplary intermediates are set forth in Example 1.

Using an in vitro fluorescent assay (22), the novel Compounds II-XIII according to the present invention were examined for the protease activity inhibition of LF, at both high and low salt concentrations.

Low-salt conditions comprised potassium 2-[4-(2-hydroxyethyl)-1-piperazinyl]ethanesulfonic acid (HEPES) buffer at pH 7.4 (10 mM), LF (about 33 nM), varying concentrations (4, 6, 10, and 20 µM) of a fluorescent substrate, and varying concentrations of Compounds II-XIII (the concentrations of Compound XII were 0, 16.2, 32.5, and 54.1 nM; the concentrations of all other compounds were 0, 165, 330, and 550 nM). The $K_i$ values were estimated from double-reciprocal plots of initial velocities as a function of substrate concentration.

High-salt conditions comprised potassium HEPES buffer at pH 7.4 (10 mM), KCl (150 mM), LF (about 33 nM), varying concentrations (10, 20, 40, and 100 µM) of a fluorescent substrate, and varying concentrations of Compounds II-XIII (as described above for the low-salt conditions). The $K_i$ values were estimated as in the low-salt conditions. Each experiment was performed also in the presence of 0.1 mg/mL BSA (data presented in parantheses). All assays were performed in triplicate and analogous results were obtained in at least two or three experiments.

TABLE 20

Apparent inhibition constants ($K_i$) of the commercial neomycin B (I) and its synthetic derivatives II-XIII for the protease activity of LF at various assay conditions.

| Aminoglycosides | $K_i$ (nM) Low salt | $K_i$ (µM) High salt |
| --- | --- | --- |
| Neomycin B (I) | 37 ± 2 (34 ± 0.4) | 59 ± 6 (64 ± 8) |
| II | 11 ± 2 | 50 ± 7 |
| III | 0.5 ± 0.1 (17 ± 4) | 28 ± 6 (30 ± 5) |
| IV | 13 ± 2 | 66 ± 9 |
| V | 28 ± 2 | 134 ± 17 |
| VI | 1.3 ± 0.4 | 39 ± 6 |
| VII | 15 ± 2 (36 ± 5) | 85 ± 11 (58 ± 8) |
| VIII | 0.6 ± 0.1 (15 ± 3) | 20 ± 3 (24 ± 3) |
| IX | 0.2 ± 0.1 | 10 ± 2 |
| X | 0.4 ± 0.1 | 21 ± 4 |
| XI | 52 ± 5 | 81 ± 21 |
| XII | 23 ± 2 | 125 ± 25 |
| XIII | 0.7 ± 0.2 (33 ± 6) | 1.1 ± 0.2 (1.2 ± 0.2) |

As is shown in Table 20, all the tested compounds were found to be competitive inhibitors. From the measured apparent $K_i$ values at low ionic strength assay conditions (low salt), it was found that among the analogues tested, 6 compounds (III, VI, VIII, IX, X, XIII), having $K_i$ values in the range of 0.2-1.3 nM, are predominantly better inhibitors than the neomycin B itself ($K_i$=37 mM). It was further found that the binding affinity of the analogues of gluco series (having a glucose substituent at ring V) increases gradually with increasing number of amino groups on the ring: (2NH$_2$)glucose (II, VIII)>(1NH$_2$)glucose (III, VIII)>glucose (IV, VII). In this series of compounds, no particular influence on the position of the amino group(s) on the glucose ring is observed. The ring configuration, however, has a more significant effect: the ribosamino derivative VI binds about 10-fold tighter than two monoamino derivatives of glucose (IV and VII), and the diamino-D-allose derivative 1, which consists of an unusual cis-1,2-diamine substitution at ring E, binds about 20-fold weaker than the amino-D-glucose derivatives III and VIII. These data suggest that, although the number of amino groups on the ligand is in general critical for LF binding affinity, structural features of the ligand play an important role in the proper recognition of LF.

Without wishing to be bound to a particular theory, it was hypothesized that since the disulfide dimer XIII has twice as many amino groups as its parent "monomeric" IX, its binding affinity to LF would be expected to be significantly higher. The observed similar extent of inhibition of XIII and IX was, however, very intriguing suggesting that in the case of the dimer XIII, in addition to a "specific" active site binding, an additional "nonspecific interaction" with the LF protein may occur.

Various studies dealing with many different protein-polyelectrolyte interactions (31) and the interactions of aminoglycosides with a number of ribozymes (12, 21), support this assumption. To test this possibility, the Compounds IX and XIII, along with neomycin B, were evaluated in the presence of 0.1 mg/mL of BSA. Again without wishing to be bound by theory, it was found that while the binding affinities of both neomycin B and Compound IX were not significantly affected, the binding of Compound XIII was reduced 47-fold by the addition of BSA, implying a nonspecific protein-ligand association in the case of Compound XIII which increases with increased protein concentration.

Although, to date, no direct structural data on the interaction of aminoglycosides with LF is available, and without wishing to be bound by theory, a preliminary investigation of the binding mechanism suggests that the inhibitory activity of aminoglycosides is ionic strength dependent, supporting the possibility that the predominant interaction between the LF and aminoglycosides may be electrostatic in origin (35). Increasing the ionic strength from 0 to 150 mM KCl drastically shifts the $K_i$ values of all aminoglycosides towards higher concentrations by factors of about 1500-53,000 (Table 20). These data suggest that the compounds of the present invention, including the parent neomycin B, can be replaced from their LF binding site even at a relatively low ionic strength. A possible reason for the observed different sensitivities of different aminoglycosides to changes in ionic strength may be their different numbers of amino groups and their individual pKa values. In addition, it is likely that the pKa values of individual ammonium groups of neomycin B and of the dimer XIII are the same, resulting in XIII behaving like a "monomer" and displaying the same sensitivity as neomycin B towards ionic strength (about 1500-fold, Table 20) (38).

Without wishing to be bound by theory, the observed 53-fold higher affinity of Compound XIII compared to that of the neomycin B, both at the low and high salt concentrations, suggests that the presence of twice the number of charged groups in XIII may be responsible for its increased affinity. Such high ionic strength conditions may also be able to overcome the nonspecific LF-XIII association, as suggested by the same $K_i$ value observed for XI, with and without the presence of BSA. Furthermore, since 150 mM KCl best resembles the physiological ionic strength into the mammalian cell (39), XIII can be considered as a preferred aminoglycoside inhibitor of LF at seemingly physiological conditions.

When the new derivatives II-XIII were tested by means of surface plasmon resonance (SPR) against immobilized 27-mer RNA construct (AS-wt) (25), binding constants in the range of 0.4-2.9 µM were determined, with no obvious dependence of $K_d$ on modification type (Table 21). Several of these derivatives, including the dimer XIII ($K_d$=0.4 µM), displayed apparently similar extent of binding affinity to that of the parent neomycin B ($K_j$=0.3 µM), showing no apparently significant contribution of the number of amino groups on the ligand to RNA binding; Without wishing to be bound by theory, it is suggested that, unlike the binding affinity to LF, in which increasing number of amino groups on the natural drug lead to increased binding, a more subtle balance of interactions may govern the binding affinity of these ligands to RNA.

To compare the observed RNA binding affinities to antibacterial activity, the Compounds II-XIII were further investigated against B. anthracis (Sterne strain) (40), and the minimal inhibitory concentrations (MIC) were determined using a microdilution assay with neomycin B as a control (Table 21). No previous studies on aminoglycoside drugs have been performed to make such a comparison between rRNA binding and antibacterial activity for B. anthracis.

Minimal inhibitory concentrations (MIC) against B. anthracis and binding constants ($K_d$) to 16S A site RNA were tested for the commercial neomycin B and its synthetic derivatives II-XIII. For the MIC measurements, the concentrated stock solutions of aminoglycosides were prepared in distilled water with known concentration. Two-fold dilutions were used in a concentration range from 0.015 to 1024 mg/L diluted in 100 µL of BHI broth and poured into wells of microtitre plates (Nunc 96-well flat-bottomed microtitre plates; Nunc, Roskilde, Denmark). A 10 µL volume of culture containing $10^5$ cfu/mL of B. anthracis Sterne strain was then added. Following incubation of the plates for 18 h at 37° C. in ambient air, the MICs were determined as the lowest concentration of an antibacterial agent that completely inhibited visible growth of the bacteria.

The sequence of 27-mer 16S A site RNA construct used in this study was 5' BiGGCGUCACACCU-UCGGGUGAAGUCGCC 3', and the binding assays were performed as previously described (11).

From the MIC values, it appears that all of the synthetic derivatives possess significant antibacterial activity against B. anthracis, some of them displaying activity levels comparable to that of neomycin B. In spite of the similar binding affinities of the neomycin B and the dimer XIII to 16S A site RNA, their antimicrobial activities differed by a factor of eight, suggesting that no direct correlation between rRNA binding and antibacterial activity can be made. While this is in agreement with earlier reported data on other aminoglycoside analogues (41), further structure-activity studies within more diverse structures of neomycin B analogues are clearly required to better understand this issue in detail.

TABLE 21

Minimal inhibitory concentrations (MIC) against B. anthracis and binding constants ($K_d$) to 16S A site RNA for the commercial neomycin B and its synthetic derivatives II-XIII.

| Aminoglycosides | MIC (µg mL$^{-1}$) | $K_d$ (µM) |
|---|---|---|
| Neomycin B (I) | 0.25 | 0.3 ± 0.1 |
| II | 8 | 2.0 ± 0.2 |
| III | 2 | 1.3 ± 0.3 |
| IV | 2 | 0.9 ± 0.1 |
| V | 1 | 0.7 ± 0.1 |
| VI | 2 | 0.7 ± 0.1 |
| VII | 2 | 0.7 ± 0.1 |
| VIII | 1 | 0.6 ± 0.1 |
| IX | 8 | 2.9 ± 0.6 |
| X | 2 | 1.9 ± 0.3 |
| XI | 2 | 1.0 ± 0.2 |
| XII | 8 | 1.1 ± 0.2 |
| XIII | 2 | 0.4 ± 0.1 |

EXAMPLE 9

Treatment with Compounds According to the Present Invention

The above results show that the compounds according to the present invention can be used for treatment of a subject suffering from infection by an infectious microorganism. Optionally, the compounds of the present invention can be used to treat a subject suffering from a genetic disorder, including but not limited to, cystic fibrosis, Duchenne's muscular dystrophy, or Hurler's syndrome for example. Alternatively, the compounds of the present invention can be used to treat a subject suffering from anthrax. The method preferably includes administering the compound of the present invention to the subject through a suitable route of administration.

The compounds of the present invention are potentially useful for the treatment of a wide spectrum of different types and/or species of bacteria, such as gram negative and gram-positive bacteria for example.

The organisms potentially amenable to therapy with one or more of the compounds according to the present invention include a wide variety of Gram-positive and Gram-negative organisms with a variety of growth circumstances and requirements ranging from aerobic to anaerobic growth, including but not limited to:

(a) Gram-positive bacteria, including but not limited to, *Strep. pyogenes* (Group A), *Strep. pneumoniae, Strep.* GpB, *Strep. viridans, Strep.* GpD-(Enterococcus), *Strep.* GpC and GpG, *Staph. aureus, Staph. epidermidis, Bacillus subtilis, Bacillus anthracis, Listeria monocytogenes,* Anaerobic cocci, *Clostridium* spp., and *Actinomyces* spp; and (b) Gram-negative bacteria, including but not limited to, *Escherichia coli, Enterobacter aerogenes, Kiebsiella pneumoniae, Proteus mirabilis, Proteus vulgaris, Morganella morganii, Providencia stuartii, Serratia marcescens, Citrobacter freundii, Salmonella typhi, Salmonella paratyphi, Salmonella typhi murium, Salmonella virchow, Shigella* spp., *Yersinia enterocolitica, Acinetobacter calcoaceticus, Flavobacterium* spp., *Haemophilus influenzae, Pseudomonas aeruginosa, Campylobacter jejuni, Vibrio parahaemolyticus, Brucella* spp., *Neisseria meningitidis, Neisseria gonorrhoea, Bacteroides fragilis,* and *Fusobacterium* spp.;

(c) optionally including other organisms such as a Mycobacteria strain, including but not limited to, *Mycobacterium tuberculosis, Mycobaterium smegmatis* and other Mycobacteria.

It should be noted that the term "treatment" also includes amelioration or alleviation of a pathological condition and/or one or more symptoms thereof, curing such a condition, or preventing the genesis of such a condition.

The compounds of the present invention can be used to produce a pharmaceutical composition. Thus, according to another aspect of the present invention there is provided a pharmaceutical composition which includes, as an active ingredient thereof, a compound and a pharmaceutical acceptable carrier. As used herein a "pharmaceutical composition" refers to a preparation of one or more of the active ingredients described herein, either compounds or physiologically acceptable salts thereof, with other chemical components such as traditional drugs, physiologically suitable carriers and excipients. The purpose of a pharmaceutical composition is to facilitate administration of a compound or cell to an organism. Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

In a preferred embodiment, the term "pharmaceutically acceptable" means approved by a regulatory agency of the Federal or a state government or listed in the U.S. Pharmacopeia or other generally recognized pharmacopeia for use in animals, and more particularly in humans. Hereinafter, the phrases "physiologically suitable carrier" and "pharmaceutically acceptable carrier" are interchangeably used and refer to an approved carrier or a diluent that does not cause significant irritation to an organism and does not abrogate the biological activity and properties of the administered conjugate.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should be suitable for the mode of administration.

Herein the term "excipient" refers to an inert substance added to a pharmaceutical composition to further facilitate processes and administration of the active ingredients. Examples, without limitation, of excipients include calcium carbonate, calcium phosphate, various sugars and types of starch, cellulose derivatives, gelatin, vegetable oils and polyethylene glycols.

Further techniques for formulation and administration of active ingredients may be found in "Remington's Pharmaceutical Sciences," Mack Publishing Co., Easton, Pa., latest edition, which is incorporated herein by reference as if fully set forth herein.

The pharmaceutical compositions herein described may also comprise suitable solid or gel phase carriers or excipients. Examples of such carriers or excipients include, but are not limited to, calcium carbonate, calcium phosphate, various sugars, starches, cellulose derivatives, gelatin and polymers such as polyethylene glycols.

Suitable routes of administration may, for example, include oral, rectal, transmucosal, transdermal, intestinal or parenteral delivery, including intramuscular, subcutaneous and intramedullary injections as well as intrathecal, direct intraventricular, intravenous, intraperitoneal, intranasal, or intraocular injections.

Pharmaceutical compositions for use in accordance with the present invention thus may be formulated in conventional manner using one or more pharmaceutically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological saline buffer. For transmucosal administration, penetrants are used in the formulation. Such penetrants are generally known in the art.

For oral administration, the active ingredients can be formulated readily by combining the active ingredients with pharmaceutically acceptable carriers well known in the art. Such carriers enable the active ingredients of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the active ingredient and a suitable powder base such as lactose or starch.

The active ingredients described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

In a preferred embodiment, the composition is formulated in accordance with routine procedures as a pharmaceutical composition adapted for intravenous administration to human beings. Typically, pharmaceutical compositions for intravenous administration are solutions in sterile isotonic aqueous buffer. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The active ingredients of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

The topical route is optionally performed, and is assisted by a topical carrier. The topical carrier is one which is generally suited for topical active ingredient administration and includes any such materials known in the art. The topical carrier is selected so as to provide the composition in the desired form, e.g., as a liquid or non-liquid carrier, lotion, cream, paste, gel, powder, ointment, solvent, liquid diluent, drops and the like, and may be comprised of a material of either naturally occurring or synthetic origin. It is essential, clearly, that the selected carrier does not adversely affect the active agent or other components of the topical formulation, and which is stable with respect to all components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like. Preferred formulations herein are colorless, odorless ointments, liquids, lotions, creams and gels.

Ointments are semisolid preparations, which are typically based on petrolatum or other petroleum derivatives. The specific ointment base to be used, as will be appreciated by those skilled in the art, is one that will provide for optimum active ingredients delivery, and, preferably, will provide for other desired characteristics as well, e.g., emolliency or the like. As with other carriers or vehicles, an ointment base should be inert, stable, nonirritating and nonsensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, reference may be made to Remington: The Science and Practice of Pharmacy for further information.

Lotions are preparations to be applied to the skin surface without friction, and are typically liquid or semiliquid preparations, in which solid particles, including the active agent, are present in a water or alcohol base. Lotions are usually suspensions of solids, and may comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as active ingredients useful for localizing and holding the active agent in contact with the skin, e.g., methylcellulose, sodium carboxymethylcellulose, or the like.

Creams containing the selected active ingredients are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington, supra, is generally a nonionic, anionic, cationic or amphoteric surfactant.

Gel formulations are preferred for application to the scalp. As will be appreciated by those working in the field of topical active ingredients formulation, gels are semisolid, suspension-type systems. Single-phase gels contain organic macromolecules distributed substantially uniformly throughout the carrier liquid, which is typically aqueous, but also, preferably, contain an alcohol and, optionally, an oil.

Various additives, known to those skilled in the art, may be included in the topical formulations of the invention. For example, solvents may be used to solubilize certain active ingredients substances. Other optional additives include skin permeation enhancers, opacifiers, anti-oxidants, gelling agents, thickening agents, stabilizers, and the like.

The topical compositions of the present invention may also be delivered to the skin using conventional dermal-type patches or articles, wherein the active ingredients composition is contained within a laminated structure, that serves as a drug delivery device to be affixed to the skin. In such a structure, the active ingredients composition is contained in a layer, or "reservoir", underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during active ingredients delivery. Examples of suitable skin contact adhesive materials include, but are not limited to, polyethylenes, polysiloxanes, polyisobutylenes, polyacrylates, polyurethanes, and the like. The particular polymeric adhesive selected will depend on the particular active ingredients, vehicle, etc., i.e., the adhesive must be compatible with all components of the active ingredients-containing composition. Alternatively, the active ingredients-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active ingredients and to any other components of the active ingredients-containing composition, thus preventing loss of any components through the upper surface of the device. The backing layer may be either occlusive or non-occlusive, depending on whether it is desired that the skin become hydrated during active ingredients delivery. The backing is preferably made of a sheet or film of a preferably flexible elastomeric material. Examples of polymers that are suitable for the backing layer include polyethylene, polypropylene, and polyesters.

During storage and prior to use, the laminated structure includes a release liner. Immediately prior to use, this layer is removed from the device to expose the basal surface thereof, either the active ingredients reservoir or a separate contact adhesive layer, so that the system may be affixed to the skin. The release liner should be made from an active ingredients/vehicle impermeable material.

Such devices may be fabricated using conventional techniques, known in the art, for example by casting a fluid admixture of adhesive, active ingredients and vehicle onto the backing layer, followed by lamination of the release liner. Similarly, the adhesive mixture may be cast onto the release liner, followed by lamination of the backing layer. Alternatively, the active ingredients reservoir may be prepared in the absence of active ingredients or excipient, and then loaded by "soaking" in an active ingredients/vehicle mixture.

As with the topical formulations of the invention, the active ingredients composition contained within the active ingredients reservoirs of these laminated system may contain a number of components. In some cases, the active ingredients may be delivered "neat," i.e., in the absence of additional liquid. In most cases, however, the active ingredients will be dissolved, dispersed or suspended in a suitable pharmaceutically acceptable vehicle, typically a solvent or gel. Other components, which may be present, include preservatives, stabilizers, surfactants, and the like.

Pharmaceutical compositions suitable for use in context of the present invention include compositions wherein the active ingredients are contained in an amount effective to achieve the intended purpose. More specifically, a therapeutically effective amount means an amount of active ingredient effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any active ingredient used in the methods of the invention, the therapeutically effective amount or dose can be estimated initially from activity assays in animals. For example, a dose can be formulated in animal models to achieve a circulating concentration range that includes the $IC_{50}$ as determined by activity assays.

Toxicity and therapeutic efficacy of the active ingredients described herein can be determined by standard pharmaceutical procedures in experimental animals, e.g., by determining the $IC_{50}$ and the $LD_{50}$ (lethal dose causing death in 50% of the tested animals) for a subject active ingredient. The data obtained from these activity assays and animal studies can be used in formulating a range of dosage for use in human. For example, therapeutically effective doses suitable for treatment of genetic disorders can be determined from the experiments with animal models of these diseases.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma levels of the active moiety which are sufficient to maintain the modulating effects, termed the minimal effective concentration (MEC). The MEC will vary for each preparation, but may optionally be estimated from whole animal data.

Dosage intervals can also be determined using the MEC value. Preparations may optionally be administered using a regimen, which maintains plasma levels above the MEC for 10-90% of the time, preferable between 30-90% and most preferably 50-90%.

Depending on the severity and responsiveness of the condition to be treated, dosing can also be a single administration of a slow release composition described hereinabove, with course of treatment lasting from several days to several weeks or until cure is effected or diminution of the disease state is achieved.

Suppositories generally contain active ingredient in the range of from about 0.5% to about 10% by weight; oral formulations preferably contain from about 10% to about 95% active ingredient.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising an active ingredient of the invention formulated in a compatible pharmaceutical carrier may also be prepared, placed in an appropriate container, and labeled for treatment of an indicated condition.

As used herein, the term "modulate" includes substantially inhibiting, slowing or reversing the progression of a disease, substantially ameliorating clinical symptoms of a disease or condition, or substantially preventing the appearance of clinical symptoms of a disease or condition. A "modulator" therefore includes an agent which may modulate a disease or condition. Modulation of viral, protozoa and bacterial infections includes any effect which substantially interrupts, prevents or reduces any viral, bacterial or protozoa activity and/or stage of the virus, bacterium or protozoon life cycle, or which reduces or prevents infection by the virus, bacterium or protozoon in a subject, such as a human or lower animal.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent and patent application was specifically and individually indicated to be incorporated herein by reference. In addition, citation or identification of any reference in this application shall not be construed as an admission that such reference is available as prior art to the present invention.

REFERENCES CITED BY NUMERALS

Other References are Cited within the Text

1. Cooper, H. L. *Science* 1994, 265, 590.
2. Gross, L. J. *Science* 1994, 265, 590-1.
3. Page, M. G. *Science* 1994, 265, 589-90.
4. Kotra, L. P.; Haddad, J.; Mobashery, S. *Antimicrob. Agents Chemother.* 2000, 44, 3249-3256.
5. Davis, B. D. *Microbiol. Rev.* 1987, 51, 341-350.
6. Umezawa, H., Hooper, I. R., Eds. *Aminoglycoside Antibiotics*; Springer-Verlag: New York, Heidelberg, 1982.
7. Moazed, D.; Noller, H. F. *Nature* 1987, 327, 389-394.
8. Woodcock, J.; Moazed, D.; Cannon, M.; Davies, J.; Noller, H. F. *EMBO J.* 1991, 10, 3099-3103.
9. Wright, G. D.; Berghuis, A. M.; Mobashery, S. *Adv. Exp. Med. Biol.* 1998, 456, 27-69.
10. Fong, D. H.; Berghuis, A. M. *EMBO J.* 2002, 21, 2323-2331.
11. For the recent review see: Ye, X.-S.; Zhang, L.-H. *Curr. Med. Chem.* 2002, 9, 929-939.
12. For representative studies see: (a) Kumar, V.; Jones, G. S. Jr.; Blacksberg, I.; Remers, W. A. *J. Med. Chem.* 1980, 23, 42-49. (b) Yoshikawa, M.; Ikeda, Y.; Takenaka, K. *Chem. Lett.* 1984, 2097-2100. (c) Girodeau, J.-M.; Pineau, R.; Masson, M.; Le Goffic, F. *J. Antibiot.* 1984, 37, 150-158. (d) Alper, P. B.; Hendrix, M.; Sears, P.; Wong, C.-H. *J. Am. Chem. Soc.* 1998, 120, 1965-1978. (e) Greenberg, W. A.; Priestley, E. S.; Sears, P. S.; Alper, P. B.; Rosenbohm, C.; Hendrix, M.; Hung, S.-C.; Wong, C.-H. *J. Am. Chem. Soc.* 1999, 121, 6527-6541. (f) Wang, J.; Li, J.; Tuttle, D.; Takemoto, J. Y.; Chang, C.-W. T. *Org. Lett.* 2002, 3997-4000. (g) Hanessian, S.; Tremblay, M.; Swayze, E. *Tetrahedron* 2003, 59, 983-993.

13. Haddad, J.; Kotra, L. P.; Liano-Sotel, B.; Kim, C.; Azucena, E. F., Jr.; Liu, M.; Vakulenko, S. B.; Chow, C. S.; Mobashery, S. *J. Am. Chem. Soc.* 2002, 124, 3229-3237.

14. Sucheck, S. J.; Wong, A. L.; Koeller, K. M.; Boehr, D. D.; Draker, K.-a.; Sears, P.; Wright, G. D.; Wong, C.-H. *J. Am. Chem. Soc.* 2000, 122, 523-524.

15. Dixon, T. C.; Meselson, M.; Guillemin, J.; Hanna, P. C. *N. Engl. J. Med.* 1999, 341, 815.

16. Duesbery, N. S.; Vande Woude, G. F. *Cell Mol. Life Sci.* 1999, 55, 1599.

17. Montecucco, C.; Tonello, F.; Zanotti, G. *Trends Biochem. Sci.* 2004, 29, 282.

18. Ascenzi, P.; Visca, P.; Ippolito, G.; Spallarossa, A.; Bolognesi, M.; Montecucco, C. *FEBS Lett.* 2002, 531, 384.

19. Duesbery, N. S.; Webb, C. P.; Leppla, S. H.; Gordon, V. M.; Klimpel, K. R.; Copeland, T. D.; Ahn, N. G.; Oskarsson, M. K.; Fukasawa, K.; Paull, K. D.; Vande Woude, G. F. *Science* 1998, 280, 734; Vitale, G.; Bernardi, L.; Napolitani, G.; Mock, M.; Montecucco, C.; *Biochem. J.* 2000, 352 Pt 3, 739; H. Enslen, R. J. Davis, *Biol. Cell* 2001, 93, 5.

20. Maly, D. J.; Choong, I. C.; Ellman, J. A. *Proc. Natl. Acad. Sci. U.S.A.* 2000, 97, 2419; Bunyapaiboonsri, T.; Ramstrom, O.; Lohmann, S.; Lehn, J. M.; Peng, L.; Goeldner, M. *Chem Biochem.* 2001, 2, 438.

21. Tonello, F.; Seveso, M.; Marin, O.; Mock, M.; Montecucco, C. *Nature* 2002, 418, 386; Panchal, R. G.; Hermone, A. R.; Nguyen, T. L.; Wong, T. Y.; Schwarzenbacher, R.; Schmidt, J.; Lane, D.; McGrath, C.; Turk, B. E.; Burnett, J.; Aman, M. J.; Little, S.; Sausville, E. A.; Zaharevitz, D. W.; Cantley, L. C.; Liddington, R. C; Gussio, R.; Bavari, S. *Nat. Struct. Mol. Biol.* 2004, 11, 67; Dell'Aica, I.;. Dona, M.; Tonello, F.; Piris, A.; Mock, M.; Montecucco, C.; Garbisa, S. *EMBO Rep.* 2004, 5, 418.

22. Turk, B. E.; Wong, T. Y.; Schwarzenbacher, R.; Jarrell, E. T.; Leppla, S. H.; Collier, R. J.; Liddington, R. C.; Cantley, L. C. *Nat. Struct. Mol. Biol.* 2004, 11, 60.

23. (a) Umezawa, H.; Umezawa, S.; Tsuchiya, T.; Okazaki, Y. *J. Antibiot.* 1971, 24, 485-487. (b) Kawaguchi, H; Naito, T.; Nakagawa, S.; Fujisawa, K. *J. Antibiot.* 1972, 25, 695-708.24. Kondo, S.; Hotta, K. *J. Infect. Chemother.* 1999, 5, 1-9.

25. Carter, A. P.; Clemons, W. M.; Brodersen, D. E.; Morgan-Warren, R. J.; Wimberly, B. T.; Ramakrishnan, V. *Nature*, 2000, 407, 340-348.

26. Michael, K.; Wang, H.; Tor, Y. *Bioorg. Med. Chem.* 1999, 7, 1361-1371.

27. Sucheck, S. J.; Wong, A. L.; Koeller, K. M.; Boehr, D. D.; Draker, K.-a.; Sears, P.; Wright, G. D.; Wong, C.-H. *J. Am. Chem. Soc.* 2000, 122, 523-524.

28. Wang, H.; Tor, Y. *Angew. Chem., Int. Ed.* 1998, 32, 109-111.

29. For the interaction of unstructured diamines with RNA see: (a) Yoshinari, K.; Yamazaki, K.; Komiyama, M. *J. Am. Chem. Soc.*, 1991, 113, 5899. (b) Komiyama, M.; Yoshinari, K. *J. Org. Chem.*, 1997, 62, 2155-2160. (c) See also Kirk, S. R.; Tor, Y. *Chem. Commun.* 1998, 147-148.

30. For the favorable interaction of the β-hydroxyamine moiety in sugars with the phosphodiester group and the Hoogsteen face of guanine residues in RNA see: Hendrix, M.; Alper, P. B.; Priestley, E. S.; Wong, C.-H. *Angew. Chem., Int. Ed. Engl.* 1997, 36, 95-98.

31. For the interaction of ribofuranoses see: (a) Han, M. J.; Yoo, K. S.; Cho, T. J.; Chang, J. Y.; Cha, Y. J.; Nam, S. H. *Chem. Commun.* 1997, 163-164. (b) Han, M. J.; Yoo, K. S.; Kim, K. H.; Lee, G. H.; Chang, J. Y. *Macromolecules* 1997, 30, 5408-5415. (c) Han, M. J.; Yoo, K. S.; Kim, Y. H.; Chang, J. Y. *Tet. Lett.* 2002, 43, 5597-5600.

32. Kohen, A.; Jakob, A.; Baasov, T. *Eur. J. Biochem.* 1992, 208, 443-449.

33. Solomon, D.; Fridman, M.; Zhang, J.; Baasov, T. *Org. Lett.* 2001, 3, 4311-4314.

34. Fridman, M.; Solomon, D.; Yogev, S.; Baasov, T. *Org. Lett.* 2002, 4, 281-283.

35. Mingeot-Leclercq, M-P.; Glupczynski, Y.; Tulkens, P. M. *Antimicrob. Agents Chemother.* 1999, 43, 727-737.

36. Forge, A.; Schacht, J. *Audiol. Neuro-Otiol.* 2000, 5, 3-22.

37. Arya, D. P.; Micovoc, L.; Charles, I.; Lane Coffee, R L.; Willis, Jr. B.; Xue, L. *J. Am. Chem. Soc.* 2003, 125, 3733-3744.

38. Wu, B.; Yang, J.; He, Y.; Swayze, E. E. *Org. Lett.* 2002, 4, 3455-3458.

39. Moriarty, R. M.; Zhuang, H.; Penamasta, R.; Liu, K.; Awasthi, A. K.; Tuladhar, S. M.; Rao, M. S. C.; Singf, V. K. *Tetrahedron Lett.* 1993, 34, 8029-8032.

40. Bandgar, B. P.; Sadavarte, V. S.; Upalla, L. S. *Chem. Lett.* 2000, 1304.

41. (a) Komiyama, M.; Inokawa, T. *J. Biochem.* 1994, 116, 719-720; (b) Shinozuka, K.; Shimizu, K.; Nakashima, Y *Bioorg. Med. Chem. Lett.* 1994, 4, 1979-1982.

42. (a) Yoshinari, K.; Komiyama, M. *Chem. Lett.* 1990, 519-522; (b) Komiyama, M.; Yoshinari, K. *J. Org. Chem.* 1997, 62, 2155-2160.

43. Oivanen, M.; Kuusela, S.; Lönnberg, H. *Chem. Rev.* 1998, 98, 961-990.

44. Kirk, S. R.; Tor, Y. *Chem. Commun.* 1998, 147-148.

45. Wang, H.; Tor, Y. *J. Am. Chem. Soc.* 1997, 119, 8734-8735.

46. Breslow, R.; Chapman, W. H. Jr. *Proc. Nat. Acad. Sci.* 1996, 93, 10018-10021.

47. Burk, D. L.; Hon, W. C.; Leung, A. K.-W.; Berghuis, A. M. *Biochemistry* 2001, 40, 8756-8764.

48. Hon, W. C.; McKay, G. A.; Thompson, P. R.; Sweet, R. M.; Yang, D. S.; Wright, G. D.; Berghuis, A. M. *Cell* 1997, 89, 887-895.

49. Fridman, M.; Belakhov, V.; Yaron, S.; Baasov, T. *Org. Lett.* 2003, 5, 3575-3578.

50. Dixon, M., Meselson, J., Guillemin, P. C., Hanna C. *N. Engl. J. Med.* 1999, 341, 815.

What is claimed is:

1. A compound having the general formula I:

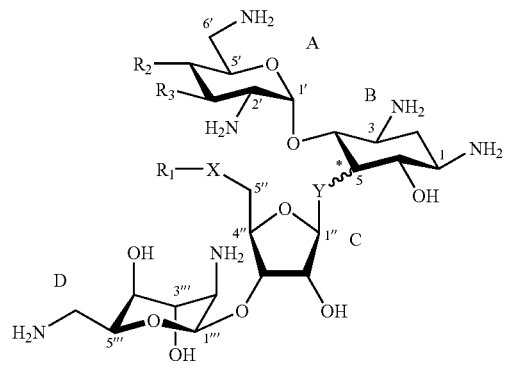

Formula I wherein:
R₁ is a monosaccharide residue or an oligosaccharide residue;
X and Y are each independently oxygen or sulfur;
R₂ and R₃ are each independently selected from the group consisting of hydrogen, hydroxy, thiol, amine, alkyl, cycloalkyl, aryl, alkoxy, aryloxy, thioalkoxy and thioaryloxy; and
wherein the carbon at the fifth position of ring B has an R configuration or an S configuration;
or a pharmaceutically acceptable salt thereof.

2. The compound of claim 1, wherein X is oxygen.
3. The compound of claim 2, wherein Y is oxygen.
4. The compound of claim 3, wherein R₁ is a monosaccharide residue.
5. The compound of claim 4, wherein said monosaccharide residue is a five-membered (furanose) or a six-membered (pyranose) monosaccharide residue.
6. The compound of claim 4, wherein said monosaccharide residue comprises at least one amine group and/or at least one aminoalkyl group.
7. The compound of claim 6, wherein said at least one amine group and/or said at least one aminoalkyl group is at one or more of positions 2, 3, 4 or 5.
8. The compound of claim 7, wherein said at least one aminoalkyl group is an aminomethyl group ($CH_2$—$NH_2$).
9. The compound of claim 8, wherein said monosaccharide residue is a pyranose monosaccharide residue, and said aminomethyl group is at position 5.
10. The compound of claim 7, wherein said monosaccharide residue is a pyranose monosaccharide residue, and said at least one amine group is at one or more of positions 2, 3 or 4.
11. The compound of claim 7, wherein said monosaccharide residue is a furanose monosaccharide residue, and said aminoalkyl group is at position 4.
12. The compound of claim 4, wherein said monosaccharide residue is a L-monosaccharide or a D-monosaccharide.
13. The compound of claim 1, wherein R₁ is an oligosaccharide residue.
14. The compound of claim 13, wherein said oligosaccharide residue comprises at least two monosaccharide residues, wherein each is independently a five-membered (furanose) or a six-membered (pyranose) monosaccharide residue.
15. The compound of claim 14, wherein at least one of said at least two monosaccharide residues comprises at least one amine group and/or at least one aminoalkyl group.
16. The compound of claim 15, wherein said at least one amine group is at position 2 of a pyranose monosaccharide residue.
17. The compound of claim 16, wherein said at least one aminoalkyl group is at position 5 of a pyranose monosaccharide residue.
18. The compound of claim 14, wherein said oligosaccharide comprises a furanose monosaccharide linked to a pyranose monosaccharide.
19. The compound of claim 14, wherein each of said at least two monosaccharide residues is independently a D-monosaccharide or a L-monosaccharide.
20. The compound of claim 1, wherein X is sulfur and R₁ is a monosaccharide residue.
21. The compound of claim 20, wherein said monosaccharide is a furanose monosaccharide residue.
22. The compound of claim 13, wherein said oligosaccharide residue comprises at least four monosaccharide residues, wherein each monosaccharide residue is independently a five-membered (furanose) or a six-membered (pyranose) monosaccharide residue.

23. The compound of claim 13, wherein said oligosaccharide residue is selected from the group consisting of a Neomycin B residue, a Paromomycin residue, a Ribostamycin residue, a Gentamycin residue, a Amikacin residue, a Neamine residue, a Nebramine residue and a Tobramine residue.
24. A pharmaceutical formulation comprising a therapeutically effect amount the compound of claim 1 and a pharmaceutically acceptable carrier.
25. A compound having the general formula II:

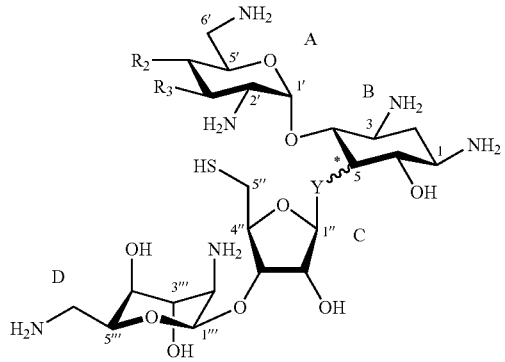

Formula II wherein:
Y is oxygen or sulfur;
R₂ and R₃ are each independently hydrogen, hydroxy, thiol, amine, alkyl, cycloalkyl, aryl, alkoxy, aryloxy, thioalkoxy or thioaryloxy, and
wherein the carbon at the fifth position of ring B has an R configuration or an S configuration;
or a pharmaceutically acceptable salt thereof.

26. The compound of claim 25, wherein Y is oxygen, and R₂ and R₃ are both hydroxy.
27. A pharmaceutical formulation comprising a therapeutically effective amount of the compound of claim 1 and a pharmaceutically acceptable carrier.
28. A compound having the general formula III:

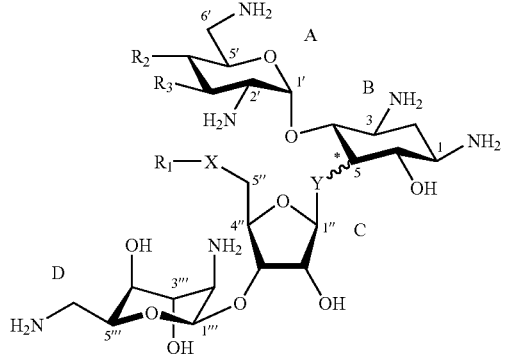

Formula III wherein:
R₁ is an oligosaccharide residue comprising at least two monosaccharide residues, wherein each is independently a five-membered (furanose) or a six-membered (pyranose) monosaccharide residue;
Y is oxygen or sulfur;
X is disulfide;

R_2 and R_3 are each independently selected from the group consisting of hydrogen, hydroxy, thiol, amine, alkyl, cycloalkyl, aryl, alkoxy, aryloxy, thioalkoxy and thioaryloxy; and wherein the carbon at the fifth position of ring B has an R configuration or an S configuration;

or a pharmaceutically acceptable salt thereof.

29. The compound of claim 28, wherein Y is oxygen.

30. The compound of claim 28, wherein $R_2$ and $R_3$ are both hydroxy.

31. The compound of claim 28, wherein said oligosaccharide residue comprises at least four monosaccharide residues, each of said monosaccharide residues is independently a five-membered (furanose) or a six-membered (pyranose) monosaccharide residue.

32. The compound of claim 28, wherein said oligosaccharide residue is selected from the group consisting of a Paromomycin residue, a Ribostamycin residue, a Gentamycin residue, a Amikacin residue, a Neamine residue, a Nebramine residue and a Tobramine residue.

33. A pharmaceutical formulation comprising a therapeutically effective amount of the compound of claim 28 and a pharmaceutically acceptable carrier.

34. A method for treating cystic fibrosis, the method comprising:
administering to a subject in need thereof a therapeutically effective amount of the compound of claim 1.

35. A method for treating anthrax, comprising administering to a subject in need thereof a therapeutically effective amount of the compound of claim 1.

36. A method for treating of a subject suffering from infection by an infectious microorganism, said infectious microorganism being a Gram negative organism, a Gram positive organism or a mycobacteria strain selected from the group consisting of *Strep. pyogenes* (Group A), *Strep. pneumoniae*, *Strep.* GpB, *Strep. viridans*, *Strep.* GpD (Enterococcus), *Strep.* GpC and GpG, *Staph. aureus*, *Staph. epidermidis*, *Bacillus subtilis*, *Bacillus anthracis*, *Listeria monocytogenes*, *Anaerobic cocci*, *Clostridium* spp., *Actinomyces* spp, *Escherichia coli*, *Enterobacter aerogenes*, *Kiebsiella pneumoniae*, *Proteus mirabilis*, *Proteus vulgaris*, *Morganella morganii*, *Providencia stuartii*, *Serratia marcescens*, *Citrobacter freundii*, *Salmonella typhi*, *Salmonella paratyphi*, *Salmonella typhi murium*, *Salmonella virchow*, *Shigella* spp., *Yersinia enterocolitica*, *Acinetobacter calcoaceticus*, *Flavobacterium* spp., *Haemophilus influenzae*, *Pseudomonas aeruginosa*, *Campylobacter jejuni*, *Vibrio parahaemolyticus*, *Brucella* spp., *Neisseria meningitidis*, *Neisseria gonorrhoea*, *Bacteroides fragilis*, *Fusobacterium* spp, *Mycobacterium tuberculosis* and *Mycobaterium smegmatis*, the method comprising:
administering to the subject a therapeutically effective amount of the compound of claim 25.

37. A method for treating cystic fibrosis, the method comprising:
administering to a subject in need thereof a therapeutically effective amount of the compound of claim 25.

38. A method for treating cystic fibrosis, the method comprising:
administering to a subject in need thereof a therapeutically effective amount of the compound of claim 28.

39. A method for treating anthrax, comprising administering to a subject in need thereof a therapeutically effective amount of the compound of claim 28.

40. Ethyl 2-O-Benzoyl-3,4-dideoxy-3,4-diazido-6-O-chloroacetyl-1-thio-β-D-allopyranoside (compound 9).

41. p-Methylphenyl-4,6-dideoxy-4,6-diazido-2,3-O-benzoyl-1-thio-β-D-glucopyranoside (compound 5f).

42. Ethyl 3,4-di-O-benzoyl-6-O-chloroacetyl-2-deoxy-2-phthalimido-1-thio-β-D-glucopyranose (compound 10).

43. p-Methylphenyl-2-deoxy-2-phthalimido-6-deoxy-6-azido-3,4-di-O-benzoyl-1-thio-β-D-glucopyranoside (compound 5e).

44. p-Methylphenyl-6-O-Acetyl-4-deoxy-4-azido-2,3-di-O-benzoyl-1-thio-β-D-glucopyranoside (compound 5c).

45. p-Methylphenyl-5-deoxy-5-azido-2,3-di-O-benzoyl-1-thio-D-ribofuranose (compound 8b).

46. p-Methylphenyl-5-deoxy-5-O-benzoyl-2,3-diazido-1-thio-D-ribofuranose (compound 24).

47. p-methylphenyl-2-O-Benzoyl-3,4-dideoxy-3,4-diazido-6-O-chloroacetyl-1-thio-β-D-allopyranoside (compound 7a).

48. p-Methylphenyl 3,4-di-O-acetyl-2,6-dideoxy-2,6-diazido-β-L-idopyranoside(1→3)-2-O-acetyl-5-O-tert-butyl-diphenylsylil-1-thio-β-D-ribofuranoside (Compound 19b).

49. A compound having the general formula IV:

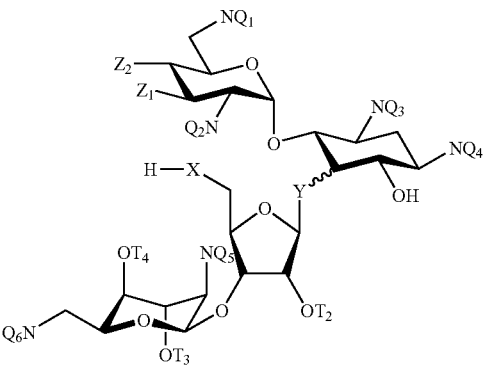

Formula IV wherein:
X is oxygen;
each of said $Z_1$, $Z_2$ is hydrogen;
each of said $OT_1$-$OT_4$ is an O-acetyl group;
each of said $NQ_1$-$NQ_6$ is an azido group;
Y is oxygen or sulfur; and
wherein the carbon at the fifth position of ring B has an R configuration or an S configuration.

50. A compound having the general formula IV:

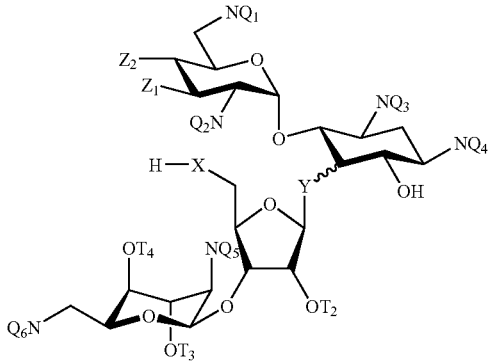

Formula IV wherein:
X is sulfur;
each of said $Z_1$, $Z_2$ and $OT_1$-$OT_4$ is an O-acetyl group;
each of said $NQ_1$-$NQ_6$ is an azido group;
Y is oxygen or sulfur; and
wherein the carbon at the fifth position of ring B has an R configuration or an S configuration.

51. A method of synthesizing the compound of claim 1, the method comprising:
(a) providing a compound having the general formula IV:

Formula IV

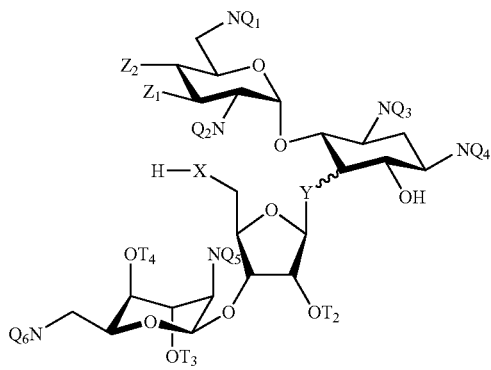

wherein:
each of $Z_1$ and $Z_2$ is independently selected from the group consisting of hydrogen, alkyl, cycloalkyl, aryl, a hydroxy protecting group, an amino protecting group and a thiol protecting group;
each of $T_1$-$T_4$ is independently a hydroxy protecting group;
each of $Q_1$-$Q_6$ is independently an amino protecting group;
X is oxygen or sulfur;
Y is oxygen or sulfur; and
wherein the carbon at the fifth position of ring B has an R configuration or an S configuration;
(b) providing a compound having the general formula V, VI or VII:

Formula V

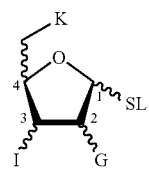

Formula VI

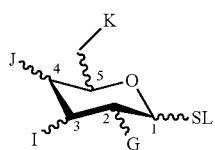

Formula VII

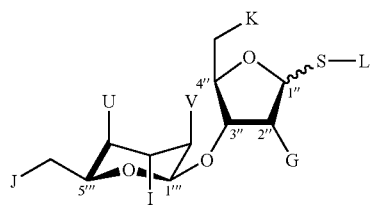

wherein:
each of G, I, J, K, U and V is independently selected from the group consisting of a hydroxy protecting group and an amino protecting group; and
SL is a thiolated leaving group;
(c) coupling said compound having said general formula IV and said compound having said general formula V, VI or VII; and
(d) removing each of said hydroxy protecting groups and said amino protecting groups, to thereby provide the compound of claim 1.

52. The method of claim 51, wherein said hydroxy protecting group is selected from the group consisting of O-acetyl, O-chloroacetyl and O-benzoyl.

53. The method of claim 51, wherein said amino protecting group is selected from the group consisting of an azido group and a N-phtalimido group.

54. The method of claim 51, wherein said thiolated leaving group is selected from the group consisting of thioethyl and para-thiotoluene.

55. A method of synthesizing the compound of claim 25, the method comprising:
(a) providing a compound having the general formula IV:

Formula IV

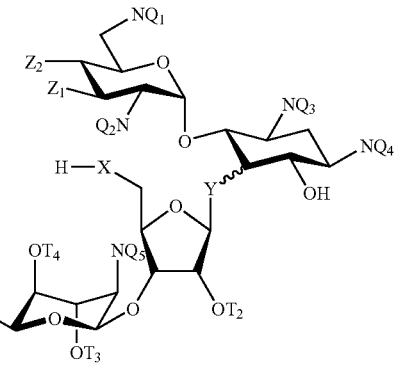

wherein:
each of $Z_1$ and $Z_2$ is independently selected from the group consisting of hydrogen, alkyl, cycloalkyl, aryl, a hydroxy protecting group, an amino protecting group and a thiol protecting group;
each of $T_1$-$T_4$ is independently a hydroxy protecting group;
each of $Q_1$-$Q_6$ is independently an amino protecting group;
X is sulfur;
Y is oxygen or sulfur; and
wherein the carbon at the fifth position of ring B has an R configuration or an S configuration; and
(b) removing each of said hydroxy protecting groups and said amino protecting groups, to thereby provide the compound of claim 25.

56. The method of claim 55, wherein said hydroxy protecting group is selected from the group consisting of O-acetyl, O-chloroacetyl and O-benzoyl.

57. The method of claim 55, wherein said amino protecting group is selected from the group consisting of an azido group and a N-phtalimido group.

58. A method of synthesizing the compound of claim 28, the method comprising:

(a) providing a compound having the general formula IV:

Formula IV

[chemical structure diagram showing Formula IV with substituents $NQ_1$, $Z_1$, $Z_2$, $Q_2N$, $NQ_3$, $NQ_4$, $OT_1$, $OT_2$, $OT_3$, $OT_4$, $NQ_5$, $Q_6N$, H—X, Y]

wherein:
each of $Z_1$ and $Z_2$ is independently selected from the group consisting of hydrogen, alkyl, cycloalkyl, aryl, a hydroxy protecting group, an amino protecting group and a thiol protecting group;
each of $T_1$-$T_4$ is independently a hydroxy protecting group;
each of $Q_1$-$Q_6$ is independently an amino protecting group;
X is sulfur;
Y is oxygen or sulfur; and
wherein the carbon at the fifth position of ring B has an R configuration or an S configuration;

(b) providing an oligosaccharide comprised of at least four monosaccharide residues and having at least one free thiol group attached to at least one of said monosaccharide residues, wherein any hydroxy group or amino group attached to said monosaccharide residues is protected by a hydroxy protecting group or an amino protecting group, respectively;

(c) coupling said compound having said general formula IV and said oligosaccharide, to thereby form a disulfide bond there-between; and (d) removing each of said hydroxy protecting groups and said amino protecting groups, to thereby provide the compound of claim 28.

59. The method of claim 58, wherein said oligosaccharide has said general formula IV.

60. The method of claim 58, wherein said hydroxy protecting group is selected from the group consisting of O-acetyl, O-chloroacetyl and O-benzoyl.

61. The method of claim 58, wherein said amino protecting group is selected from the group consisting of an azido group and a N-phtalimido group.

* * * * *

UNITED STATES PATENT AND TRADEMARK OFFICE
CERTIFICATE OF CORRECTION

| | | |
|---|---|---|
| PATENT NO. | : 7,635,685 B2 | Page 1 of 1 |
| APPLICATION NO. | : 11/073649 | |
| DATED | : December 22, 2009 | |
| INVENTOR(S) | : Timor Baasov et al. | |

It is certified that error appears in the above-identified patent and that said Letters Patent is hereby corrected as shown below:

On the Title page, insert in the section marked

Item [63]     Related U.S. Application Data

--US Application No. 10/829,976 filed on April 23, 2004--

Signed and Sealed this

Twenty-seventh Day of April, 2010

David J. Kappos
*Director of the United States Patent and Trademark Office*